US008557517B2

(12) United States Patent
Apetoh et al.

(10) Patent No.: US 8,557,517 B2
(45) Date of Patent: Oct. 15, 2013

(54) TOLL LIKE RECEPTOR 4 DYSFUNCTION AND THE BIOLOGICAL APPLICATIONS THEREOF

(75) Inventors: Lionel Apetoh, Boston, MA (US); Guido Kroemer, Antony (FR); Laurence Zitvogel, Antony (FR)

(73) Assignee: Institut Gustave Roussy, Villejuif Cedex (FR)

( * ) Notice: Subject to any disclaimer, the term of this patent is extended or adjusted under 35 U.S.C. 154(b) by 121 days.

(21) Appl. No.: 12/373,789

(22) PCT Filed: Jul. 17, 2007

(86) PCT No.: PCT/EP2007/057402
§ 371 (c)(1),
(2), (4) Date: Jan. 14, 2009

(87) PCT Pub. No.: WO2008/009693
PCT Pub. Date: Jan. 24, 2008

(65) Prior Publication Data
US 2010/0004161 A1    Jan. 7, 2010

(30) Foreign Application Priority Data
Jul. 18, 2006   (EP) .................................... 06291164

(51) Int. Cl.
*C12Q 1/68* (2006.01)
(52) U.S. Cl.
USPC ........................................................ 435/6.1
(58) Field of Classification Search
None
See application file for complete search history.

(56) References Cited

U.S. PATENT DOCUMENTS

| 2002/0156025 | A1 | 10/2002 | Paglin et al. |
| 2003/0166023 | A1 | 9/2003 | Iartchouk et al. |
| 2006/0147456 | A1 | 7/2006 | Lebecque et al. |
| 2006/0241139 | A1 | 10/2006 | Kastan et al. |

FOREIGN PATENT DOCUMENTS

| WO | WO 87/06830 | 11/1987 |
| WO | WO 02/074921 | 9/2002 |
| WO | WO 2004/044001 | 5/2004 |
| WO | WO 2005/040208 | 5/2005 |
| WO | WO 2006/054177 | 5/2006 |

OTHER PUBLICATIONS

Lazar et al. ( Mol. Cell Biol. 8:1247-1252, 1998).*
Tockman et al (Cancer Res., 1992, 52:2711s-2718s).*
Burgess et al. (J. Cell Biol. 111:2129-2138, 1990).*
Okamoto et al (Cancer Research, 2004, 64(15): 5461-5470).*
Wang et al (Biochem Biophys Res Commun, 2003, 305(4): 970-973).*
Rittersma et al (Clinical Chemistry, 2005, 51(3): 516-521).*
Guo et al (Journal of Gastroenterology and Hepatology, 2006, 21: 92-97).*
Hold et al (Gastroenterology, 2004, 126(4)(sup2):A531-A532).*
Sosnowski et al (Psychiatr Genet, 2002, 12(4): Abstract).*
Minsky (Clin Colorectal Cancer, 2004, Suppl 1: Abstract).*
Ahmed, S.U. et al. "Anti-Tumor Effect of an Intratumoral Administration of Dendritic Cells in Combination with TS-1, an Oral Fluoropyrimidine Anti-Cancer Drug, and OK-432, a Streptococcal Immunopotentiator: Involvement of Toll-Like Receptor 4" *Journal of Immunotherapy*, Nov. 2004, pp. 432-441, vol. 27, No. 6.
Barnes, K.R., et al. "Synthesis, Characterization, and Cytotoxicity of a Series of Estrogen-Tethered Platinum(IV) Complexes" *Chemistry & Biology*, Apr. 2004, pp. 557-564, vol. 11, No. 4.
Chen, Y.C. et al. "Sequence Variants of Toll-Like Receptor 4 and Susceptibility to Prostate Cancer" *Cancer Research*, Dec. 15, 2005, pp. 11771-11778, vol. 65, No. 24.
Cohen, S.B. et al. "Generation of a Monoclonal Antibody Agonist to Toll-Like Receptor 4" *Hybridoma*, Feb. 2005, pp. 27-35, vol. 24, No. 1.
Gekeler, V. et al. "G3139 and Other CpG-Containing Immunostimulatory Phosphorothioate Oligodeoxynucleotides Are Potent Suppressors of the Growth of Human Tumor Xenografts in Nude Mice" *Oligonucleotides*, Mar. 2006, pp. 83-93, vol. 16, No. 1.
Hold, G.L. et al. "A Functional Toll-Like Receptor 4 Polymorphism Increases the Risk of Gastric Cancer" *Gastroenterology*, Apr. 2004, pp. A531-A532, vol. 126, No. 4-Suppl. 2.
Kashimura, S. et al. "Experimental Study for a Combination Chemo-Immunotherapy Using Dendritic Cells" *Jpn J Cancer Chemother*, Oct. 2004, pp. 1631-1633, vol. 31, No. 11.
Okamoto, M. et al. "Expression of Toll-Like Receptor 4 on Dendritic Cells is Significant for Anticancer Effect of Dendritic Cell-Based Immunotherapy in Combination with an Active Component of OK-432, a Streptococcal Preparation" *Cancer Research*, Aug. 1, 2004, pp. 5461-5470, vol. 64, No. 15.
Shiratsuchi, A. et al. "Inhibitory Effect of Toll-Like receptor 4 on Fusion between Phagosomes and Endosomes/Lysosomes in Macrophages" *Journal of Immunology*, Feb. 2004, pp. 2039-2047, vol. 172, No. 4.

* cited by examiner

*Primary Examiner* — Sean Aeder
(74) *Attorney, Agent, or Firm* — Saliwanchik, Lloyd & Eisenschenck

(57) ABSTRACT

The present invention relates to an in vitro method of assessing the sensitivity of a subject to a treatment of cancer, which method comprises detecting the presence of a mutated Toll Like Receptor 4 (TLR4) nucleic acid or an abnormal TLR4 protein expression or activity in a sample from the subject, the presence of said mutated TLR4 nucleic acid or abnormal TLR4 expression or activity being indicative of a resistance to said treatment. The invention further provides compounds for treating or preventing a cancer in a subject having a mutated TLR4 nucleic acid or an abnormal TLR4 protein expression or activity.

30 Claims, 27 Drawing Sheets

A
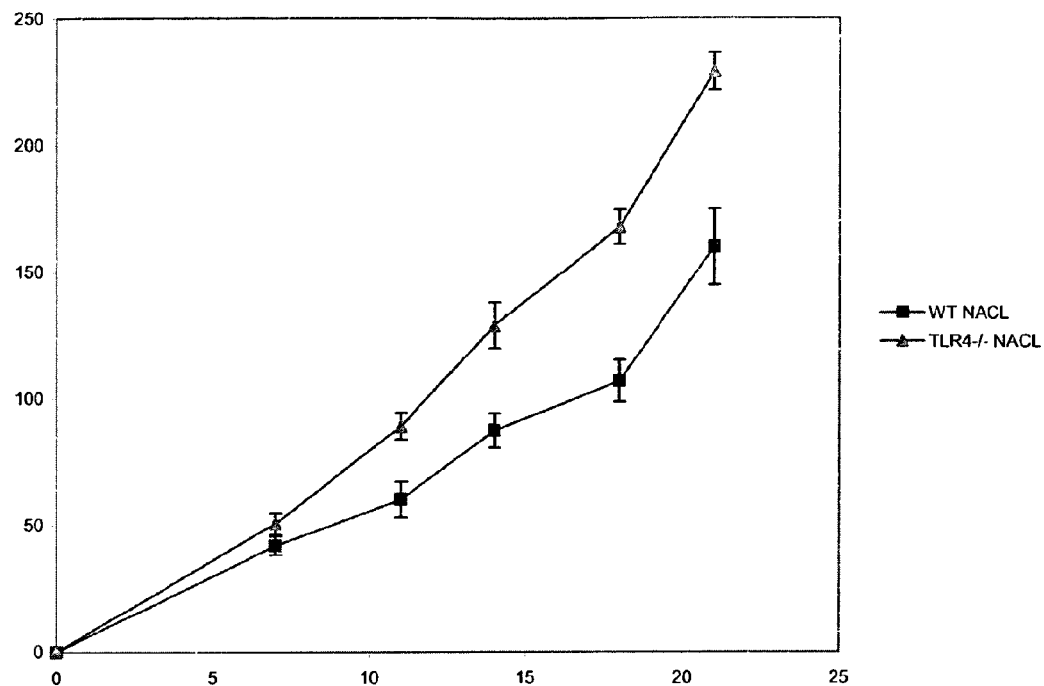
B
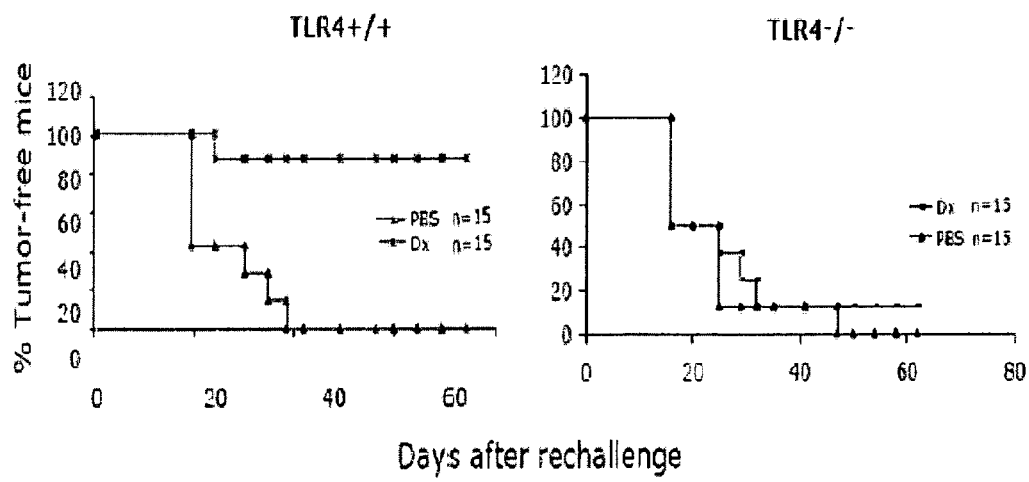
Figure 2

|  | Control group (n=112) | Breast Cancer (n=56) | p value |
|---|---|---|---|
| Age   m ± SD | 65.5 ± 12 | 65.7 ± 12 | NS |
| Female   n (%) | 112 (100) | 56 (100) | NS |
| Ethnic origin | | | |
| - Caucasian   n (%) | 93 (83) | 48 (85.7) | NS |
| - African   n (%) | 2 (1.8) | 1 (1.8) | NS |
| - Mediterranean   n (%) | 15 (13.4) | 6 (10.7) | NS |
| - Asian   n (%) | 2 (1.8) | 1 (1.8) | NS |
| Pathology | | | |
| - Control   n (%) | 54 (48.2) | 26 (46.4) | NS |
| - Shock   n (%) | 28 (25) | 16 (28.6) | NS |
| - Sepsis   n (%) | 30 (26.8) | 14 (25) | NS |
| Incidence of Asp299Gly mutation | 7 (6.3) | 12 (21.4) | 0.004 |

Figure 11B

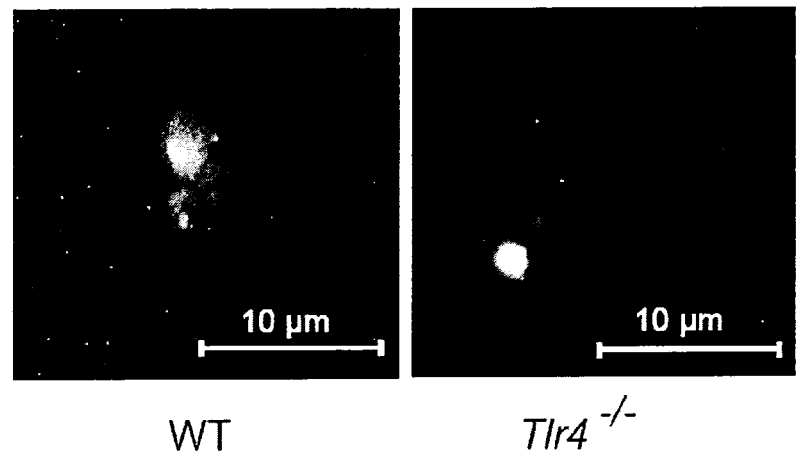
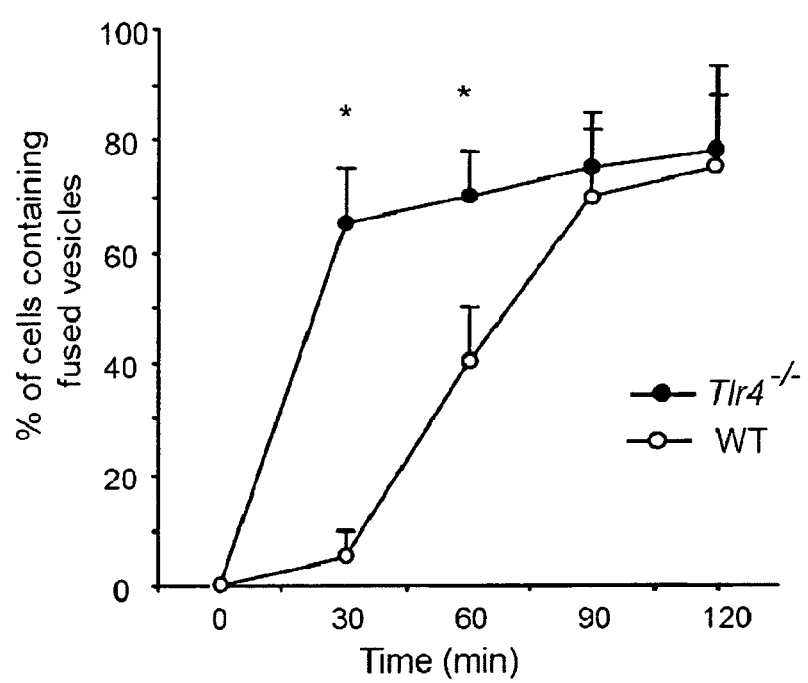
Figure 14c

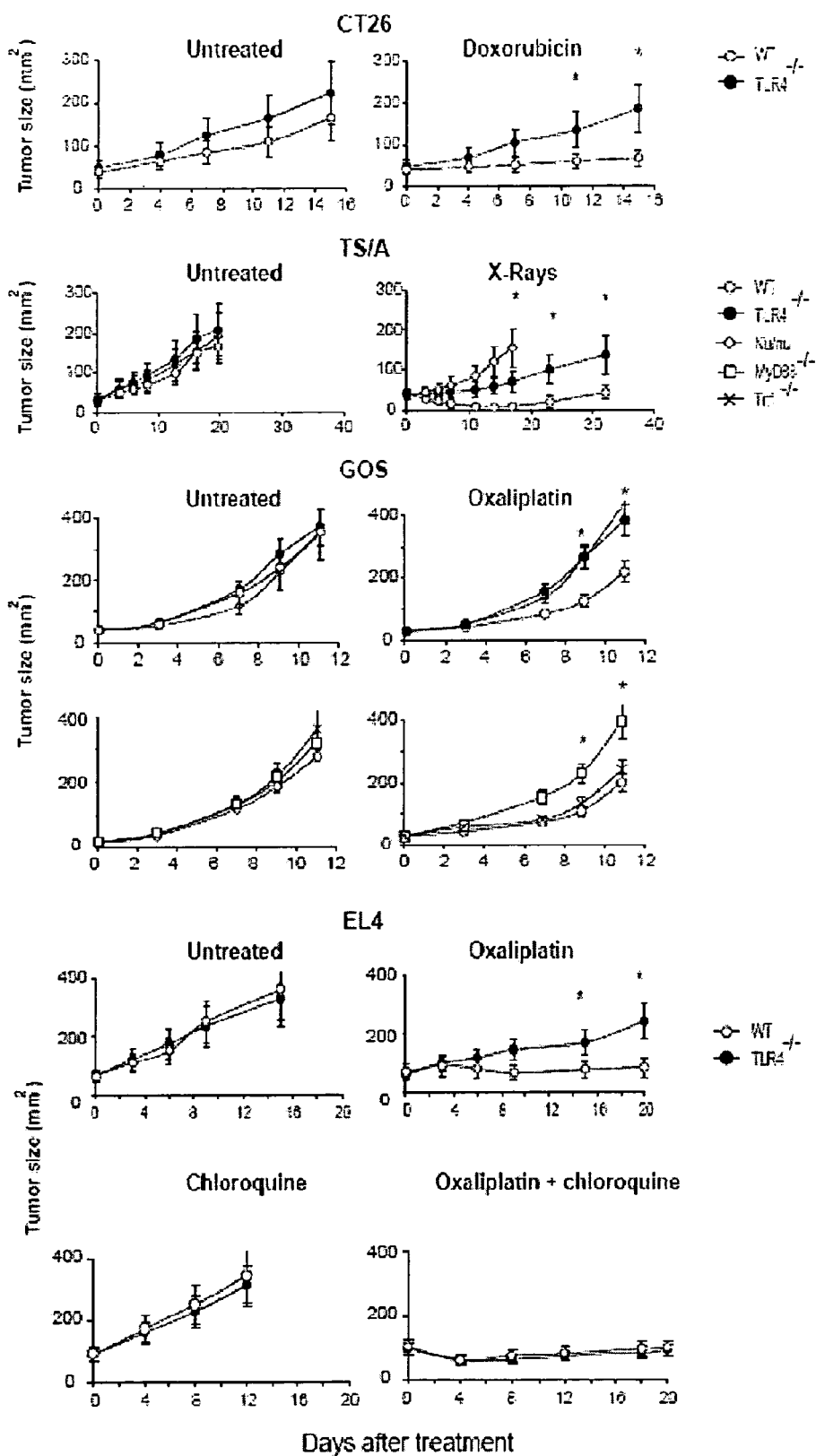
Figure 16a-d

TOLL LIKE RECEPTOR 4 DYSFUNCTION AND THE BIOLOGICAL APPLICATIONS THEREOF

Cross-Reference to Related Application

This application is the U.S. national stage application of International Patent Application No. PCT/EP2007/057402, filed Jul. 17, 2007, the disclosure of which is hereby incorporated by reference in its entirety, including all figures, tables and amino acid or nucleic acid sequences.

The present disclosure generally relates to the fields of genetics, immunology and medicine. The inventors more particularly discloses the identification of a human gene which can be used to predict or assess the sensitivity of a subject to a treatment of cancer. This human gene has further been herein identified as a cancer susceptibility gene which can be used for the prevention and treatment of cancer, as well as for the screening of therapeutically active drugs.

The present disclosure more specifically relates to an abnormal Toll Like Receptor 4 (TLR4) gene encoding a mutant TLR4 protein, said mutated gene and protein representing novel targets for therapeutic intervention. A particular TLR4 mutant preferably comprises a single mutation of the asparagine at position 299.

The disclosure further relates to an abnormal TLR4 protein expression or activity.

The invention can be used in a method of determining a predisposition to a cancer in a subject and/or in the prevention or treatment of cancer.

BACKGROUND ART

Innate immune responses to pathogens are mainly orchestrated by monocytes, macrophages, granulocytes and dendritic cells, which act as a first line of defense against invading microorganisms [1]. Discrimination between self and non self relies on host proteins equipped with the ability to recognize molecular patterns present on foreign organisms [2] [3]. One major family or proteins are the Toll like receptors (TLR), also referred to as pattern recognition receptors (PRR).

TLR4 recognizes lipopolysaccharide (LPS) from Gram negative bacteria, through an extracellular domain characterized by leucine-rich repeats [4], [5], [6]. After its binding to LPS-binding protein (LBP), LPS is transported to a receptor complex involving CD14, TLR4 and an adaptor molecule MD2. Signal transduction is initiated by the interaction of the TIR domain (Toll/IL-1 receptor) of TLR4 with MyD88 (myeloid differentiation primary response protein 88) [7]. A MyD88-independent pathway has been elucidated for TLR4, involving proteins such as Toll-IL1R domain-containing adaptor protein inducing IFN beta (TRIF), TRIF-related adaptor molecules, TANK binding kinase 1 (TANK: TNF receptor associated NFκB kinase) and IκB kinase ε, which then leads to induction of type 1 IFN via interferon regulatory factor 3 (IRF3) [8], [9], [10], [11].

Genetic polymorphisms, for the most part single nucleotide polymorphisms (SNP), are common variants within a population that are found at a frequency of over 1%. They may alter the amino acid sequence (non synonymous SNP), affect the promoter or be silent. Two SNP have been identified within the promoter region of CD14 and one of them, Cys159Thr is related to the incidence and mortality of septic shock [12].

More importantly, SNP in the extracellular domain of TLR4 have been largely investigated. Two co-segregating SNP within the gene encoding TLR4 exhibiting allele frequencies greater than 2% are Asp299Gly and Thr399Ile [13]. These mutations were found in about 10% (0-19%) of control white individuals in most studies. The functional relevance of SNP Asp299Gly has been investigated in hyporesponsiveness to inhaled LPS and allergic asthmatics [13], on the incidence and course of septic shock and various infectious diseases or pathogenesis of atherosclerosis. Accumulating but controversial data point to a role of such SNP TLR4 in altered susceptibility or in the course of these inflammatory or infectious diseases (including allograft reactions, diabetes, coronary stenosis) (reviewed in [14]). One mutated allele is required for the dysfunction [13]. Among 91 people with septic shock during Gram neg. bacteria infection, 4 displayed the Asp299Gly SNP (but not the Thr399Ile) while 0 SNP was detected in the control group [15]. Colonization of pregnant women with *Gardnerella* spp and other Gram neg commensals was increased by 10 fold in women carrying the mutated Thr399Ile TLR4 allele [16]. A clear correlation was found between severe respiratory syncitial virus (RSV) bronchiolitis in infants and both TLR4 SNP while no correlation with CD14 SNP was found [17].

Blocking of TLR4 may have a beneficial effect on atherosclerosis in mice and two studies found a protective effect of the TLR4 variants on acute coronary events [18], [19], [20]. Rare SNP of TLR4 might also be relevant in some cases such as meningococcemia where Asp299Gly/Thr399Ile were not significant (extracellular region and C terminal domain in the TIR region, [21], [22]).

Functional assays using whole PBMC or monocytes aimed at detecting dysfunctional TLR4 may not be relevant [23], [24], [25].

The association of the SNP with susceptibility to infectious diseases can thus only be regarded as preliminary since studies reporting positive correlations were done with small populations. The finding that the presence of SNP does not influence the activation of monocytes or whole blood by its ligands is further evidence against the hypothesis of a potential role for these SNP in infectious disease susceptibility.

A role for TLR4 polymorphism and cancer has been recently addressed because chronic inflammation may expose to higher risk of tumourigenesis. A TLR4 SNP at position 11 381 was found in Sweden to be more frequent (24.1% versus 19.7%, p=0.02) among people with prostate cancer [26]. A more recent study also concluded that inherited polymorphisms of the innate immune gene TLR4 are associated with risk of prostate cancer [27]. Homozygosity for the variant alleles of eight SNPs was associated with a statistically significantly lower risk of prostate cancer (TLR4_1893, TLR4_2032, TLR4_2437, TLR4_7764, TLR4_11912, TLR4_16649, TLR4_17050, and TLR4_17923), but the TLR4_15844 polymorphism corresponding to 11381G/C was not associated with prostate cancer (GG versus CG/CC: OR, 1.01; 95% confidence interval, 0.79-1.29). Six common haplotypes (cumulative frequency, 81%) were observed; the global test for association between haplotypes and prostate cancer was statistically significant [chi(2)=14.8 on 6 degrees of freedom; P=0.02]. Two common haplotypes were statistically significantly associated with altered risk of prostate cancer.

The first demonstration of a modulatory role for TLR4 in chronic lung inflammation and tumourigenesis has been brought up by Bauer A K et al. [28]. To determine the role of TLR4 in chronic lung inflammation, they compared lung permeability, leukocyte infiltration, and nuclear factor kappa B (NFkappaB) and activator protein 1 (AP-1) DNA binding in butylated hydroxytoluene (BHT)-treated inbred mouse strains with functional TLR4 (OuJ and BALB) and mutated TLR4 [HeJ and BALB(Lps-d)]. They also measured primary tumour formation in these mice after single-carcinogen injection (3-methylcholanthrene) followed by BHT treatment. Mice with functional TLR4 had reduced lung permeability, leukocyte inflammation, and primary tumour formation (BALB(Lps-d), mean=22.3 tumours/mouse, versus BALB, mean=13.9 tumours/mouse, difference=8.4 tumours/mouse, 95% confidence interval=4.6 to 12.1 tumours/mouse; P=0.025) compared with mice with mutated TLR4. NFkappaB DNA binding activity was higher in OuJ than in HeJ mice; however, AP-1 activity was elevated in HeJ mice.

More recently, Okamoto et al. [29], described a correlation between the absence of TLR-4 expression in patients with head and neck cancer and a decreased response to a particular therapeutic treatment comprising the administration of OK-PSA or OK-432, optionally together with UFT (tegafur: uracil, 1:4), and optionally together with a radiotherapy. This document however does not describe or suggest a method according to the present invention of assessing the sensitivity of a subject to a treatment of cancer consisting in a chemotherapeutic treatment of cancer.

Combating cancer efficiently relies on pharmaceutical compounds directly targeting tumour cells or boosting host defense against said cells. Although several anti-cancer therapies are proposed, amongst which feature chemotherapy [anthracyclines, such as doxycycline (DOX), oxali-platinum (herein called PLAT) and cis-platinum (herein called PLAT) are considered as the most efficient cytotoxic agents of the oncologist armamentarium] and radiotherapy [X-Rays (XR)], the benefits of said treatments still tends to be insufficient. Since anthracyclines, oxaliplatinum, cis-platinum and X-Rays represent the basis of up to 70% of anti-cancer therapies, detection of dysfunctions responsible for a reduced response to said treatments appears critical for patient management.

SUMMARY

A method of assessing the sensitivity of a subject to a treatment of cancer, in particular to a chemotherapeutic treatment, is herein disclosed. The method comprises detecting the presence of a mutated TLR4 nucleic acid or an abnormal TLR4 protein expression or activity in a sample from the subject, the presence of said mutated TLR4 nucleic acid or abnormal TLR4 expression or activity being indicative of a resistance to said treatment.

Particular mutations in the TLR4 gene and expression products are further described. These mutations are usable in a method for assessing the sensitivity of a subject to a treatment of cancer. Certain alleles of the TLR4 gene are also related to susceptibility to cancer and represent targets for therapeutic intervention.

A method of determining a predisposition to a cancer or an increase likelihood of having a cancer in a subject is also herein described, the method comprising detecting the presence of a mutated TLR4 nucleic acid or an abnormal TLR4 protein expression or activity in a sample from the subject. A particular method comprises the detection of the presence of a mutated TLR4 sequence comprising a point mutation, preferably a single nucleotide polymorphism (SNP) leading to the substitution of asparagine by glycine at position 299 or of threonine by isoleucine at position 399, in a sample from the subject.

A method for screening compounds useful for preventing or treating cancer in particular in a subject having a mutated TLR4 nucleic acid or an abnormal TLR4 protein expression or activity, is also described. Said method comprises determining the ability of a test compound to modulate the expression or activity of TLR4 or the relocalization to tumour cell plasma membrane of TLR4 ligands, such as HMGB1 (high molecular weight box 1 HMGB1/amphoterin).

The present application further describes the use of a compound capable of restoring a functional TLR4 expression to prepare a pharmaceutical composition for treating or preventing a cancer in a subject having a mutated TLR4 nucleic acid or an abnormal TLR4 protein expression or activity.

The present application also describes a compound capable of restoring a functional TLR4 expression and a pharmaceutical composition comprising such a compound to prevent or treat a cancer in a subject having a mutated TLR4 nucleic acid or an abnormal TLR4 protein expression or activity.

Applicants further describe the use of a TLR3 and/or TLR9 ligand to prepare a pharmaceutical composition for treating or preventing a cancer in a subject having a mutated TLR4 nucleic acid or an abnormal TLR4 protein expression or activity. Such ligands allow to bypass the TLR4 signaling pathway and lead to NF-κB activation.

The present invention also encompasses a TLR3 and/or TLR9 ligand capable of restoring a functional TLR4 expression and a pharmaceutical composition comprising such a TLR3 and/or TLR9 ligand to prevent or treat a cancer in a subject having a mutated TLR4 nucleic acid or an abnormal TLR4 protein expression or activity.

Applicants further describe the use of an alcalinizing lysosomotropic compound to prepare a pharmaceutical composition for treating or preventing a cancer in a subject having a mutated TLR4 nucleic acid or an abnormal TLR4 protein expression or activity.

The present invention also encompasses an alcalinizing lysosomotropic compound and a pharmaceutical composition comprising such a compound to prevent or treat a cancer in a subject having a mutated TLR4 nucleic acid or an abnormal TLR4 protein expression or activity.

The invention also lies in method of treating or preventing a cancer in a subject through an activation of TLR4 expression or activity.

More particularly, methods of treating a subject who carries mutated alleles of the TLR4 gene, which methods include employing combined therapy, are herein provided. Subjects may thus be treated for example through gene therapy, protein replacement therapy or through the administration of TLR4 protein mimetics and/or activators, such as HMGB1. At least one of said methods may further be combined to a chemotherapy and/or to a radiotherapy.

Each experiment included 5-10 mice/group and was performed at least twice yielding similar results. Statistical analyses were performed using Fisher's exact method and ANOVA. * indicate significant results at p<0.05.

Figure 3:
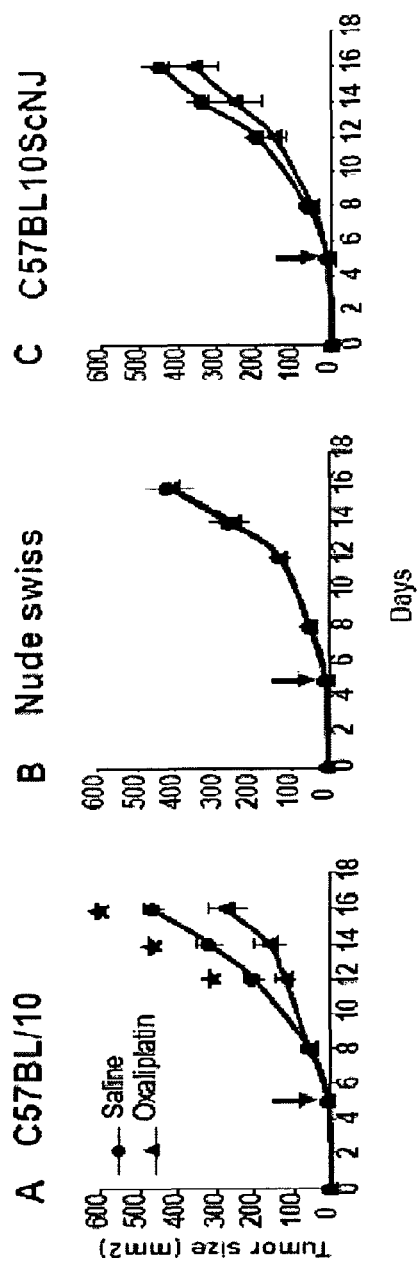

FIG. 3: TLR4 is involved in oxaliplatinum-induced tumour regression.

The Glasgow osteosarcoma (GOS) was inoculated at day 0 in WT C57BL/6 (A.) or Nude Swiss (B.) or C57BL10ScNJ (C.) mice. Oxaliplatinum (or PBS) was administered at day 5 systemically and tumour growth was monitored. Each experiment included 5 mice/group and was performed at least twice yielding similar results. Statistical analyses were performed using Student t'test. * indicate significant results at p<0.05.

Figure 4:
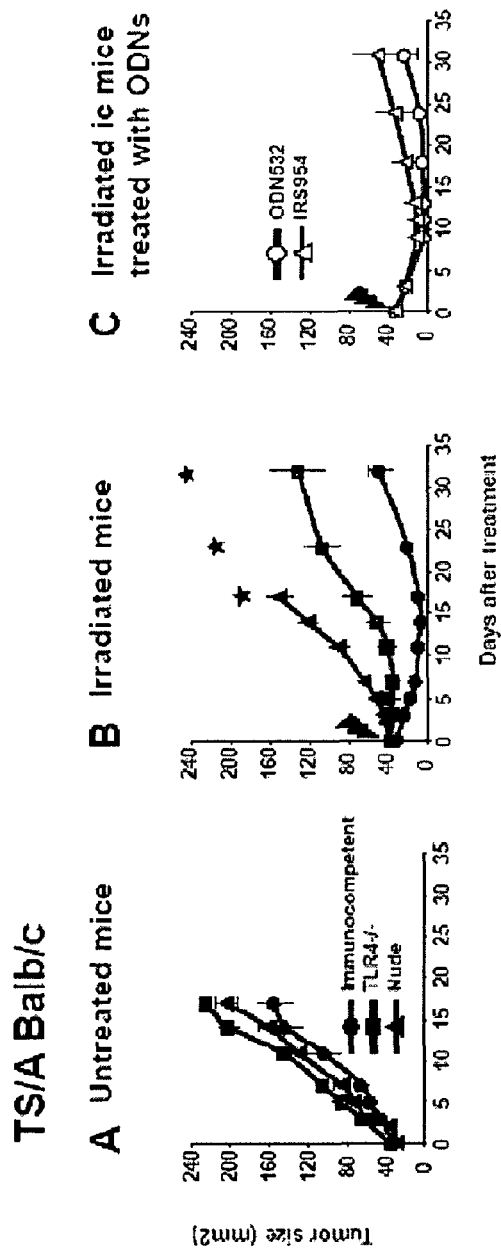

FIG. 4: X-Rays control tumour progression at least in part through TLR4.

The TS/A mammary tumour was inoculated in IC BALB/c, Nude BALB/c or TLR4−/− BALB/c mice (A.) and irradiated at 10 Gy in one shot when reaching a size of 30-50 mm2 (around day 9-12) (B.). (C.) ODN-based inhibitors of TLR7/9 were inoculated i.p. prior to and after radiotherapy. Tumour size was monitored twice a week. Each experiment included 5 mice/group and was performed at least three times yielding similar results. Statistical analyses were performed using Fisher's exact method. * indicate significant results at p<0.05.

Figure 5:
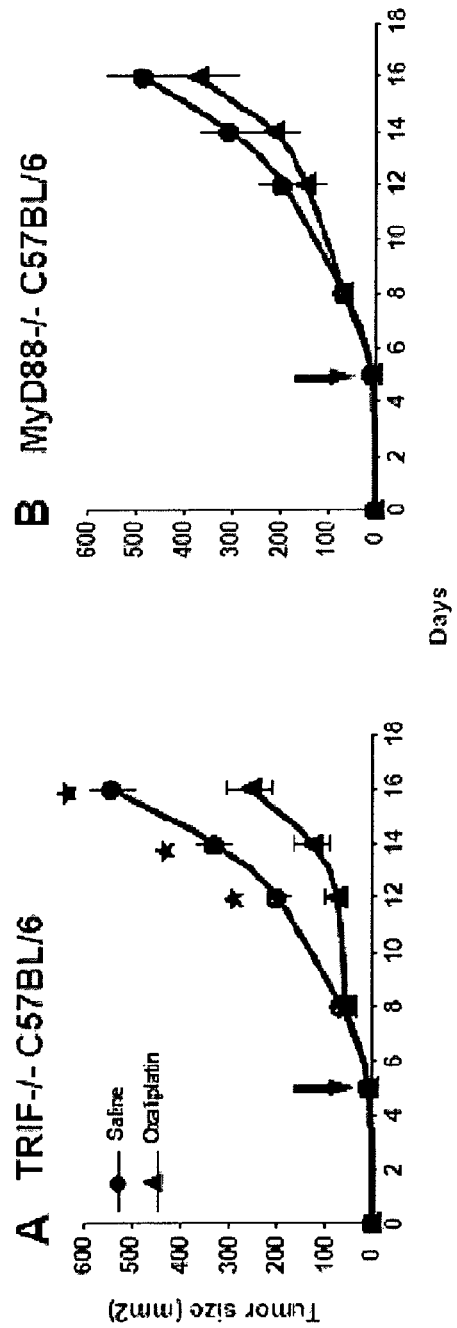

FIG. 5: MyD88 is involved in oxali-platinum-mediated immunogenicity.

Id. setting as in 3A but GOS was implanted into TRIF−/− (A) or MyD88−/− BL/6 (B) mice. Tumour size was monitored twice a week. Each experiment included 5 mice/group and was performed at least three times yielding similar results. Statistical analyses were performed using Fisher's exact method.

* indicate significant results at p<0.05.

Figure 6:
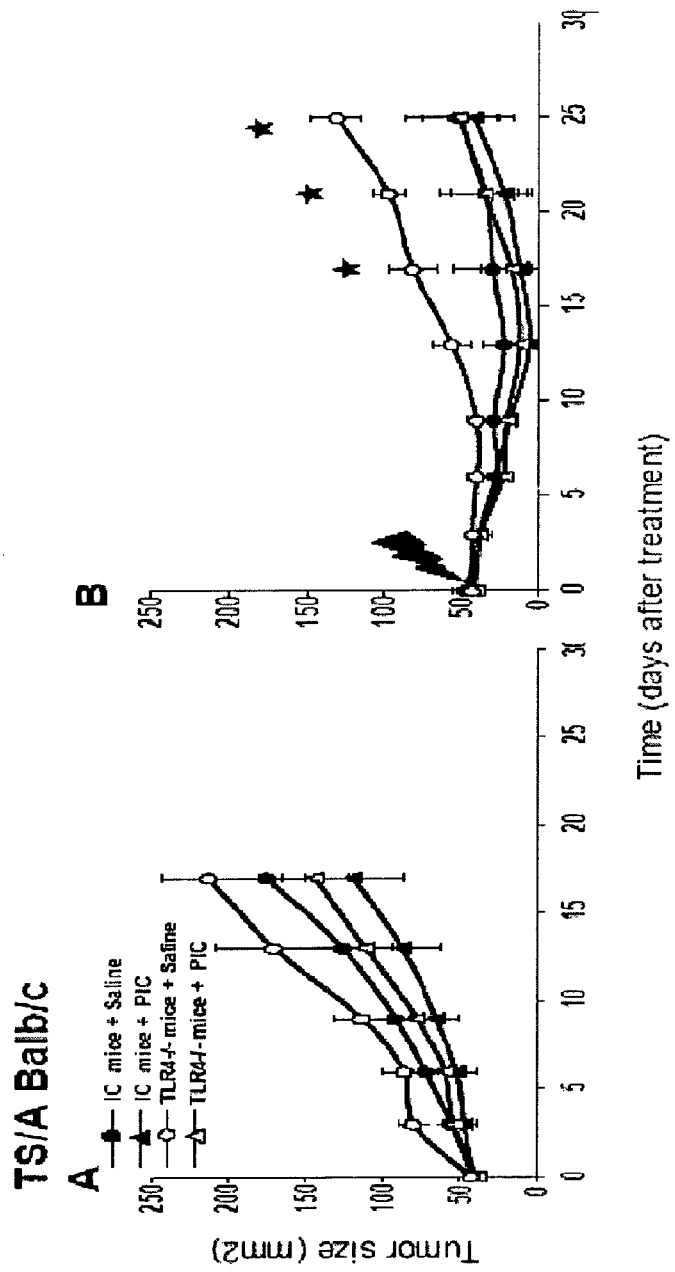

FIG. 6: TLR4$^{-/-}$ mice recover full sensitivity to X Rays in the presence of TLR3 ligands.

Id. as in 4. but concomitant therapy with 50 μg of polyI:C was administered i.p. at days +1, +4 and +7 after radiotherapy into TS/A bearing-animals (A) receiving also radiotherapy (B).

Tumour size was monitored twice a week. Each experiment included 5 mice/group and was performed at least three times yielding similar results. Statistical analyses were performed using Fisher's exact method. * indicate significant results at p<0.05.

Figure 7:
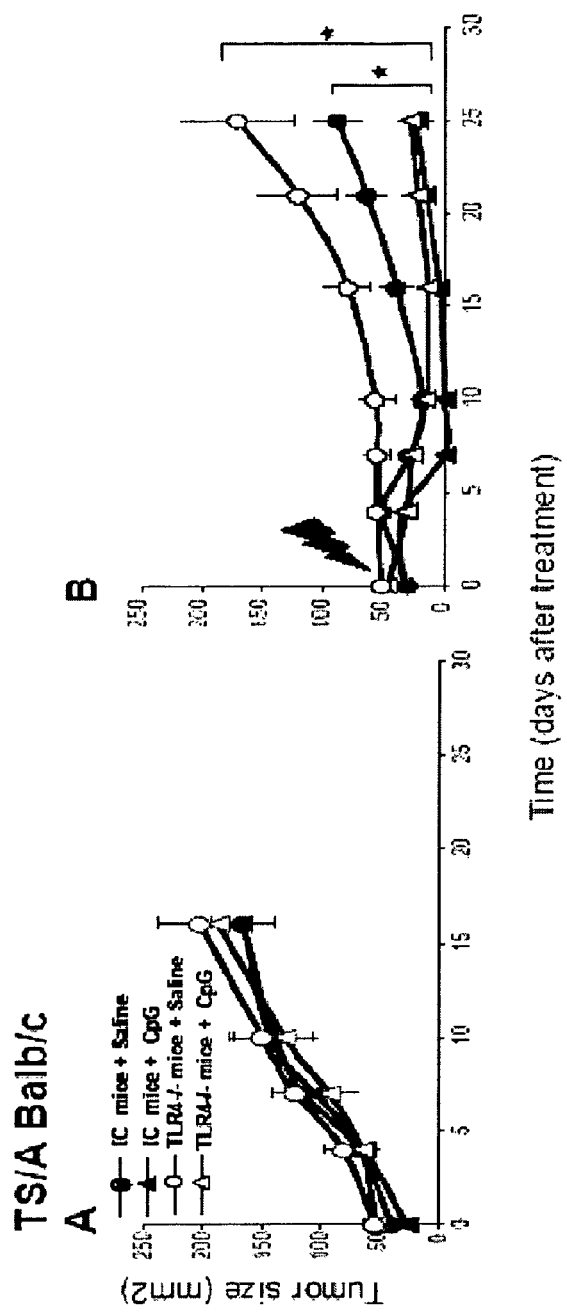

FIG. 7: TLR4$^{-/-}$ mice recover full sensitivity to X Rays in the presence of TLR9 ligands.

Id. as in 6. but instead of polyI:C, animals received 50 μg of CpG ODN 5'-TCCATGACGTTCCTGACGTT-3' (SEQ ID NO:8).

FIG. 8: Phagocytosis and maturation are not hampered in TLR4$^{-/-}$ DC.
A. apoptotic EL4OVA labelled with 1 μM CytoTracker Red—(CMTMR; Invitrogen) were incubated at 1:1 with BM-DC (from TLR4$^{+/+}$ or TLR4$^{-/-}$ mice) at an immature stage for 4 hrs at 37° C or 4° C. Flow cytometry analyses gating on CD11c+ cells allowed the determination of the % of PE positive dendritic cells. One representative experiment is depicted.
B. Id. as in A. but EL4OVA were not labelled with CMTMR and CD11c+ cells were examined for I-A$^B$ and CD86 surface expression. A representative experiment is depicted in upper (TLR4$^{+/+}$) and lower (TLR4$^{-/-}$) panels.

FIG. 9: TLR4−/− DC exhibit defective capacities to activate B3Z clone and cross present cell associated tumour antigens
A. The B3Z clone which is an OVA specific CTL, has been incubated with H2b syngeneic bone marrow DC for C57BL/10 or C57BL10ScNJ mice (BM-DC) pulsed with EL4-OVA (irradiated or not) or with untransfected EL4. B3Z secretes IL-2 which can be measured by ELISA in supernatants. IL-2 dosage has been performed in experiments at different ratios between BMDC and irradiated EL4OVA cells.
B. EL4-OVA, irradiated or not, were injected into the footpad at day 0 in Balb/c TLR4$^{-/-}$ or TLR4$^{+/+}$ host. Gangliocytes were harvested and challenged with OVA protein for 4 days and supernatants were collected for IFNγ measurements at day 3. At day 3, tritiated thymidine was added to these wells, and proliferation was monitored in cpm.

FIG. 10: HMGB1 is a critical ligand for TLR4 triggering during induction of stress by anthracyclines and X-Rays.
A. The B3Z clone which is an OVA specific CTL, has been incubated with H2b syngeneic bone marrow DC (BM-DC) pulsed with EL4-OVA (irradiated or not) or with untransfected EL4. B3Z secretes IL-2 which can be measured by ELISA in supernatants. IL-2 dosage has been performed in experiments at different ratios between BMDC and EL4OVA irradiated cells in the presence of blocking TLR4Fc molecules or isotype control Abs.
B. Idem but in the presence of anti-HMGB1 Antibodies (Abs) or isotype control Abs.

Figure 11A:
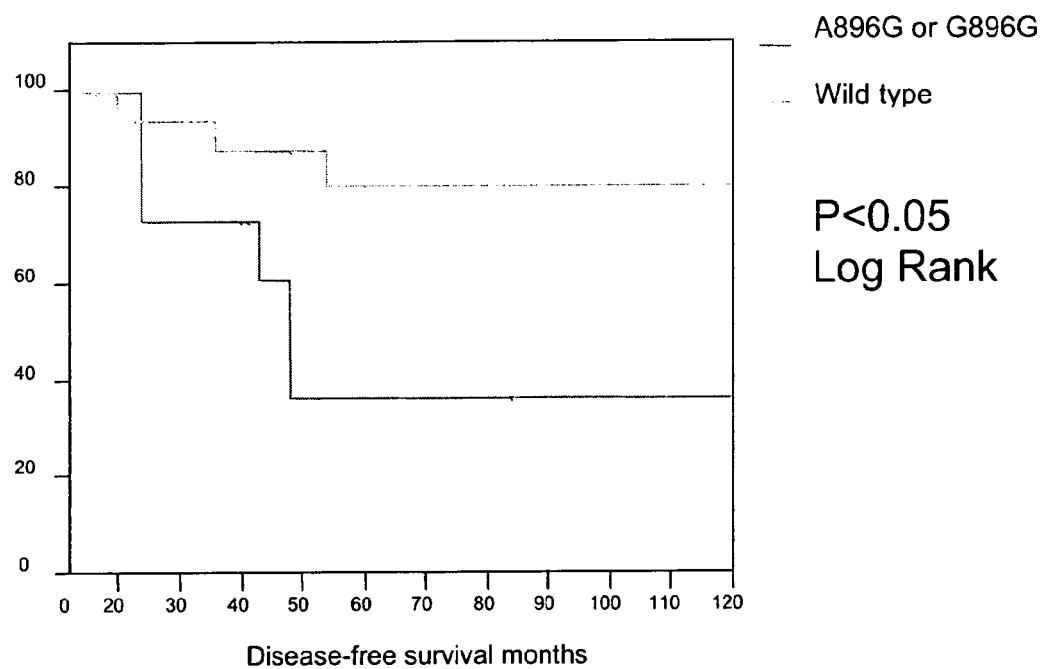

FIG. 11: Genotyping of breast cancer female for Asp299Gly TLR4.
A. Primary resistance to anthracycline and X-Rays in breast cancer (BC) female. 12 BC women bearing a TLR4 Asp299Gly TLR4 genotype were matched with 24 BC female of a wt genotype for age, Nottingham prognostic index and adjuvant therapy (anthracycline and X-Rays-based). The progression free survival (within 5 years) is depicted and is significantly longer in females bearing a wt genotype (Log Rank).
B. Genetic susceptibility to breast cancer. Patients were admitted to an emergency unit for 2 years and monitored for a comorbidity (cancer for ex.). 640 cases of patients bearing a cancer in their present or past history were registered in this study. They were classified according to their histological subtype. Single tube PCR based on exonuclease degradation of dual labelled allele specific oligonucleotides was performed on genomic DNA from patients' blood. The percentage of heterozygosity (one mutated allele of Asp299GlyTLR4) is depicted for each cohort of n individuals. The frequency of Asp299Gly is significantly higher in patients presenting with a sporadic breast.

Figure 12:
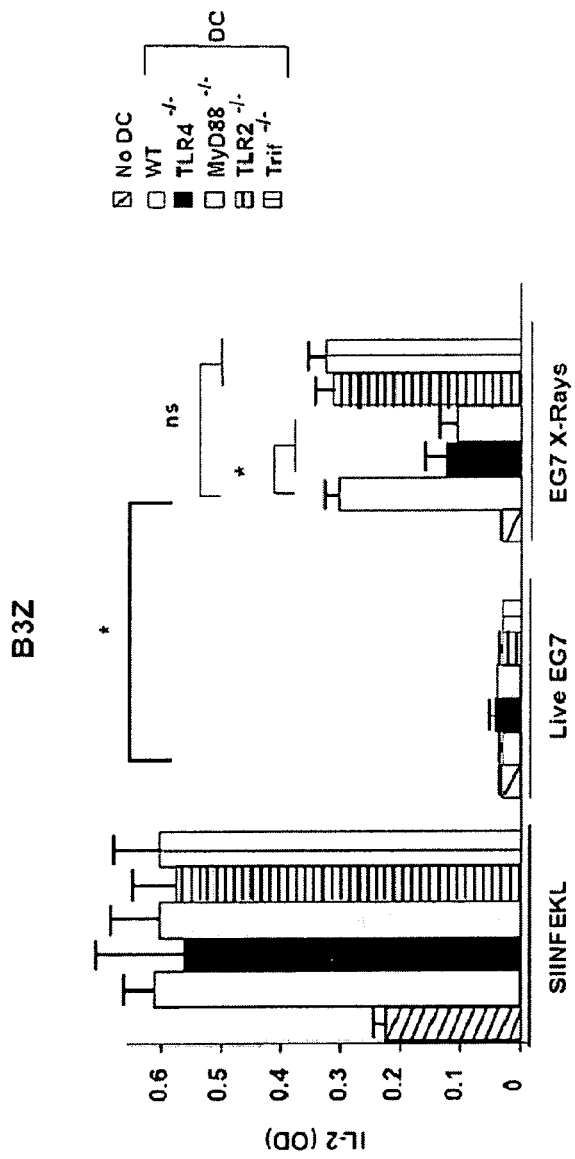

FIG. 12: TLR4 controls antigen presentation by DC engulfing apoptotic bodies in vitro.

TLR4 and MyD88 are required for antigen presentation by DC loaded with irradiated tumor cells to MHC class I (H-2$^b$)-restricted T cells. DC from the indicated genotype (background C57Bl/6, H-2$^b$ I-A$^b$) were pulsed with SIINFEKL peptide, live or irradiated EG7 cells (ratio of EG7 to DC 1:1)

and incubated with the SIINFEKL-specific B3Z hybridoma for 48 h, followed by quantification of IL-2 in the supernatant (see §12 of experimental section).

FIG. 13: Normal phagocytosis by TLR4-deficient DC and normal maturation of TLR4-deficient DC.

A. Phagocytosis of dying tumor cells is TLR4 independent.

Phagocytosis index of DXR treated CT26 (left panel) and irradiated-EL4 cells (right panel) by syngenic WT or TLR4$^{-/-}$ or Trif-/- or MyD88-/- DC. In 12-well plates, tumor cells were labeled with Celltracker Green (Calbiochem) and cultured with DC for 2 hours at a ratio of 1:1. At the end of the incubation, adherent cells were harvested with versene, pooled with non-adherent cells, washed and stained with CD11c-APC antibody. Phagocytosis was assessed by FACS analysis of double positive cells. Phagocytic indexes refer to the ratio between values obtained at 4° C. and values obtained at 37° C. of co-incubation between DC and tumor cells.

B. Mouse dendritic cell maturation induced by dying tumor cells is TLR4 independent. Murine C57BL/6 BM-DC were cultured 24 hours with live irradiated EG7 cells (at a 1:1 ratio) or LPS. After 24 hours, coculture supernatants were collected and the detection of mouse TNFα, IL-12p40 and IL-6 was performed by ELISA.

LPS, which a ligand of TLR-4, is used as a positive control.

FIG. 14: TLR4 deficiency in dendritic cells affects the processing of tumor cell derived antigens.

A. (upper panel) WT or TLR4$^{-/-}$ mouse BM-DC were loaded with irradiated TS/A-OVA cells. At indicated time points, CD11c+ cells expressing K$^b$-SIINFEKL were detected using anti-CD11c and anti-K$^b$-SIINFEKL antibodies. Unpulsed DC were used to set the positivity threshold for the K$^b$-SIINFEKL antibody. K$^b$ expression on both types of DCs was verified by assessing the MFI of labeled DCs with the anti-K$^b$ antibody. (lower panel) Same setting as in upper panel with either 0.5 µM chloroquine or 10 µg/ml of Anti-HMGB1 antibody. *p<0.01. CO=control.

B. WT or TLR4$^{-/-}$ mouse BM-DC were loaded with 1 mg/ml OVA protein (which can be assimilated to a soluble antigen) or irradiated EG7 cells (which can be assimilated to an apoptotic body), in the absence or presence of the indicated concentrations of chloroquine or bafilomycin A1. Six hours later, BM-DC were washed and incubated with the B3Z hybridoma for 48 h (as in FIG. 12), said hybridoma reacting to the presentation of an antigen by DC. Similar results (means of triplicates±SEM, n=3) were obtained in two experiments. *p<0.01.

C. WT or TLR4$^{-/-}$ mouse BM-DC were stained with the lysotracker red and loaded with irradiated CFSE-labeled EG7 cells. Unfused phagosomes that contained CFSE-labeled target cells were seen in green, whereas those fused with endosomes/lysosomes were seen in yellow due to the coexistence of the two fluorochromes. Determination of percentage of fused phagosomes in DC which engulfed targets was then assessed by fluorescence microscopy at different time points.

Fusion of endosomes/lysosomes is accelerated in TLR-4$^{-/-}$ mouse BM-DC.

FIG. 15: TLR4 and its ligand HMGB1 are both required for the success of vaccination against tumor cells.

A. Impact of TLR4 on the vaccination with dying tumor cells. Mice were immunized with PBS or dying tumor cells (CT26, EL4 or MCA205) treated with oxaliplatin-doxorubicin or X-irradiation. Seven days later, mice (10 per group) were inoculated with live syngeneic tumor cells and tumor growth was monitored.

B. Inhibition of TLR4 signaling dampers the efficacy of vaccination with dying tumor cells. Same settings as in A. using mice which were previously injected (day-7 and day-3) with 100 µg of a TLR4 inhibitory peptide (control peptide=CO).

C. Impact of HMGB1 on the vaccination with dying tumor cells. Experiment was done as in A. and B. with CT26, EL4 and MCA205. For anti-tumor vaccination, cells were transfected with a control or HMGB1-depleting siRNA prior to chemotherapeutic or radiotherapeutic treatment. *p<0.05.

FIG. 16: TLR4 dictates the efficacy of anti-tumor chemotherapy and radiotherapy in mice.

A.-D. Impact of TLR4, MyD88, TRIF and T cells on the efficacy of conventional anti-tumor therapy. EL4 thymoma, CT26 colon cancer, TS/A mammary cancer, and GOS osteosarcoma tumors were established in mice with the indicated genotypes. At the indicated tumor size, mice were either left untreated or treated by systemic chemotherapy or localized radiotherapy.

Wild type or TLR4$^{-/-}$ mice carrying EL4 tumors were treated with oxaliplatin and/or chloroquine (50 µg i.p. once a day). In FIG. 16D. a correction of the defective chemotherapeutic response of TLR4$^{-/-}$ mice is obtained using chloroquine.

Results (mean of triplicate±SEM, 5 mice per group) obtained in A.-D. are representative of three independent experiments. * p<0.05.

Figure 17A:
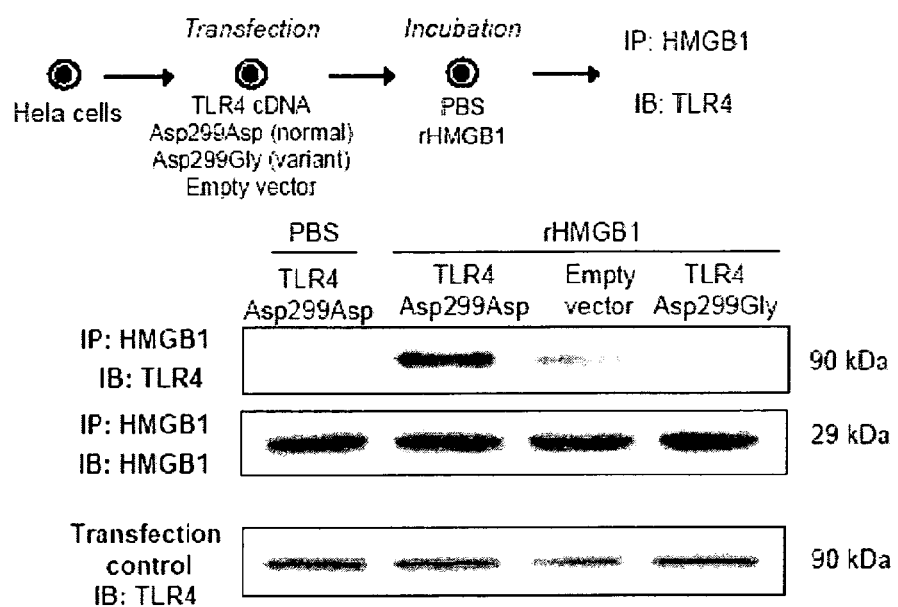
Figure 17B:
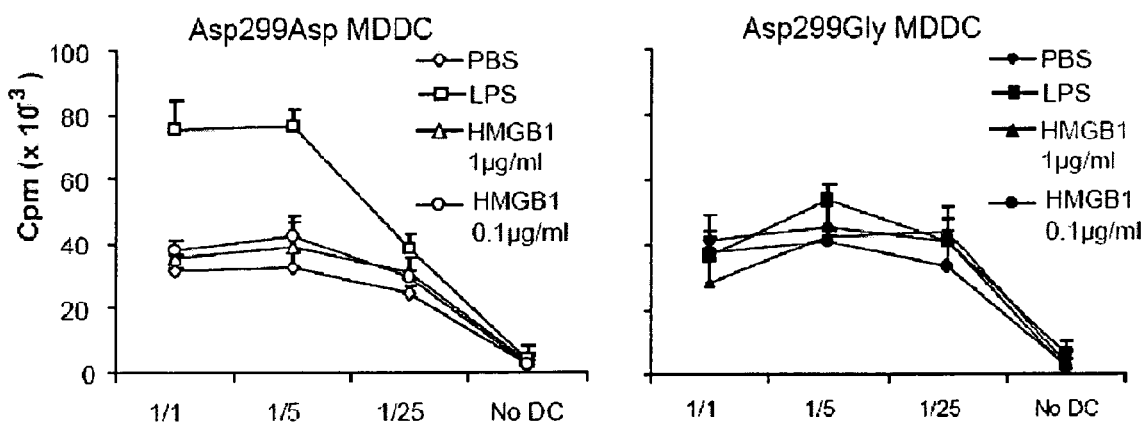

FIG. 17: TLR4 dictates the efficacy of anti-tumor chemotherapy in humans.

A. Defective HMGB1 binding conferred by the TLR4 Asp299Gly mutation. HeLa cells were transfected with empty vector, wild type or mutant TLR4. Then, cells were incubated in the presence of rHMGB1 for one hour and immunoprecipitated.

B. Defective LPS response conferred by the TLR4 Asp299Gly mutation. Human monocyte-derived DC (generated in GM-CSF+IFNα for 3 days) carrying the normal Asp299Asp or the mutated Asp299Gly TLR4 allele were cultured with 2×10$^5$ allogeneic T cells at the indicated ratios in the absence or presence of the indicated doses of rHMGB1 or LPS. T cell proliferation was assessed after 4 days by $^3$H incorporation.

C. Defective capacity of human DCs harboring the TLR4 Asp299Gly mutation to cross-present tumor antigens. Mel96 HLA-A2 negative MART1 positive melanoma tumors cells were treated with oxaliplatinum for 24 hours and were then loaded on human monocyte-derived dendritic cells (MDDC), treated or not with 0.5 µM of chloroquine during coculture. After addition of either control or anti-HMGB1 antibody (10 µg/ml) and the LT12 clone (specific for MART peptide) detection of IFN gamma-producing cells was performed using ELISPOT. The presence of IFN gamma is to be correlated to the activation of LT-12 clone which is itself to be correlated to DC antigen presentation.

DETAILED DESCRIPTION

The invention is based on the observation that cytotoxic agents used in treatment of cancer patients involve the immune system and more specifically the TLR4 signaling pathway. Therefore, the detection of innate or acquired TLR4 dysfunctions is herein disclosed as an adequate way to define the most appropriate treatment to be used on a subject suffering from a cancer, i.e., a treatment allowing restoration or enhancement of the responsiveness of said subject to therapy. Surrogate TLR pathways may be involved in such a treatment (as described further below).

In preclinical models herein described, inventor's data indicates that there is a tendency for tumours to exhibit a faster growth kinetics in their natural progression in TLR4$^{-/-}$ compared with TLR4$^{+/+}$ mice, in particular in colon cancer (see for example FIG. 2A).

Inventors herein demonstrate that tumour progression mediated through dysfunctional TLR4 is independent of exogenous proinflammatory processes intrinsic to their experimental conditions. Indeed, when injecting CT26 cells into mice without adding any procarcinogenic or proinflammatory compound, the growth kinetic of tumour cells was significantly increased in deficient TLR4 hosts compared to immunocompetent littermates (FIG. 2A).

Challenging the current view whereby cytotoxic compounds only act through cell autonomous effects, inventors compared the antitumour effects mediated by an anthracycline, by cis-platinum, by oxali-platinum or by X-Rays (XR) and other pro-apoptotic agents (taxans, mitomycin-C) in immunocompetent versus immunocompromised littermates [lacking T cells or toll like receptors (TLR)]. They discovered that administration of doxycycline (DOX), PLAT or XR to tumour bearing mice selectively promoted long term survival in a T cell -dependent manner through TLR-4 (but not TLR-7, 9). In contrast, taxan or mitomycin C hampered tumour growth independently of immune cells or receptors (see experimental part). Inventors showed that cytotoxic agents were inducing or increasing the expression of TLR4 ligands, such as HMGB1, by tumour cell, rendering the stressed tumour cells accessible to phagocytes, such as DC. Inventors were able to show that TLR4–/– dendritic cells (DC) were unaltered in their capacity to undergo a maturation program or to secrete inflammatory cytokines following interaction with apoptotic cell death. TLR4 was however critical in the antigen processing and presentation rather than in triggering a proinflammatory cascade.

Definitions

In order to facilitate review of the various embodiments, the following descriptions of terms are provided:

The term "cancer" as used herein refers to any type of malignancy (primary or metastases).

Typical cancer are X-rays, anthracycline, cis-platinum and/or oxali-platinum sensitive cancer such as breast, stomach, sarcoma, ovarian, endometrium, bladder, cervix uteri, rectum, colon, lung, ORL cancer, pediatric tumours (neuroblastoma, glyoblastoma multiforme), lymphoma, leukaemia, myeloma, seminoma, Hodgkin's lymphoma and malignant hemopathies.

The term "sensitivity to a treatment" refers to the level of response of a subject to a treatment, including but not limited to the ability to metabolize a therapeutic compound, to the ability to convert a pro-drug to an active drug, to the pharmacokinetics (absorption, distribution, elimination) and to the pharmacodynamics (receptor-related) of a drug in an individual. The treatment may be chemotherapy, including for example administration of an anthracycline, such as doxycycline (DOX), oxali-platinum or cis-platinum, and/or the treatment may be radiotherapy using gamma or X-rays (XR) for example.

The terms "predisposition to a cancer", SIINFEKL "susceptible to developing a cancer", "at risk of developing a cancer" or "having an increase likelihood of having a cancer" as used herein means that a subject has an increased risk of developing a cancer compared to the average population.

The sample to be tested contains nucleic acids and/or polypeptides. Examples of such samples include fluids, tissues, cell samples, organs, biopsies, etc.

The nature of the collected sample is not necessarily correlated to a particular type of cancer. The collected tissue may indeed be a cancerous tissue (preferably frozen rather than paraffin embedded) or a healthy tissue (for example blood, skin, stroma).

The tissue may be collected from a selected cancerous tissue.

The sample may also be obtained for example from a tissue selected from blood, plasma and bone marrow, independently of the optional abnormal or diseased status of said tissue.

Preferably, the sample comprises cells known to express TLR4, preferably cells selected from autologous monocytes, dendritic cells and mononuclear cells.

In a particular example, if the assay is performed to determine whether a subject is susceptible to developing a breast cancer or a colon cancer, a sample of blood, stroma or skin or tumour tissue may be provided.

The invention may be used in various subjects, for example animals, particularly mammals, preferably humans, including adults, children and at the prenatal stage, even more preferably in a subject having a mutated TLR4 nucleic acid or an abnormal TLR4 protein expression or activity.

The term "subject" refers to a patient afflicted with a cancer, or to a subject who may develop a cancer. The patient, in particular the cancer patient, can further be a patient who will undergo an allogeneic bone marrow transplantation.

The term "abnormal" is herein associated with a deviation from normal characteristics. Normal characteristics can be found in a control, a standard for population, etc. For instance, where the abnormal condition is a disease condition such as a cancer, a few appropriate sources of normal characteristics might include an individual who is not suffering from the cancer, a population standard of individuals believed not to be suffering from the cancer, etc.

Likewise, "abnormal" may refer to a condition that is associated with a disease. The term "associated with" includes an increased risk of developing the disease as well as the disease itself. For instance, a certain abnormality (such as an abnormality in a TLR4 nucleic acid or TLR4 protein expression) can be described as being associated with the tendency to develop a cancer.

An abnormal nucleic acid, such as an abnormal TLR4 nucleic acid, is one that is different in some manner to a normal (wild type) nucleic acid. Such abnormality includes but is not necessarily limited to a mutation in the nucleic acid [such as a point mutation (e.g., a single nucleotide polymorphism, also named SNP) or short deletion or duplication of a few to several nucleotides], compared to a control or standard. It will be understood that these types of abnormalities can co-exist in the same nucleic acid or in the same cell or sample. In addition, it is understood that an abnormality in a nucleic acid may cause an abnormality in expression of the corresponding protein. The absence of expression of the corresponding protein is a particular example of such abnormality.

An abnormal TLR4 protein is thus a protein the sequence, configuration, or maturation of which is different from the normal wild-type protein. Preferably the abnormal protein is not functional or only partly functional.

Abnormal protein expression or activity, such as abnormal TLR4 protein expression, refers to expression or activity of a protein that is in some manner different to expression or activity of the protein in a normal (wild type) situation as explained further below, when compared to a control or standard. The term preferably includes the expression of an abnormal TLR4 protein, but also encompasses the abnormal expression of a normal TLR4 protein, due for example to an abnormal transcription of the mRNA encoding a normal TLR4 protein (such abnormal transcription can be a decreased transcription compared to a control or standard level or amount, induced for example by a cancer treatment or by the cancer itself).

Similarly, the level activity of the TLR4 protein may reflect an abnormal expression of a normal TLR4 protein, or the expression of an abnormal TLR4 protein.

Controls or standards appropriate for comparison to a sample, for the determination of abnormality, include samples believed to be normal as well as laboratory values, even though possibly arbitrarily set, keeping in mind that such values may vary from laboratory to laboratory.

Laboratory standards and values may be set based on a known or determined population value and may be supplied in the format of a graph or table that permits easy comparison of measured, experimentally determined values.

The term abnormal TLR4 protein includes but is not necessarily limited to: (1) a mutation in the protein such that one or more of the amino acid residues is different; (2) a short deletion or addition of one or a few amino acid residues to the sequence of the protein; (3) a longer deletion or addition of amino acid residues, such that an entire protein domain or sub-domain is removed or added; (4) expression of a decreased amount of the functional protein, compared to a control or standard amount; (5) alteration of the cellular localization or targeting of the protein; (6) alteration of the temporally regulated expression of the protein (such that the protein is expressed when it normally would not be, or alternatively is not expressed when it normally would be); and (7) alteration of the localized (. g, organ or tissue specific) expression of the protein (such that the protein is not expressed where it would normally be expressed or is expressed where it normally would not be expressed), each compared to a control or standard.

The term "TLR4 protein activity" encompasses any direct binding of TLR4 to one of its naturally occurring ligand, any indirect binding mediated or favoured by TLR4, as well as the effects of said direct or indirect bindings notably on the downstream effectors of the TLR4 pathway (MyD88 for example).

As used in the present application, the term "TLR4 gene" designates the Toll-like Receptor 4 gene on human chromosome 9q32-q33, as well as variants, analogs and fragments thereof, including alleles thereof (e.g., germline mutations) which are related to susceptibility to cancer. The TLR4 gene may also be referred to as CD284, TOLL, hToll (other designations: homolog of *Drosophila* toll)

Recombinant nucleic acids may be prepared by conventional techniques, including chemical synthesis, genetic engineering, enzymatic techniques, or a combination thereof. Suitable TLR4 gene sequences may be found on gene banks, such as NCBI [see SEQ ID NO: 1 (NM 1385541; GeneID: 7099)]. The corresponding polypeptidic sequence is found under the reference NP 612564 in the NCBI gene Bank.

The term "TLR4 gene" includes any variant, fragment or analog of SEQ ID Nos: 1 or of any coding sequence as identified above.

A specific example of a TLR4 polypeptide comprises all or part of SEQ ID NO: 2 (Ref. NCBI: NP 612564; Ref. swissprot: O00206)

Polymorphisms can be referred to, for instance, by the nucleotide position at which the variation exists (896A/G for example), by the change in amino acid sequence caused by the nucleotide variation (D299G for example), or by a change in some other characteristic of the nucleic acid molecule that is linked to the variation (e.g., an alteration of a secondary structure such as a stem-loop, or an alteration of the binding affinity of the nucleic acid for associated molecules, such as polymerases, RNases, and so forth). By way of example, the polymorphism disclosed herein in the region of the TLR4 gene can be referred to by its location in the TLR4 gene [e.g., based on the numerical position of the variant residue D299G or Asp299Gly (Reference SNP Cluster Report: rs4986790) or T399I (Reference SNP Cluster Report: rs4986791)], based on the numerical position of the variant amino acid D299G in the TLR4 polypeptide, by the effect it has on the secondary structure of the TLR4 mRNA or by the effect it has on the tertiary structure of the TLR4 polypeptide (e.g., an alteration of the binding affinity of the polypeptide for ligands such as HMGB1 or hsp).

Diagnostic Methods

Using the above mentioned observations, inventors now herein provides diagnosis methods based on analyses of the TLR4 gene locus in a subject. Within the context of the present invention, the term 'diagnosis" includes the detection, dosing, comparison, etc., at various stages, including early, pre-symptomatic stages, and late stages in a subject as defined above. Diagnosis typically includes the prognosis, the determination of a predisposition or risk of development, the characterization of a subject, to define most appropriate treatment, etc.

A particular diagnostic method herein disclosed is a method of assessing the sensitivity of a subject to a treatment of cancer, which method comprises detecting the presence of a mutated TLR4 nucleic acid or an abnormal TLR4 protein expression or activity in a sample from the subject. The presence of said mutated TLR4 nucleic acid or abnormal TLR4 protein expression or activity is indeed indicative of a resistance, i.e., a negative or poor response of the subject to said treatment. A negative response may be defined as the absence of an efficacious response. This means the treatment appears non efficient to prevent or treat a cancer. In other words, the cancer itself appears resistant to said treatment. A poor response is a response significantly inferior to the response observed in patients who carry a wild-type TLR4 or express a normal TLR4 protein.

Optionally, said method comprises a previous step of providing a sample, as defined previously, from a subject.

According to the present invention, the treatment towards which the sensitivity of a subject can be assessed is preferably selected from at least one of a chemotherapy, including for example administration of an anthracycline, such as DOX (doxorubicin, Idarubicine, 4 Epirubucine, mitoxanthrone), oxali-platinum, cis-platinum (PLAT), and X-rays (XR).

Diagnostic methods, which analyze and predict sensitivity to a treatment as mentioned above, may be used to determine whether a subject should be treated with a particular treatment drug. For example, if the method indicates a likelihood that a subject will respond positively to an anthracycline, PLAT and/or XR, said treatment(s) may be administered to the individual. Conversely, if the method indicates that an individual is likely to respond negatively to said treatment, an alternative course of treatment may be prescribed.

Inventors further herein provides diagnostic methods of determining a predisposition to a cancer or an increased likelihood of having a cancer in a subject, the method comprising detecting the presence of a mutated TLR4 nucleic acid or an abnormal TLR4 protein expression or activity in a sample from the subject.

The TLR4 mutation may be determined in the TLR4 genomic sequence or in the RNA.

The detected mutation may be an innate or acquired mutation.

The mutation in the TLR4 gene locus may be any form of mutation(s), deletion(s), rearrangement(s) and/or insertions in the coding and/or non-coding region of the locus, alone or in various combination(s). Mutations more specifically include point mutations. Deletions may encompass any region of one, two or more residues in a coding or non-coding portion of the gene locus, such as from one residue up to the entire gene or locus. Typical deletions affect smaller regions, such as domains (introns) or repeated sequences or fragments of less than about 20 consecutive base pairs, although larger deletions may occur as well. Insertions may encompass the addition of one or several residues in a coding or non-coding portion of the gene locus. Insertions may typically comprise an addition of between 1 and 20 base pairs in the gene locus. Rearrangement includes inversion of sequences. The TLR4 gene locus mutation may result in the creation of stop codons, frameshift mutations, amino acid substitutions, particular RNA splicing or processing, product instability, truncated polypeptide production, etc. The alteration may result in the production of a TLR4 polypeptide with altered function, stability, targeting or structure. The alteration may also cause a reduction in protein expression or, alternatively, an increase in said production.

In a particular embodiment of the method according to the present invention, the alteration in the TLR4 gene is selected from a point mutation, a deletion and an insertion in the TLR4 gene or corresponding expression product, more preferably a point mutation, even more preferably a single nucleotide polymorphism (SNP).

The present invention in particular now discloses a mutated TLR4 nucleic acid comprising a point mutation, preferably the wild type sequence of TLR4 (preferably of human TLR4) comprising a point mutation, preferably a single nucleotide polymorphism (SNP) leading to the substitution of asparagine by glycine at position 299.

A particular method according to the present invention thus comprises detecting the presence of a mutated TLR4 sequence comprising a point mutation, preferably a single nucleotide polymorphism (SNP) leading to the substitution of asparagine by glycine at position 299 or to the substitution of threonine by isoleucine at position 399 in a sample from the subject.

A particular example of a mutated TLR4 human nucleic acid sequence comprises a TLR4 sequence comprising D299G Polymorphism (Reference SNP Cluster Report: rs4986790) or a TLR4 sequence comprising T399I Polymorphism (Reference SNP Cluster Report: rs4986791).

The methods herein described may further comprise a step the aim of which is to determine whether the subject is homozygous or heterozygous for the polymorphism.

In the methods of this invention, any mutation or alteration in the TLR4 gene may be assessed in combination with other markers such as other mutations or alterations in any other gene or protein.

The presence of a mutated TLR4 in the sample can be detected through the genotyping of the sample. The detection can be performed by sequencing all or part of the TLR4 gene, using selective hybridization and/or amplification of all or part of the TLR4 gene. More preferably a TLR4 gene specific amplification is carried out before the mutation identification step.

In a particular embodiment herein described, the presence of a mutated TLR4 nucleic acid is detected by using restriction digestion, sequencing, selective hybridization and/or selective amplification.

A specific embodiment comprises the detection of the presence of at least one SNP in the TLR4 gene sequence of a subject.

In another embodiment, the method comprises detecting the presence of an abnormal TLR4 RNA expression. Abnormal RNA expression includes the presence of a mutated RNA sequence, the presence of an abnormal RNA splicing or processing, the presence of an abnormal quantity of RNA, etc. These may be detected by various techniques known in the art, including restriction digestion, sequencing of all or part of the TLR4 RNA or selective hybridization or selective amplification of all or part of said RNA, for instance.

In a further embodiment, the method comprises detecting the presence of an abnormal TLR4 polypeptide or protein expression. Abnormal TLR4 polypeptide or protein expression includes the presence of a mutated polypeptide sequence, the presence of an abnormal quantity of TLR4 polypeptide, the presence of an abnormal tissue distribution, etc. These may be detected by various techniques known in the art, including by sequencing and/or binding to specific ligands (such as antibodies), for instance.

Other suitable methods may be used to detect or quantify abnormal TLR4 gene or RNA expression or sequence. They include allele-specific oligonucleotide (ASO), allele-specific amplification, Southern blot (for DNAs), Northern blot (for RNAs), single-stranded conformation analysis (SSCA), PFGE, fluorescent in situ hybridization (FISH), gel migration, clamped denaturing gel electrophoresis, heteroduplex analysis, RNase protection, chemical mismatch cleavage, ELISA, radio-immunoassays (RIA) and immuno-enzymatic assays (IEMA).

As explained previously, in a particular embodiment, the method comprises detecting or determining the presence of an abnormal TLR4 nucleic acid in a sample from the subject. This can be accomplished as explained previously by using restriction digestion, sequencing, selective hybridization and/or selective amplification of nucleic acids present in said sample.

Restriction digestion can be carried out using techniques and enzymes well known in the art.

Sequencing can be carried out using techniques well known in the art, using automatic sequencers. The sequencing may be performed on the complete TLR4 gene or, more preferably, on specific domains thereof, typically those known or suspected to carry deleterious mutations or other alterations.

Examples of specific primers amplifying the region comprising the Asp299Gly polymorphism (A896G) are herein provided:

(SEQ ID NO: 4)
TLR4_Forward 5' GATTAGCATACTTAGACTACTACCTCCATG 3', (SEQ ID NO: 5)
TLR4_Reverse 5' TGTGGGAAACGTTCCAAATTTACA 3'.

These sequences may be used to amplify a fragment of 86bp

Another example of primer set (which can be used to amplify a 101 bp fragment) is provided in the experimental part of the present application.

Another mutation involved in ligand binding is Thr399Ile.

Examples of specific primers amplifying the region comprising the Thr399Ile polymorphism (C1196T) are further herein provided:

(SEQ ID NO: 6)
TLR4_forward 5'-TGAGTTTCAAAGGTTGCTGTTCTC-3', (SEQ ID NO: 7)
TLR4_reverse 5'-AGGAATACTGAAAACTCACTCATTTGTT-3'.

These sequences may be used to amplify a fragment of 178 bp.

Thr399Ile ASO are 5'-[6-FAM]-TTAGGCTGGTTGTCC-[MGB][NFQ]-3' (SEQ ID NO: 8) and 5'-[VIC™]-TTAG-GCTGATTGTCC-[MGB][NFQ]-3' (SEQ ID NO: 9), respectively.

Amplification is based on the formation of specific hybrids between complementary nucleic acid sequences that serve to initiate nucleic acid reproduction.

Amplification may be performed according to various techniques known in the art, such as by polymerase chain reaction (PCR), ligase chain reaction (LCR), strand displacement amplification (SDA), nucleic acid sequence based amplification (NASBA) and Restriction fragment length polymorphism (RFLP).

These techniques can be performed using commercially available reagents and protocols. Preferred techniques use allele-specific PCR or PCR-SSCP. Amplification usually requires the use of specific nucleic acid primers, to initiate the reaction.

Nucleic acid primers useful for amplifying sequences from the TLR4 gene or locus are able to specifically hybridize with a portion of the TLR4 gene locus that flank a target region of said locus, said target region being mutated in certain subjects having a cancer or at risk of developing a cancer.

Primers that can be used to amplify TLR4 target region may be designed based on the genomic or RNA sequence of TLR4 and, in particular, on the sequence of SEQ ID NO: 1 (NM 138554; GeneID: 7099).

Another particular object of this invention resides in a nucleic acid primer useful for amplifying sequences from the TLR4 gene or locus including surrounding regions. Such primers are preferably complementary to, and hybridize specifically to nucleic acid sequences in the TLR4 gene locus. Particular primers are able to specifically hybridize with a portion of the TLR4 gene locus that flank a target region of said locus, said target region being altered in certain subjects having a cancer, a predisposition to a cancer or an increase likelihood of having a cancer.

The invention also relates to a nucleic acid primer, said primer being complementary to and hybridizing specifically to a portion of a TLR4 coding sequence (e.g., gene or RNA) mutated in certain subjects having a cancer, a predisposition to a cancer or an increase likelihood of having a cancer. In this regard, particular primers of this invention are specific for mutated sequences in a TLR4 gene or RNA. By using such primers, the detection of an amplification product indicates the presence of a mutation in the TLR4 gene locus. In contrast, the absence of amplification product indicates that the specific mutation is not present in the sample.

A typical nucleic acid primer usable in the methods herein disclosed is a primer that is complementary to and that hybridizes specifically to a mutated TLR4 sequence comprising a point mutation, typically a wild type TLR4 sequence comprising a point mutation, preferably a single nucleotide polymorphism (SNP) leading to the substitution of asparagine by glycine at position 299 or to the substitution of threonine by isoleucine at position 399.

Particular primers usable for the Asp299Gly polymorphism in the herein disclosed methods comprises all or a distinctive part of a sequence selected for example from TLR4_Forward 5' GATTAGCATACTTAGACTACTAC-CTCCATG 3' (SEQ ID NO: 10), TLR4_Reverse 5' TGTGG-GAAACGTTCCAAATTTACA 3' (SEQ ID NO: 11) or from forward 5'-CCATTGAAGAATTCCGATTAGCATA-3' (SEQ ID NO: 12) and reverse 5'-CACTCACCAGGGAAAAT-GAAGAA-3' (SEQ ID NO: 13). Particular primers usable for the Thr399Ile polymorphism in the herein disclosed methods comprises all or a distinctive part of a sequence selected for example from TLR4_forward 5'-TGAGTTTCAAAGGT-TGCTGTTCTC-3' (SEQ ID NO: 14), TLR4_reverse 5'-AG-GAATACTGAAAACTCACTCATTTGTT-3' (SEQ ID NO: 15).

Hybridization detection methods are based on the formation of specific hybrids between complementary nucleic acid sequences that serve to detect nucleic acid sequence mutation(s).

A particular detection technique involves the use of a nucleic acid probe specific for wild-type or mutated TLR4 gene or RNA, followed by the detection of the presence of an hybrid. The probe may be in suspension or immobilized on a substrate or support (as in nucleic acid array technologies). The probe is typically labelled to facilitate detection of hybrids.

Typical hybridization detection methods comprises the following steps of contacting the sample from the subject with a nucleic acid probe specific for a mutated TLR4 nucleic acid (preferably gene locus), and assessing the formation of an hybrid. In a particularly preferred embodiment, the method comprises contacting simultaneously the sample with a set of probes that are specific, respectively, for wild type TLR4 gene locus and for various mutated forms thereof. In this embodiment, it is possible to detect directly the presence of various forms of mutations in the TLR4 gene locus in the sample. Also, various samples from various subjects may be treated in parallel.

A particular method herein disclosed comprises the steps of assessing the sensitivity of a subject to a treatment of a cancer, in particular to a chemotherapeutic treatment, comprising (a) obtaining from the subject a test sample of DNA comprising a TLR4 sequence, (b) contacting the test sample with at least one nucleic acid probe, wherein said nucleic acid is complementary to and specifically hybridizes with a mutated TLR4 sequence to form a hybridization sample, (c) maintaining the hybridization sample under conditions sufficient for the specific hybridization of the TLR4 sequence with the nucleic acid probe to occur, and (d) detecting whether there is specific hybridization of the TLR4 sequence with the nucleic acid probe. The specific hybridization of the TLR4 sequence with the nucleic acid probe indeed identifies the cancer as resistant to said treatment in the subject.

Preferably the mutated TLR4 sequence is associated with resistance to a treatment. Said treatment is preferably selected from a chemotherapy, for example including administration of an anthracycline, such as DOX, and/or oxali-platinum or cis-platinum (PLAT), and a radiotherapy preferably including X-rays (XR). The treatment can further comprise a chemotherapy combined to a radiotherapy.

A method of detecting or determining a predisposition to a cancer or an increased likelihood of having a cancer in a subject is also herein disclosed. Said method comprises the following steps of (a) obtaining from the subject a test sample of DNA comprising a TLR4 sequence, (b) contacting the test sample with at least one nucleic acid probe, wherein said nucleic acid is complementary to and specifically hybridizes with a mutated TLR4 sequence to form a hybridization sample, (c) maintaining the hybridization sample under conditions sufficient for specific hybridization of the TLR4 sequence with the nucleic acid probe, and (d) detecting whether there is specific hybridization of the TLR4 sequence with the nucleic acid probe. Specific hybridization of the TLR4 sequence with the nucleic acid probe indeed indicates a predisposition to cancer or an increased likelihood of having a cancer in the subject.

Typical stringent hybridization conditions include temperatures above 30° C., preferably above 35° C., more preferably in excess of 42° C., and/or salinity of less than about 500 mM, preferably less than 200 mM. Hybridization conditions may be adjusted by the skilled person by modifying the temperature, salinity and/or the concentration of other reagents such as SDS, SSC, etc.

For purposes of the present disclosure, "stringent conditions" encompass conditions under which hybridization will only occur if there is less than 25% mismatch between the hybridization molecule and the target sequence.

In a preferred embodiment, the mutated TLR4 sequence comprises a point mutation, preferably a point mutation selected from a single nucleotide polymorphism (SNP) leading to a substitution of asparagine by glycine at position 299 and a single nucleotide polymorphism (SNP) leading to a substitution of threonine by isoleucine at position 399.

Within the context of this invention, a probe refers to a polynucleotide sequence which is complementary to and capable of specific hybridization with a (target portion of a) TLR4 gene or RNA, and which is suitable for detecting polynucleotide polymorphisms associated with TLR4 alleles, in particular with a polymorphism leading to the substitution of asparagine by glycine at position 299 or to the substitution of threonine by isoleucine at position 399, which predispose to or are associated with cancer. Probes are preferably perfectly complementary to the TLR4 gene, RNA, or target portion thereof. Probes typically comprise single-stranded nucleic acids of between 25 to 100 nucleotides in length, preferably of between 20 and 50 nucleotides in length. It should be understood that longer probes may be used as well. A preferred probe of this invention is a single stranded nucleic acid molecule of between 25 to 30 nucleotides in length, which can specifically hybridize to a region of a TLR4 nucleic acid (for example gene or RNA) that carries an alteration.

Nucleic acid probe specific for an abnormal (e.g., a mutated) TLR4 sequence (gene or RNA in particular), i.e., a nucleic acid probe that specifically hybridizes to said abnormal TLR4 sequence and essentially does not hybridize to a normal (reference) TLR4 sequence, are herein described. Specificity indicates that hybridization to the target sequence generates a specific signal which can be distinguished from the signal generated through non-specific hybridization. Perfectly complementary sequences are preferred to design probes according to this invention. It should be understood, however, that certain mismatch may be tolerated, as long as the specific signal may be distinguished from non-specific hybridization.

The sequence of the probe can be readily prepared based on any sequences of the TLR4 gene or RNA carrying a mutation, in particular a point mutation such as a SNP, linked to the sensitivity of a subject to a treatment of cancer, to the presence of a cancer, to a predisposition to a cancer or an increase likelihood of having a cancer.

It is also appropriate to generate probes and primers based on fragments or portions of these nucleic acid molecules, for instance regions that encompass the identified polymorphism at nucleotide 896 (A896G) and at nucleotide 1196 (C1196T) in the TLR4 sequence.

A typical mutated TLR4 sequence indeed usable in the methods herein described comprises the wild type sequence of TLR4 and a point mutation, preferably a single nucleotide polymorphism (SNP) leading to the substitution of asparagine by glycine at position 299 or to the substitution of threonine by isoleucine at position 399.

A particular probe herein described comprises all or a distinctive part of a TLR4 sequence comprising D299G Polymorphism (Reference SNP Cluster Report: rs4986790) or all or a distinctive part of a TLR4 sequence comprising T399I Polymorphism (Reference SNP Cluster Report: rs4986791).

Nucleotide substitutions may be performed, as well as chemical modifications of the probe. Such chemical modifications may be accomplished to increase the stability of hybrids (e.g., intercalating groups) or to label the probe. Typical examples of labels include, without limitation, radioactive isotopes, enzyme substrates, cofactors, ligands, chemiluminescent or fluorescent agents, haptens, and enzymes. Methods for labelling and guidance in the choice of labels appropriate for various purposes are discussed, e.g., in Sambrook et al. (In Molecular Cloning. A Laboratory Manual, CSHL, New York, 1989) and Ausubel et al. (In Current Protocols in Molecular Biology, John Wiley & Sons, New York, 1998).

Inventors herein describe the use of a nucleic acid probe or primers as described above in a method of assessing the sensitivity of a subject to a treatment of cancer, in particular to a chemotherapeutic treatment, or in a method of detecting or determining a predisposition to a cancer or an increase likelihood of having a cancer in a subject.

The methods disclosed herein of assessing the sensitivity of a subject to a treatment of cancer, in particular to a chemotherapeutic treatment, or of determining a predisposition to a cancer in a subject may further be performed, as indicated above, by detecting an abnormal TLR4 protein or TLR4 protein expression which may be innate or acquired.

Preferred methods according to the invention comprise the steps of contacting the sample with a ligand identified for binding to a TLR4 protein (a normal TLR4, i.e., a wild-type TLR4, or an abnormal TLR4) and assessing whether a binding occur or not between the subject TLR4 and said TLR4 ligand, for example by determining the formation of a complex between said subject TLR4 and said TLR4 ligand.

A ligand is an agent that specifically binds to a defined target.

The term "specifically" means that less than 10%, preferably less than 5% of the agent bind a target different from said defined target. Thus, a TLR4 protein-specific ligand binds substantially only the TLR4 protein. Different types of ligands may be used, such as specific antibodies and other agents (and functional fragments thereof) that bind substantially only to the TLR4 protein.

A preferred ligand herein disclosed is a ligand identified for specifically binding to an abnormal TLR4 protein or polypeptide.

Anti-TLR4 protein antibodies may be produced using standard procedures described in a number of texts, including Harlow and Lane (Antibodies, A Laboratory Manual, CSHL, New York, 1988). The determination that a particular ligand binds substantially only to the TLR4 protein may readily be made by using or adapting routine procedures. One suitable in vitro assay makes use of the Western blotting procedure (described in many standard texts, including Harlow and Lane (Antibodies, A Laboratory Manual, CSHL, New York, 1988)). Western blotting may be used to determine that a given TLR4 protein binding agent, such as an anti-TLR4 protein monoclonal antibody, binds substantially only to the TLR4 protein.

Within the context of this invention, an antibody designates a polyclonal antibody, a monoclonal antibody, as well as fragments or derivatives thereof having substantially the same antigen specificity.

Shorter fragments of antibodies can also serve as specific binding agents. For instance, FAbs, Fvs, and single-chain Fvs (SCFvs) that bind to TLR4 would be TLR4-specific binding ligands.

These antibody fragments are defined as follows: (1) FAb, the fragment which contains a monovalent antigen-binding fragment of an antibody molecule produced by digestion of whole antibody with the enzyme papain to yield an intact light chain and a portion of one heavy chain; (2) FAb', the fragment of an antibody molecule obtained by treating whole antibody with pepsin, followed by reduction, to yield an intact light chain and a portion of the heavy chain; two FAb' fragments are obtained per antibody molecule; (3) (FAb') 2, the fragment of the antibody obtained by treating whole antibody with the enzyme pepsin without subsequent reduction; (4) F (Ab') 2, a dimer of two FAb' fragments held together by two disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule. Methods of making these fragments are routine.

A particular antibody herein presented is specific for an abnormal TLR4 protein or polypeptide, typically a mutated TLR4 polypeptide, as defined previously and as herein exemplified. Preferably the antibody comprises all or a distinctive part of a sequence selected from the extracellular domain of TLR4. The TLR4 extracellular domain is depicted in SEQ ID NO: 3.

Another particular antibody usable in the present invention is specific for a wild-type TLR4 polypeptide.

Thus, in a specific embodiment, the sample is contacted with an antibody specific for an abnormal TLR4 protein or polypeptide and the formation of an immune complex is determined. Various methods for detecting an immune complex can be used, such as ELISA, radio-immunoassays (RIA) and immuno-enzymatic assays (IEMA).

Other ligands identified for binding to TLR4 may be selected for example from (i) a TLR4 ligand induced on tumour cells by an anthracycline, by cis-platinum, oxali-platinum or by X Rays, (ii) a DOX or PLAT or X-Rays—apoptotic cell and (iii) the lipopolysaccharide from Gram negative bacteria (LPS).

Ligand induced on tumour cells by an anthracycline, by oxali-platinum, by cis-platinum or by X-Rays may be detected on the surface a tumour cell using, in particular, a probe selected from a TLR4Fc (anti-TLR4 antibody Fc fragment), a TLR4Ig (anti-TLR4 immunoglobulin) and an anti-HMGB1 antibody. The probe is preferably tagged. This test preferably includes allogenic dendritic cells to enhance the secretion of said TLR4 ligand.

In a particular embodiment, the present invention thus herein discloses a method for detecting the lack of immunogenicity of the tumour cells via TLR4 pathway, said method comprising contacting autologous tumour cells which have been treated with an anthracycline, cis-platinum, oxali-platinum or X-rays and which express a TLR4 ligand, a TLR4Fc (anti-TLR4 antibody Fc fragment), or a TLR4Ig (anti-TLR4 immunoglobulin), the absence of binding of said TLR4Fc or TLR4Ig being correlated to the lack of immunogenicity of the tumour cell.

Techniques well known from the man of the art such as ELISA binding assay or Western Blot (WB) may be applied in the above described methods.

Although non-specific binding may occur, binding to the target TLR4 polypeptide occurs with a higher affinity and can be reliably discriminated from non-specific binding.

Contacting between the nucleic acids or polypeptides of the sample and the ligand or the probe previously described may be performed in any suitable device, such as a plate, tube, well, glass, etc. In specific embodiments, the contacting is performed on a nucleic acid array or on a specific probe or ligand array, such as a nucleic acid probe present on a nucleotide array.

Examples of known ligands are HMGB1, GMP, LPS, hyaluronan, fibrinogen, fibronectin, hsp 60 or hsp 70, which are usable in a pharmaceutical composition according to the invention. They are particularly useful for treating or preventing a cancer in a subject having a normal or non mutated TLR4 nucleic acid or a normal TLR4 protein expression or activity but no induction of TLR4 ligands following treatment with anthracyclines, cis-platinum, oxali-platinum or X-rays.

The present invention further discloses a method comprising determination of the abnormal TLR4 activity by detecting an abnormal cross-presentation of allogeneic tumour cells, in particular melanoma cells, by subject autologous dendritic cells (DC), to a cytotoxic T lymphocytes clone (CTL).

The allogeneic tumour or cancer cell may be for example an anthracycline, cis-platinum, oxali-platinum or X-rays treated tumour cell. In a particular example the allogeneic tumour cell is an apoptotic body.

The ligand, just like the probe previously described, may be in suspension or immobilized on a substrate or support.

The substrate may be a solid or semi-solid substrate such as any support comprising glass, plastic, nylon, paper, metal, polymers and the like. The substrate may be of various forms and sizes, such as a slide, a membrane, a bead, a column, a gel, etc.

The contacting may be made under any condition suitable for a complex to be formed between the reagent (ligand or probe) and the nucleic acids or polypeptides of the sample.

The sample may thus be contacted simultaneously, or in parallel, or sequentially, with various ligands or probes specific for different forms of a TLR4 nucleic acid or polypeptide, such as a wild-type and various abnormal forms thereof.

TLR4 is mainly expressed in myeloid cells in vivo [for example, monocytes, dendritic cells (DC)]. TLR4 signaling is critical for triggering secretion of pro-inflammatory cytokines (IL-1b, IL-6, TNFα and IL-12 for example) and accelerating DC maturation.

In the present application, the abnormal TLR4 expression or activity may thus also be correlated to the absence or presence of a secretion of, or to an alteration in the cellular level of a compound selected, for example, from IL-6, TNFα, IL-1b, IL-2 or IL-12p40, Rantes, IP-10 and MIP1a. Such cellular level of IL-6, TNFα, IL-1b, IL-2 or IL-12p40 may be measured in the methods herein disclosed by inventors. Such a measure may further be compared to a normal level. The measured level is preferably compared to a reference level measured from a culture comprising (i) monocytes and/or dendritic cells (DC) and (ii) a TLR4 ligand, preferably HMGB1.

The abnormal TLR4 expression or activity may also be correlated to an abnormal transcription of normal TLR4. The abnormal transcription can be an increased expression compared to a control or standard amount or level. It can also be a decreased expression compared to a control or standard amount or level, for example induced by a cancer treatment or by the cancer itself.

The present invention provides a method comprising determining the abnormal TLR4 protein expression by measuring the cellular level of mRNA encoding a normal TLR4, wherein a decreased level compared to a control or standard level is correlated to an abnormal TLR4 protein expression. The mRNA level may be measured, ex vivo or in vitro, on patient isolated monocytes or dendritic cells.

Such a method can include a step comprising the use of RT-PCR (Reverse Transcription-Polymerase Chain Transcription).

An abnormal TLR4 expression or activity may further be detected by measuring the cellular level of IFNγ (derived from NK cells) in a coculture comprising dendritic cells (DC) and natural killer (NK) cells. DC are autologous cells from the subject to be tested. NK cells may be autologous or allogeneic. The coculture may be performed, in parallel, in the presence of at least one TLR4 ligand, and in the absence of any TLR4 ligand.

The subject IFNγ measured level is further compared to a reference level. Inventors indeed discovered that an abnormal IFNγ level (decreased value compared to known standards) or the absence of IFNγ is correlated to an abnormal TLR4 expression.

Interleukines and IFNγ secretion may be determined by techniques well known in the art, such as ELISA or intracellular cytokine staining in flow cytometry.

The abnormal TLR4 expression or activity may also be detected by measuring the endosomal pH of phagocytes displaying or not the TLR4 mutation. Said pH may further be compared to a normal pH. An abnormal pH is correlated to an abnormal TLR4 expression. A pH inferior to 7, preferably inferior to 6, 5 or 4, is correlated to an abnormal TLR4 activity.

Without wishing to be bound by any particular theory, the inventors believe that the mechanisms by which TLR4 might affect responsiveness to anthracycline/oxali-platinum/cis-platinum/XR likely involve bone marrow precursors, namely dendritic cells (DC). Indeed, TLR4−/− bone marrow DC pulsed with DOX-induced apoptotic tumour cells cannot prime naïve T cells in TLR4−/− mice while TLR4+/+ DC counterparts can do so. However, T cell priming deficiencies promoted by TLR4 dysfunction do not imply uptake or maturation processes but rather antigen routing and degradation within DC endosomal compartments. Therefore, TLR4 controls the efficacy of immunogenic apoptosis triggered by chemo- or radio-therapy in cancer bearing-hosts.

Inventors thus herein provide a method comprising determining the abnormal TLR4 activity by detecting an abnormal cross presentation of allogeneic tumour cells, by subject autologous dendritic cells (DC), to a cytotoxic lymphocytes clone (CTL) or to a CD4+ T cell clone, preferably respectively in an MHC class I or class II dependent fashion.

In a particular example, HLA-A*02 expressing DC can for example be pulsed with X-rays-induced allogeneic melanoma tumour cell line (HLA-A2 negative) containing MelanA/Mart1 antigens. Such DC could be incubated with an HLA-A2 restricted Mart1 specific CTL clone which will produce IFNγ if cross presentation do occur in vitro. Whereas in TLR4 wild-type individuals, cross presentation will occur and IFNγ will be measured in EIA, in Asp299Gly TLR4 DC or in Thr399Ile TLR4, cross presentation will fail at any dosage of apoptotic material pulsed onto DC.

Inventors further provide a method comprising determining the abnormal TLR4 activity by detecting the fusing between late endosomes and lysosomes.

This method aims at detecting, in confocal microscopy or electron microscopy, the kinetics of the fusion of endosomal compartments (that comprise phagocytes, engulfed X Ray-apoptotic tumour cells, preferably labelled tumour cells) with lysosomes (for example labelled with anti-LAMP Ab in FITC). The merge will allow a precise quantification of double positive compartments within a cell for example at 15 min, 30 min, 1 hour and 3 hours. In TLR4−/−DC, colocalization of compartments containing dead bodies with lysosomes is significantly accelerated.

The methods described in the present application are thus, as indicated previously, preferably performed on a sample comprising cells expressing TLR4 in normal conditions, preferably selected from autologous monocytes, dendritic cells and mononuclear cells.

Inventors further herein describe a diagnostic method comprising the determination of the TLR4 mutational status of a subject who will undergo a bone marrow transplantation.

A kit for use in a method of assessing the sensitivity of a subject to a treatment of a cancer, in particular to a chemotherapeutic treatment of cancer, as defined previously, or for use in a method of determining predisposition to a cancer in a subject is further herein provided. This kit comprises a nucleic acid probe, as described previously, that specifically hybridizes with an abnormal, preferably mutated, TLR4 sequence, as described previously, that identifies the cancer as resistant to said treatment in the subject, or that is associated with the increased predisposition to cancer or an increased likelihood of having a cancer.

The kit may further comprises a primer and/or a ligand, such as an antibody, as described previously. The kit may also comprise reagents and/or a protocol for performing a hybridization, amplification or an antigen-antibody immune reaction.

The methods herein described may be performed in vivo, in vitro or ex vivo. They are preferably performed in vitro or ex vivo.

Screening Methods

The present application also provides novel methods for screening compounds, preferably drug candidates or leads, for preventing or treating a cancer in a subject having a mutated TLR4 nucleic acid or an abnormal TLR4 protein expression or activity, comprising determining the ability of a test compound to modulate the expression or activity of TLR4.

Preferred test compounds screened using a method as described above are capable of restoring or enhancing a functional expression of a mutated or abnormal TLR4.

The screening methods herein disclosed preferably use TLR4 nucleic acid or polypeptide as well as molecules bypassing TLR4 signaling pathway and leading to NF-κB activation, as new targets. The methods include binding assays and/or functional assays, and may be performed in vitro, in cell systems, in animals, etc.

The Inventors in particular disclose a method of selecting a biologically active compound, more particularly a compound active in the prevention or treatment of cancer, said method comprising contacting in vitro a test compound with a product selected from a TLR4 nucleic acid (gene or RNA for example), a TLR4 polypeptide, a molecule bypassing TLR4 signaling pathway and leading to NF-κB activation, and a fragment thereof and determining the ability of said test compound to bind said product.

In a further particular embodiment, the method comprises contacting a recombinant host cell expressing a TLR4 polypeptide according to the present invention or a molecule bypassing TLR4 signaling pathway and leading to NF-κB activation, with a test compound, and determining the ability of said test compound to bind respectively said TLR4 polypeptide or said molecule bypassing TLR4 signaling pathway and to modulate its activity.

In a particular embodiment, said TLR4 polypeptide or fragment thereof is an abnormal, preferably mutated, TLR4 polypeptide or fragment thereof responsible of the TLR4 abnormal status or comprising the mutation(s).

Binding to said nucleic acid, polypeptide or molecule provides an indication as to the ability of the test compound to modulate the activity of said target, and thus to affect a pathway leading to a cancer in a subject.

The determination of binding may be performed by various techniques known from the man of the art, some of which were herein described previously, such as by labelling of the test compound, by competition with a labelled control or reference ligand known or identified for binding to a particular TLR4 protein or polypeptide (wild-type or abnormal TLR4), etc.

A further object herein described resides in a method of selecting biologically active compounds, more particularly compounds active in the prevention or treatment of cancer in a subject having a mutated TLR4 nucleic acid or an abnormal TLR4 protein expression or activity, said method comprising contacting in vitro a test compound with a TLR4 gene according to the present invention and determining the ability of said test compound to modulate the expression of said TLR4 gene.

Another method of selecting such a biologically active compound is further provided wherein said method comprises the steps of contacting in vitro a test compound with a TLR4 polypeptide or a molecule bypassing TLR4 signaling pathway and leading to NF-κB activation, and determining the ability of said test compound to respectively modulate the activity of said TLR4 polypeptide or of said molecule bypassing the TLR4 signaling pathway.

A particular TLR4 gene, polypeptide or fragment thereof usable in a method as presently disclosed is a mutated TLR4 gene, polypeptide or fragment thereof as described previously in the present application, preferably comprising a mutation leading to the substitution of asparagine by glycine at position 299 of the TLR4 polypeptide and/or a mutation leading to the substitution of threonine by isoleucine at position 399 of the TLR4 polypeptide.

A particular molecule bypassing TLR4 signaling pathway and leading to NF-κB activation usable in a method as presently disclosed may be selected from TLR3 and/or TLR9 ligands, such as double stranded RNA (for example Poly A:U and Poly I:C) and/or hypomethylated C and G enriched oligonucleotides (CpG oligonucleotides).

Another particular object of this invention resides in a method of selecting compounds active in the prevention or treatment of cancer in a subject having a mutated TLR4 nucleic acid or an abnormal TLR4 protein expression or activity, said method comprising contacting in vitro a test compound with a polypeptide involved in the regulation of the activity of TLR4, preferably a MyD88 or TRIF polypeptide, even more preferably a MyD88 polypeptide, or binding site-containing fragment thereof and determining the ability of said test compound to bind said polypeptide or fragment thereof.

In a further particular embodiment, the method comprises contacting a recombinant host cell expressing a polypeptide involved in the regulation of the activity of TLR4, preferably a MyD88 or TRIF polypeptide, even more preferably a MyD88 polypeptide, with a test compound, and determining the ability of said test compound to bind said polypeptide and to modulate the activity of said polypeptide.

A further method herein discloses comprises the steps of selecting biologically active compounds, more particularly compounds active in the prevention or treatment of cancer in a subject having a mutated TLR4 nucleic acid or an abnormal TLR4 protein expression or activity, said method comprising contacting in vitro a test compound with a gene involved in the regulation of the activity of TLR4, preferably a MyD88 or TRIF encoding gene, even more preferably a MyD88 encoding gene, and determining the ability of said test compound to modulate the expression of said gene.

In a particular embodiment of the methods of screening, the modulation is an activation. In an other particular embodiment of the methods of screening, the modulation is an inhibition.

The method of the present invention is suitable for screening many compounds. These compounds may be of various origin, nature and composition. A test compound may be any organic or inorganic substance, such as a lipid, peptide, polypeptide, nucleic acid, small molecule, etc., in isolated or in mixture with other substances. The compounds may be all or part of a combinatorial library of products, for instance.

Ligand induced on tumour cells by an anthracycline, by PLAT or by X-Rays may be screened on a tumour cell culture using a probe selected in particular from a TLR4Fc, a TLR4Ig and an anti-HMGB1 antibody. The probe is preferentially tagged.

In a particular embodiment, the present invention also discloses a method for screening a compound useful for treating a cancer in a subject having a mutated TLR4 nucleic acid or an abnormal TLR4 protein expression or activity, said method comprising determining the ability of a test compound to induce or increase in vitro, in vivo or ex vivo the expression or activity of a ligand of TLR4.

TLR4 ligands have been shown to upregulate TLR4 expression. Inventors have further demonstrated that TLR4 ligands are able to increase the sensitivity of a subject to chemotherapy or radiotherapy, in particular to chemotherapy.

Such compounds may be detected using confocal microscopy. Indeed, endogenous TLR4 ligands have been shown by inventors to be translocated from the nucleus to the tumour cell plasma membrane within 1 to 30 minutes following the administration of a chemotherapy or of a radiotherapy.

Preferred ligands, herein identified, that may be used to upregulate TLR4 expression and/or to increase the sensitivity of a subject to chemotherapy and/or radiotherapy are HMGB1 and LPS.

The above screening methods may be performed in any suitable device, such as plates, for example multi-well plates, tubes, dishes, flasks, etc. Several test compounds can be assayed in parallel.

The substances obtained by the described screening method can be used to prepare pharmaceutical compositions for the treatment or prevention of cancer in particular in a subject having a mutated TLR4 nucleic acid or an abnormal TLR4 protein expression or activity.

The substances obtained by the described screening method can also be used to prepare pharmaceutical compositions to enhance the sensitivity of a subject, in particular of a subject having a mutated TLR4 nucleic acid or an abnormal TLR4 protein expression or activity, to chemotherapy and/or radiotherapy (using X-Rays for example), in particular of a subject who will undergo a bone marrow transplantation, more particularly an allogeneic bone marrow transplantation.

The use of a biologically active compound, known or isolated with a screening method as previously described, capable of restoring or enhancing, i.e., increasing or favouring, a functional TLR4 expression to prepare a pharmaceutical composition for treating or preventing a cancer in a subject, is in particular herein provided. The subject is preferably one having a mutated TLR4 nucleic acid or an abnormal TLR4 protein expression or activity as explained before.

The present invention encompasses any known compound and any compound identified using a screening method according to he invention capable of restoring a functional TLR4 expression, and any pharmaceutical composition comprising such a compound, to prevent or treat a cancer in a subject, in particular in a subject having a mutated TLR4 nucleic acid or an abnormal TLR4 protein expression or activity.

The pharmaceutical compositions herein provided may further advantageously comprise at least one compound selected from anthracycline, such as DOX, oxali-platinum and/or cis-platinum (PLAT), as a combined preparation, for simultaneous, separate or sequential use, in the prevention or treatment of said cancer.

In a preferred embodiment, pharmaceutical compositions herein described, in particular pharmaceutical compositions which do not comprise a chemotherapeutic product, are administered before any treatment comprising the administration of a chemotherapy or radiotherapy, in TLR4 mutated individuals. The administration of the pharmaceutical composition(s) may be performed in a single administration or in repeated administrations, before and/or during any subsequent treatment, for example one day before any subsequent treatment and every 3 weeks during said treatment.

In another example, the administration of the pharmaceutical composition(s) can also be performed each day during a chemotherapeutic treatment period and several days after the end of said chemotherapeutic treatment, typically 1, 2, 3, 4, 5, 6, 7 (one week), 8, 9 or 10 days after the end of said chemotherapeutic treatment.

In a particular embodiment, inventors thus herein provide a pharmaceutical composition comprising a functional (e.g., wild-type) TLR4 polypeptide, a nucleic acid encoding a functional TLR4 polypeptide, a vector comprising a nucleic acid encoding a functional TLR4 polypeptide or a recombinant host cell comprising a nucleic acid encoding a functional TLR4 polypeptide.

The composition may further or instead comprise at least one product as disclosed in the present invention, preferably selected from a biologically active compound capable of restoring or enhancing TLR4 expression, known or selected with a method as previously described.

Pharmaceutical compositions herein disclosed further comprise a pharmaceutically acceptable carrier or vehicle.

The use of a biologically active compound bypassing TLR4 signaling pathway and leading to NF-κB activation to prepare a pharmaceutical composition for treating or preventing a cancer in a subject, in particular in a subject having a mutated TLR4 nucleic acid or an abnormal TLR4 protein expression or activity is further herein provided.

The present invention also encompasses a biologically active compound bypassing TLR4 signaling pathway and leading to NF-κB activation, and a pharmaceutical composition comprising such a compound, to prevent or treat a cancer in a subject, in particular in a subject having a mutated TLR4 nucleic acid or an abnormal TLR4 protein expression or activity.

A preferred biologically active compound bypassing TLR4 signaling pathway and leading to NF-κB activation is a TLR3 or TLR9 ligand.

TLR3 ligands may be selected from Poly A:U and polyI:C for example.

TLR9 ligands may be selected from hypomethylated and G enriched oligonucleotides (CpG oligonucleotides—CpG A, B or C).

The use of an alcalinizing lysosomotropic compound to prepare a pharmaceutical composition for treating or preventing a cancer in a subject, in particular in a subject having a mutated TLR4 nucleic acid or an abnormal TLR4 protein expression or activity is further herein provided.

The present invention also encompasses an alcalinizing lysosomotropic compound, and a pharmaceutical composition comprising such a compound, to prevent or treat a cancer in a subject, in particular in a subject having a mutated TLR4 nucleic acid or an abnormal TLR4 protein expression or activity.

The alcalinizing lysosomotropic compound can be any compound selected from a compound interfering with vacuolar-ATPase, chloroquine, quinine and any combinations thereof. Examples of compound interfering with vacuolar-ATPase usable in the present invention are bafilomycin, apicularen, archazolid and concanamycin.

The bone marrow of a subject having a normal TLR4 protein expression or activity may further be used to prevent or treat a cancer in a subject, in particular in a subject having a mutated TLR4 nucleic acid or an abnormal TLR4 protein expression or activity, in particular in a subject as defined previously who will undergo a bone marrow transplantation.

The pharmaceutical compositions comprising a compound as disclosed above may also further comprise an anthracycline, oxali-platinum and/or cis-platinum (PLAT), as a combined preparation, for simultaneous, separate or sequential use in the prevention or treatment of said cancer.

A pharmaceutical composition comprising (i) a biologically active compound bypassing TLR4 signaling pathway and leading to NF-κB activation, preferably a TLR3 and/or a TLR9 ligand, and/or an alcalinizing lysosomotropic compound as described previously and (ii) a pharmaceutically acceptable carrier or vehicle is thus also herein provided. Said pharmaceutical composition may further comprise at least one product selected from an anthracycline, oxali-platinum and cis-platinum. Such a composition can be used to prevent or treat a cancer in a subject, in particular in a subject having a mutated TLR4 nucleic acid or an abnormal TLR4 protein expression or activity.

The above described pharmaceutical compositions can be administered before, for example one day before, and/or pending any chemotherapy or radiotherapy. They are preferably administered pending and/or after any chemotherapy or radiotherapy.

The administration of the pharmaceutical compositions herein provided may be performed by any method known to those skilled in the art, preferably by the oral route or by injection (preferably via systemic route). The administered doses may be adapted by those skilled in the art.

Typically, in terms of treatments, administration doses may be for example for 4-Epirubicine (anthracycline): 100 mg/m$^2$ every 3 weeks;

for Oxaliplatinum: around 600-1000 mg/m$^2$ every 3 weeks;

for nucleic acid compounds, doses may range for example for Poly A:U from 30-50 mg/week, during 6 weeks.

In the context of a prophylactic treatment, pharmaceutical compositions according to the invention are preferably administered every 3 weeks.

It is understood that repeated treatments may be performed, possibly in combination with other active agents, therapy or any pharmaceutically acceptable vehicle (eg., buffers, isotonic saline solutions, in the presence of stabilizers, etc.).

The invention also resides in method of treating or preventing a cancer in a subject, in particular in a subject having a mutated TLR4 nucleic acid or an abnormal TLR4 protein expression or activity, through an activation of TLR4 expression or activity. The subject can be a patient who will undergo an allogeneic bone marrow transplantation using the bone marrow of a donor subject having a normal TLR4 protein expression or activity.

More particularly, methods of treating a subject who carry mutated alleles of the TLR4 gene or express an abnormal TLR4 protein, including combined therapy are herein provided. Subjects may thus be treated for example through gene therapy, protein replacement therapy or through the administration of TLR4 protein mimetics and/or activators. At least one of said methods may further be combined to a chemotherapy or to a radiotherapy.

The invention also resides in method of treating cancer in a subject through an activation of TLR4 expression or activity using a product as herein described previously.

Diagnostic methods, as herein described, aimed at assessing the sensitivity of a subject to a treatment of cancer or at detecting innate or acquired TLR4 deficiencies in cancer patients or at risk of developing a cancer, may be applied to a subject selectable for such a treatment, in particular to a subject who will undergo a cancer treatment, in particular a chemotherapeutic treatment, and/or an allogeneic bone marrow transplantation. Concerning the subject who will undergo an allogeneic bone marrow transplantation, it is preferable to select an appropriate bone marrow donor subject. An appropriate bone marrow donor subject is a subject having a normal TLR4 protein expression or activity as herein defined.

Other characteristics and advantages of the invention are given in the following experimental section (with reference to FIGS. 1 to 17), which should be regarded as illustrative and not limiting the scope of the present application.

Experimental Section

Inventors first addressed the role of T cell-based immunity in the efficacy of a variety of pro-apoptotic agents commonly utilized in the armamentarium of oncologists to treat cancer. Firstly, they found that some compounds i.e DOX, PLAT and XR mediated more potent antitumour efficacy in immunocompetent mice compared with athymic Nu/Nu littermates devoid of T cells.

Secondly, as innate immunity dictates the outcome of cognate T cell-mediated immune responses, inventors screened the innate receptors involved in chemo-or radio-therapy-induced antitumour effects and found TLR4 electively implicated. Downstream of TLR4 signaling, TRIF and MyD88 are critical pathways leading to different inflammatory outcomes. Cytotoxic therapies induce immunogenic cell death through MyD88 and not TRIF.

Thirdly, inventors discovered that mice deficient for TLR4 recovered full susceptibility to radiotherapy (XR) -induced cell death and long term survival when XR were combined with TLR3 or TLR9 ligands.

Fourthly, inventors highlighted the mechanisms by which TLR4 is critical for long term survival following chemotherapy and/or X-rays therapy:
- cross presentation of exogenous antigens (apoptotic dead bodies) cannot occur appropriately and antitumour-specific T cells cannot be elicited;
- the intracellular routing of exogenous antigens is different in Wild Type (WT) DC and in TLR4−/− DC. In TLR4−/− DC an acceleration of exogenous antigens lysosomal degradation is observed.

Fifthly, inventors discovered that HMGB1 is involved in the cross presentation of apoptotic bodies by TLR4+ DC to CTL in vitro.

Inventors further demonstrate that the progression free survival (within 5 years) is significantly longer in female bearing a wt genotype versus female bearing a mutated Asp299Gly TLR4 allele (see FIG. 11, Log Rank analysis).

Lastly, inventors discovered that sporadic breast cancer patients or colon cancer patients also display a higher frequency of the mutated Asp299Gly allele (>25%) compared with controls (<10%).

1. Material and Methods

Mouse Strains.

Balb/c (H-$2^d$), C57BL/6 (H-$2^b$) and Nude Balb/c mice were obtained from the Centre d'elevage Janvier (Le Genest St Isle, France) and from Charles River Laboratories (L'Arbresle, France). Nude C57BL/6 mice were obtained from Taconic Animal Laboratory (Ejby, Denmark). Nude swiss mice (nu/nu) were bred within the inventor's own animal facility (Villejuif, France). Balb/c TLR4−/− mice (provided by Grégoire Lauvau) as well as MyD88−/− and Trif−/− mice on a C57BL/6 background (provided by Bernhard Ryffel) were raised within the inventor's pathogen-free animal facility. Finally, C57BL/10 and C57BL/10ScNJ mice were purchased from the Jackson Laboratory. Animals were used between 6 and 20 weeks of age. All animals were maintained according to the Animal Experimental Ethics Committee Guidelines (Val de Marne, France).

Tumour Cell Lines

CT26 and TS/A are respectively colon and mammary cancer cell lines syngenic to BALB/c mice. B16F10 is a melanoma cancer cell line syngenic to C57BL/6 mice. Cells were cultured at 37° C. under 5% C02 in RPMI 1640 medium supplemented with 10% FCS, penicillin, streptomycin, 1 mM pyruvate and 10 mM Hepes.

$3 \times 10^6$ treated CT26 cells were inoculated subcutaneously in 200 µl PBS into 6-wk-old female BALB/c mice (Charles River Laboratories) into the lower flank, whereas $5 \times 10^5$ untreated control cells were inoculated into the contralateral flank. Similarly, $1 \times 10^5$ TS/A cells were inoculated into the right flank of mice.

Cell Death Assays.

Cells were trypsinized and subjected to cytofluorometric analysis with a FACSVantage after staining with 2.5 µM DAPI for 10 min (Invitrogen) for determination of cell viability, and annexin V was conjugated with fluorescein isothiocyanate (Bender Medsystems) for the assessment of phosphatidylserine exposure [30].

Tumour Allografts.

Glasgow osteosarcoma (GOS) and Pancreatic adenocarcinoma (P03) tumours were kindly provided by F. Levi (Paul Brousse Hospital, Villejuif). The tumours were maintained in nu/nu mice over 6 weeks of age and passaged every 2 or 4 weeks respectively as subcutaneous (s.c) implants as previously described by Granda at al [31].

Reagents.

Ultrapure Lipopolysaccharide (LPS) was purchased from Invivogen and used at a final concentration of 1 µg/ml in culture. Polyinosine-polycytidylic acid (poly(I:C)) was obtained from Ampligen. For in vivo experiments, Poly(I:C) was diluted in saline and 50 µg were injected i.p. into mice subjected to XR treatment at day+1, day+4 and day+7 after radiotherapy. Similarly, CpG (50 µg) 5'-TCCATGACGTTC-CTGACGTT-3' (SEQ ID NO: 16) given by Dr. A. Carpentier (Department of Neurology, Groupe Hospitalier Pitié Salpétrière, Paris, France) was administered at day 1 after radiotherapy.

Inhibitory TLR4 Peptides.

TLR4 663-686 peptides with an NH2-terminal Tat sequence were as follow: TLR4 peptide, RKKRRQR-RRGKKYSRGESIYDAFVI-YSSQNEDWV (SEQ ID NO:

17); TLR4 mutant peptide, RKKRRQRRRGEEYSEG-ES-IYDAFVIYSSQNEDWV (SEQ ID NO: 18).

For in vivo experiments, 100 μg of peptides were administered i.p. into mice at day 0, day +3 and day +6 after immunization with CT26 apoptotic cells.

ODN Interfering with TLR7/9.

Oligonucleotide (ODN)-based inhibitor of TLR7/9 signaling and control ODN were kindly provided by F. Barrat (Dynavax, Berkeley, Calif., USA). The sequences of the TLR7/9 inhibitory ODN (IRS 954) and the control ODN (ODN532) are 5'-TGCTCCTGGAGGGGTTGT-3' (SEQ ID NO: 19) and 5'-TCCTGCAGGTTAAGT-3' (SEQ ID NO: 20) respectively. For in vivo experiments, ODNs were diluted in saline. To achieve efficient inhibition of TLR7/9 signaling, 50 μg ODNs were given i.p. to mice subjected to XR treatment at day−4, day−1 and day+2. Control mice received ODNs as well with the same schedule. To assess the efficacy of the inhibitory ODN, Balb/c mice were either injected s.c. with saline or with 25 μg of immunostimulatory CpG. Two hours after injection, blood was collected from mice and TNFα as well as IL-12p40 concentrations in mice' sera were determined by ELISA.

Preparation of Apoptotic Tumour Cells Vaccines (DOX or XR)

CT26 cells were cultured in culture medium supplemented with 20 μM of doxorubin for 4-24 h. Alternatively, B16OVA cells were treated with 1 μM idarubicin for 24 h (Aventis) to induce cell death.

Chemo- or Radio-Therapy Protocols to Promote Tumour Regression in Vivo

Balb/c mice were injected with $10^5$ TS/A cells within the right flank. Mice were then randomly assigned into treatment groups of 3-6 mice each. Tumour growth was monitored using a calliper. When tumour size reached 30-50 mm$^2$, the treatments were started. Mice were briefly anesthetized using isofurane and carefully placed into plastic constrainers to ensure immobilization. The whole body was protected by lead shielding, except for the area of the tumour to be irradiated. A total X-ray dose of 10Gy was delivered in a single shot.

C57BL/6 mice were implanted with tumour graft of either GOS or P03 into the skin. Treatment was started when tumour became palpable (as described by [31]). Mice bearing palpable GOS tumour were treated with oxaliplatin (5 mg/kg i.p.) at day 5. Similarly, mice bearing palpable P03 tumour (usually between day 9 and day 13) were injected i.p. with docetaxel (60 mg/kg).

Functional Assays on Mouse Dendritic Cells. Phagocytosis. Maturation. Cytokine Secretion. T Cell Activation.

Bone marrow derived dendritic cells (BMDC) were generated using FLT3l as previously described [30]. Maturation and phogocytosis experiments' were performed as previously described [30]. Briefly, dendritic cells were coincubated with CytoTracker Red—(CMTMR; Invitrogen) prestained apoptotic or necrotic CT26 cells at a ratio of 1:1 or 5:1 for 2 to 4 h for the phagocytosis experiments or 24 h for maturation experiments. Cells were then analyzed by FACS with FITC-conjugated antibodies (Becton Dickinson) specific for CD11c, MHC class II, CD40, CD80 and CD86 molecules.

Dendritic cell maturation and cytokine secretion was also assessed on freshly isolated CD11c$^+$ splenocytes purified using immunomagnetic beads (Miltenyi Biotec) and coincubated for 24 h with live or apoptotic CT26 or TS/A cells at ratios of 1:1 and 5:1. The supernatants were then harvested and IL-1b, IL-4, IL-6, IL-10, IL-12p70 and IFNg secretion were determined by ELISA (OptEIA ELISA Kit; BD Biosciences).

For the priming experiments, Bone marrow derived dendritic cells (BMDC) were prepared according to the protocol from Lutz et al. [32] with some modifications. BMDC were cultured in Iscoves's medium (Sigma) supplemented with Penicillin (100 U/ml Gibco), Streptomycin (100 μg/ml Gibco), L-glutamin (Gibco), 2-mercaptoethanol (50 μM, Sigma), 10% heat-inactivated and filtered FCS (Gibco), and 30% of J558 supernatant. BMDC were used between day 10 and day 12 when the proportion of dendritic cells (both CD11c+ and Class II+) within the culture was above 80%. BMDC were gently recovered and cocultured with apoptotic tumour cells (CT26 DX or B16OVA Ida) at a 10:1 ratio. After a four-hour incubation, BMDC loaded with apoptotic bodies were washed two times in Phosphate Saline Buffer (PBS) and $3.10^5$ loaded dendritic cells were injected into the footpad of Balb/c or C57BL/6 mice. Alternatively, for negative priming experiments, $3.10^5$ tumour cells were injected without dendritic cells.

At day 5, gangliocytes of draining lymph nodes were harvested, seeded in 96 well Maxisorp (Nunc) plates at $10^5$ cells/well, and subjected to a TCR cross-linking with anti-CD3e mAb (10 μg/ml) and low doses of IL-2 (100 U/ml). Supernatants were harvested 24 hours later and cytokine secretion was assessed by ELISA.

DNA Samples

Genomic material was obtained from a cohort of 153 women bearing breast cancer, recruited at the Gustave Roussy Institute between 1990 and 2006. Genomic DNA (gDNA) was isolated from blood leucocytes using commercially available kits (Qiagen). Alternatively, DNA was isolated from paraffin embedded tissues. 20 μm sections of non tumour tissues were deparaffinized with xylene and rehydrated with ethanol. Samples were then boiled at 95° C. for 5 minutes to recover DNA, which was finally stored at 4° C. before amplification.

Primers and Allele Specific Oligonucleotides (ASOs)

PCR primers were constructed by (Applied Biosystems) to amplify a 101 bp fragment containing the TLR4 Asp299Gly mutation site. The following primers were used for the Asp299Gly polymorphism: forward 5'-CCATTGAAGAAT-TCCGATTAGCATA-3' (SEQ ID NO: 21) and reverse 5'-CACTCACCAGGGAAAATGAAGAA-3' (SEQ ID NO: 22). Dual labelled ASOs (Applied Biosystems) were designed for the wild-type Asp299 allele and the 299Gly allelic variant with sense sequences: 5'-[VIC™]-CCTC-GATGATATTATT-[MGB][NFQ]-3' (SEQ ID NO: 23) and 5'-[6-FAM]-CTCGATGGTATTATTG-[MGB][NFQ]-3' (SEQ ID NO: 24), respectively. (The italicized bases indicate the polymorphic site for each ASO).

Polymerase Chain Reaction (PCR) Conditions and Data Analysis

A standard volume of 2 μl gDNA (5 ng) per reaction was amplified by adding 5 μl of 2× Universal Taqman Master Mix (Applied Biosystems), 0.25 μl of 40× PCR primers and Taqman MGB probes and 2.75 μl dH$_2$O. PCR reactions were run in 96 well fluorescence plates (ABgene). PCR conditions were as follows: initial denaturation at 95° C. for 10 min, 45 cycles of denaturation for 15 s at 92° C. and annealing for 60 s at 60° C. Fluorescence signals were measured automatically on a ABIPrism 7700 Sequence Detector (Applied Biosystems). Genotypes were assigned to each subject, by comparing the FAM signal to its corresponding VIC™ signal and calculating the −log(FAM/VIC) ratio for each data point as previously described by Van Rijn et al. [33].

2. Cytotoxic Compounds Inducing Antitumour Immune Responses

It has been recently reported that anthracycline-induced apoptosis promoted the immunogenicity of tumour cells in a caspase-dependent manner [30]. Therefore, inventors carried out a screening of several FDA-approved compounds commonly used in current protocols of chemotherapy which are capable of i) inducing apoptosis of tumour cells in vitro (including X-Rays) (FIG. 1A) and ii) inducing protective T cell immune responses against live tumour cells in vivo. The experimental setting was the following. CT26 colon cancer tumour cells were subjected to a 4-18 hr incubation with a cytotoxic compounds, washed and inoculated sc in BALC/c syngeneic mice in the abdominal flank. Fifteen days later, mice were challenged with 10 times the minimal tumourigenic dose of live CT26 tumour cells on the controlateral flank and the kinetics of tumour growth was monitored. Inventors found that cell death induced by oxaliplatinum (PLAT) (not shown), doxorubicin (or Idarubicin, DOX, FIG. 1B) and irradiation (not shown) could prevent the outgrowth of tumours in immunocompetent but not Nude littermates. In contrast, taxanes, mitomycin-C, while mediating apoptotic cell death, were as efficient in immunocompetent as in Nude mice (not shown). In a large list of various drugs inducing cell death, only anthracyclines, irradiation and oxaliplatinum (not shown) could mediate immunogenicity (FIG. 1B).

3. Anthracycline-Induced Apoptosis is Immunogenic in a TLR4-Dependent Manner As postulated by Janeway and coll., cognate immune responses are dictated by innate immunity. Since TLR4, 7-8 and 9 are critical components of innate immunity to foreign antigens, inventors assessed the role of these receptors in the anti-tumour immunity induced by apoptotic cells. In TLR4 loss of function mice (TLR4$^{-/-}$), the above mentioned vaccination (anthracycline-treated CT26) failed to protect the host against a live CT26 challenge (FIG. 2B). Similar results were obtained in wild type BALB/c mice injected with a competing peptide binding TLR4 (but not a mutated control peptide) (not shown).

Figure 1:
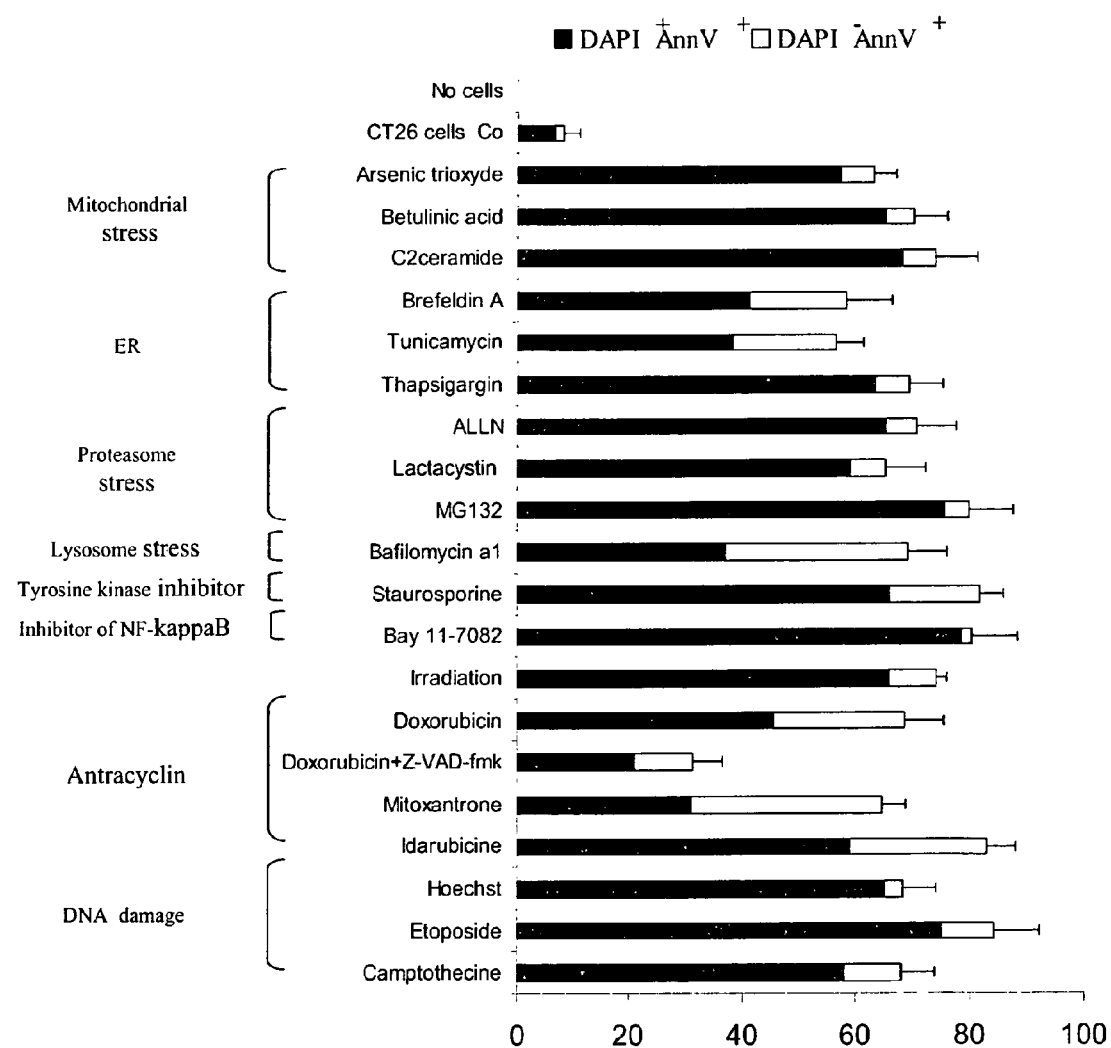
FIG. 1: Immunogenicity of apoptosis.
A. Drugs inducing apoptotic cell death in vitro. Various (FDA-approved or not) drugs were incubated on CT26 tumour cells. Flow cytometry analyses were performed on CT26 at 24 hrs after labeling with DAPI and annexin V. The percentages of double positive cells is in black, of annexin V+/DAPI– is in white bars.
B. Prophylactic vaccines composed of drug-induced apoptotic cells in wild type mice. $3 \times 10^6$ CT26 cells treated for 24 hrs with various drugs in vitro were inoculated in the left flank of BALB/c WT at day 0. Controls were PBS treated. At day 7, $5 \times 10^5$ live CT26 were injected in the right flank and tumour growth was monitored twice a week using a calliper. The percentages of tumour free mice are indicated. Each experiment included 5-10 mice/group and was performed at least twice yielding similar results. Statistical analyses were performed using Fisher's exact method and ANOVA. * indicate significant results at p<0.05.
Figure 1:
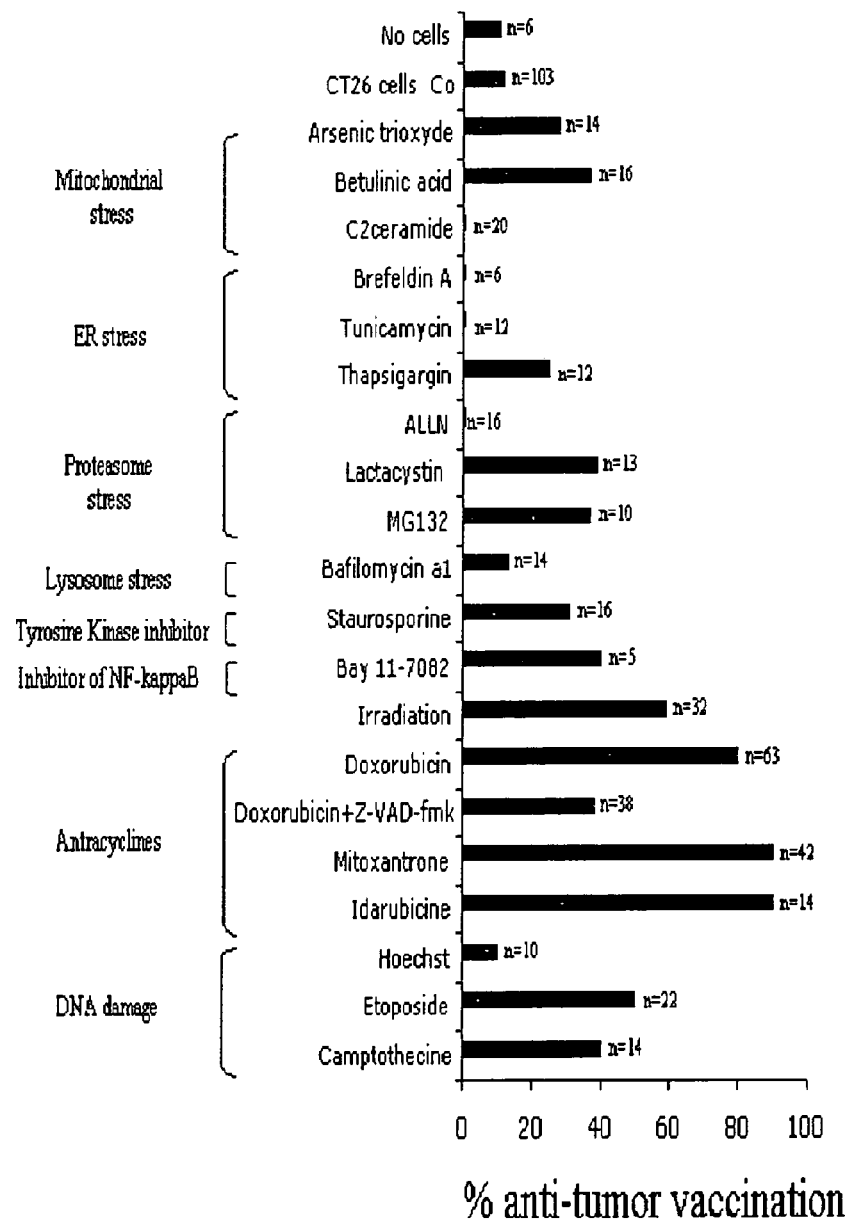
Figure 2C:
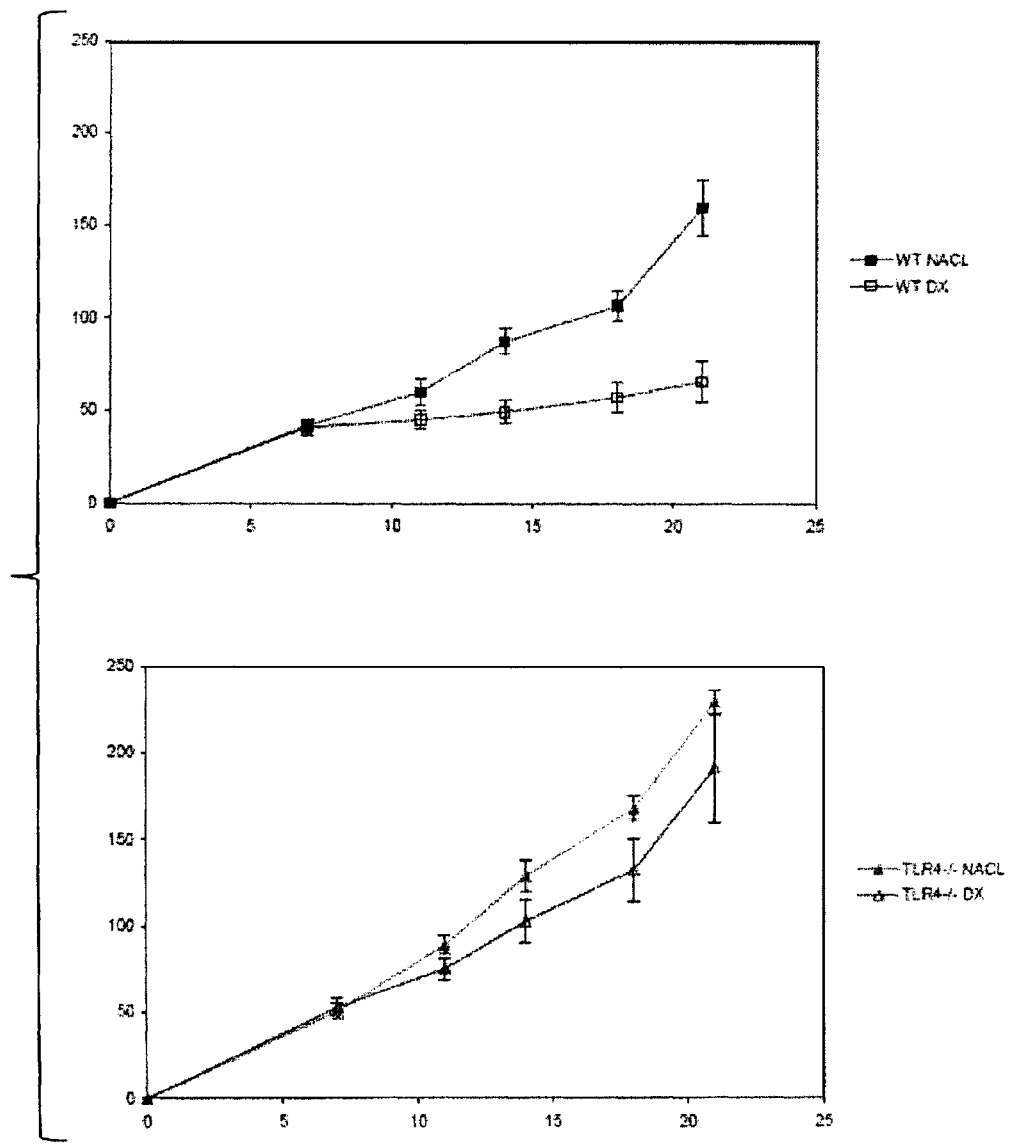
FIG. 2: TLR4 is critical in the immunogenicity of DOX-based prophylactic vaccines.
A. Natural CT26 (colon) tumour growth kinetics in TLR4−/− versus TLR4+/+ mice.
B. DOX-induced apoptosis of CT26 failed to protect TLR4−/− mice against CT26 challenge. Identical experimental setting as in 1B. but performed in TLR4−/− mice instead of BALB/c WT.
C. DOX is directly inoculated into established tumours in WT or TLR4−/− mice. The direct antitumour effect is monitored by measuring tumour sizes biweekly.

It is noteworthy that DOX coadministered with non immunogenic vaccines (such as mitomycin-C induced apoptotic tumour cells) does not induce T cell immunity, excluding the presence of TLR4 ligands in DOX preparations (not shown). In FIG. 2C, inventors show that direct inoculation of DOX into established tumours induce tumour regression in TLR4+/+ hosts but not in TLR4−/− littermates.

4. Platinum-Based Compounds Keep in Check Tumours through TLR4

To further outline the role of the immune system in the responsiveness to chemotherapy in tumour-bearing hosts, inventors evaluated the antitumour effects induced by systemic oxaliplatinum (PLAT) against an established graft of a Glasgow osteosarcoma in C57BL/6 immunocompetent (FIG. 3A), Nu/Nu swiss (athymic, FIG. 3B) and C57BL10ScNJ (carrying a mutated TLR4, FIG. 3C) mice. PLAT could significantly control tumour progression in immunocompetent but not Nu/Nu, C57BL/6 Nude Black mice (not shown) or TLR4 mutated mice. This experiment rules out a potential role of LPS contaminating the tumour inoculum since it deals with grafted tumour pieces.

5. X-Rays Control Tumour Growth in a TLR4-Dependent Fashion

X-Ray-induced apoptosis is able to protect mice against tumour challenge in prophylactic settings (FIG. 1A). Inventors assessed whether X-Rays could keep in check growing TS/A mammary tumours of 30-50 mm² in immunocompetent (IC) versus Nude BALB/c counterparts. First, the natural growth of TS/A was not significantly different in wt versus Nude versus TLR4−/− BALB/c mice (FIG. 4A). However, once again, the antitumour activity promoted by X-Rays was more potent in IC than in Nude mice or in TLR4 deficient littermates (FIG. 4B). It is important to stress that TLR7 and TLR9 are not involved in X-Ray-mediated antitumour immune responses (FIG. 4C). Oligonucleotide (ODN)-based inhibitors of both TLR7 and TLR9 were developed by Dynavax Technologies Corporation, Berkeley [34]. Specificity of these inhibitors was confirmed by inhibition of IFNα production by PDCs in response to DNA or RNA viruses [34]. In inventor's hands, such ODN could significantly decrease the serum levels of TNFα and IL-12p40 following CpG inoculation in vivo (not shown).

6. MvD88 but Not TRIF is Involved in PLAT-Mediated Immunogenicity

Since TLR4 can signal through TRIF or MyD88, inventors assessed which of these pathways is critical for the immunogenicity of PLAT-induced cell death in C57BL/6 mice bearing established osteosarcoma grafts. While PLAT maintained its antitumour efficacy in TRIF−/− animals (FIG. 5A), PLAT failed to induce significant tumour retardation in MyD88−/− counterparts (FIG. 5B).

7. TLR3 or TLR9 Ligands Bypass TLR4 Deficiencies and Restore Responsiveness to X-Rays Since TLR3 signals through TRIF which is not involved in the TLR4 transduction in our settings, inventors hypothesized that stimulation via TLR3 could potentiate X Ray-induced antitumour effects through independent mechanisms in TLR4 deficient hosts. Inventors indeed observed that PolyI:C, a double stranded RNA administered systemically during local radiotherapy, circumvented TLR4 deficiency in TS/A bearing-animals. Hence, while Poly I:C did not significantly hamper natural tumour progression in TLR4+/+ versus TLR4−/− mice (FIG. 6A), TLR4−/− mice benefited from X-Rays as much as TLR4+/+ mice only in the presence of Poly I:C (FIG. 6B).

Since TLR4 signals through MyD88 (leading to NF-kB activation), any TLR4 deficiency will prevent the interaction of the adapter protein MyD88 with TIR domains, indispensable for the signaling cascade leading to induction of pro-inflammatory cytokines. Since TLR9 can also promote MyD88 assembly, inventors addressed whether TLR9 ligands could bypass TLR4 deficiencies in the response to X-Rays. As described above for TLR3 ligation, TLR9 ligation not only exerted some antitumour activity during tumour progression in mice (FIG. 7A), but also restored the efficacy of X-Rays in TLR4−/− mice (FIG. 7B).

8. Cellular Mechanisms Involved in TLR4 Function: Insights

Figure 8A:
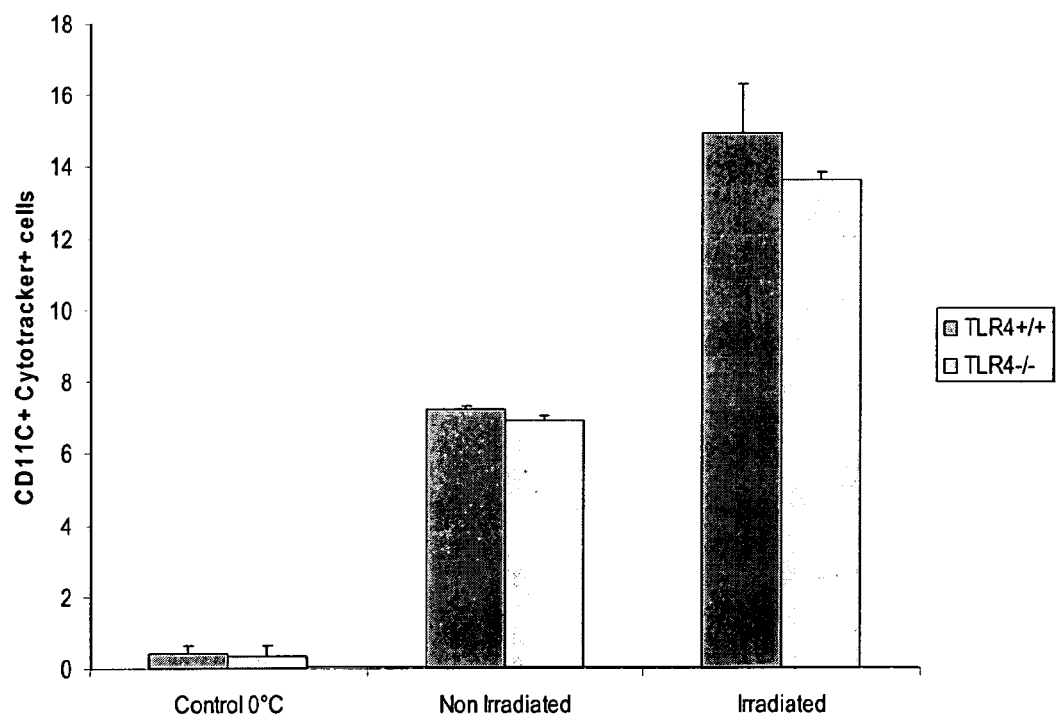
Figure 8B:
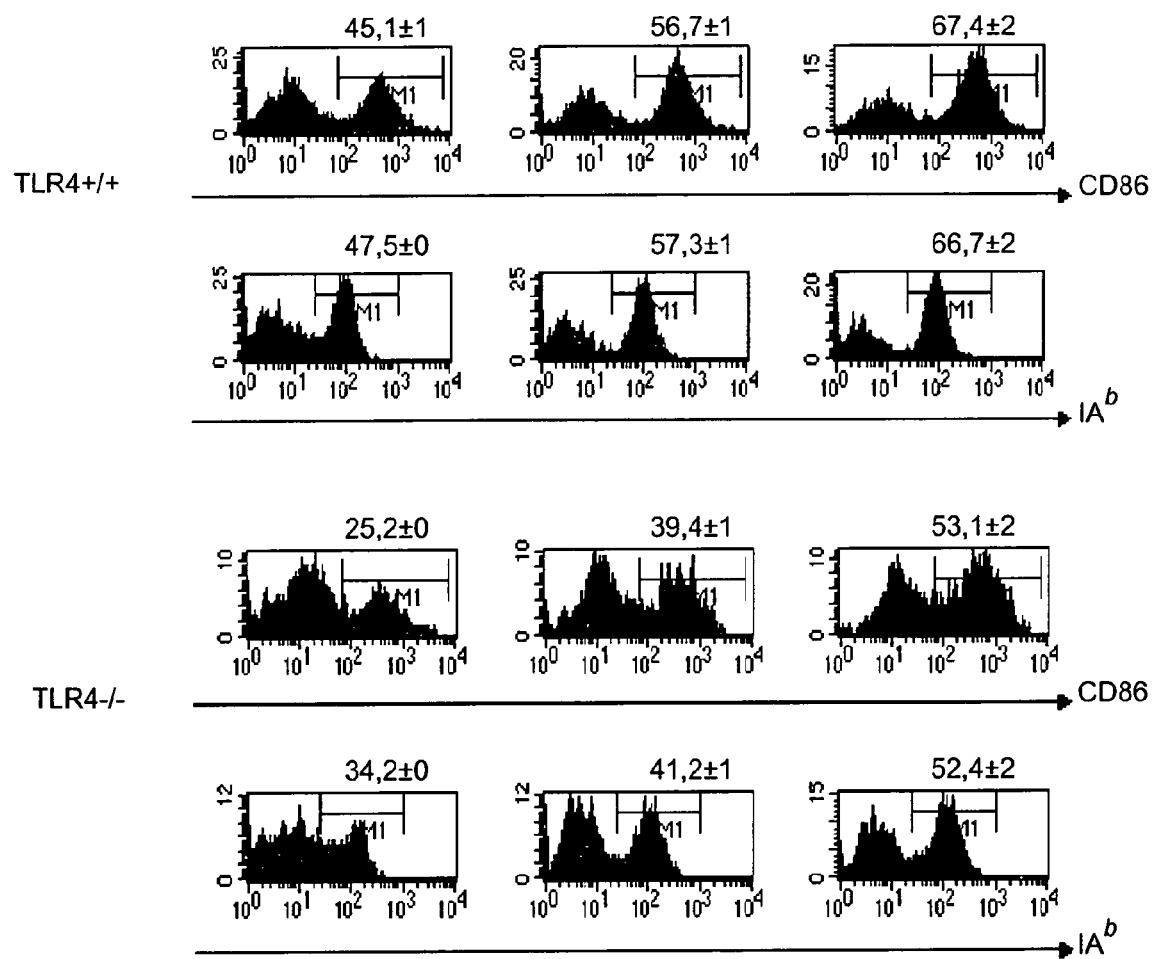
Figure 9A:
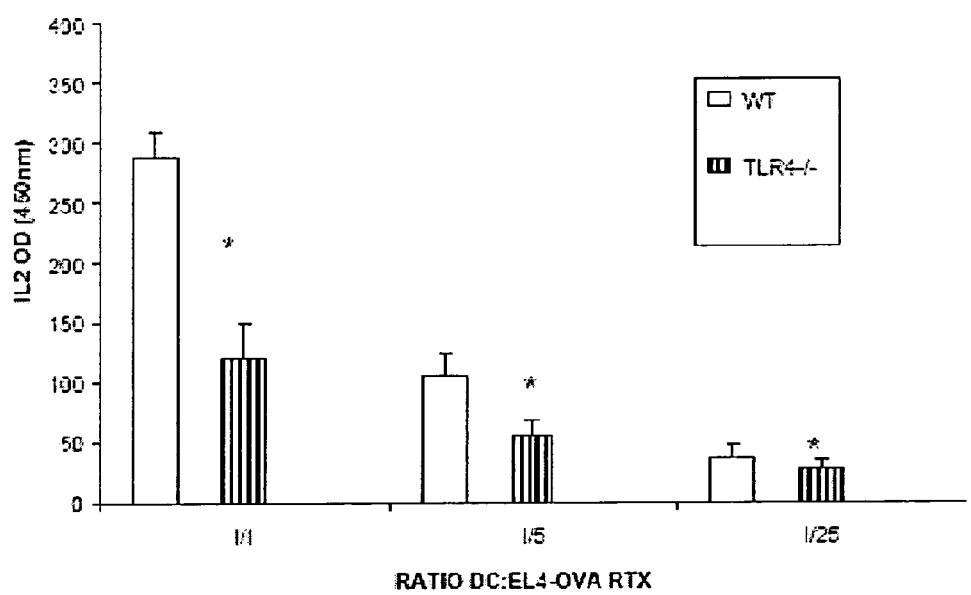
Figure 9B:
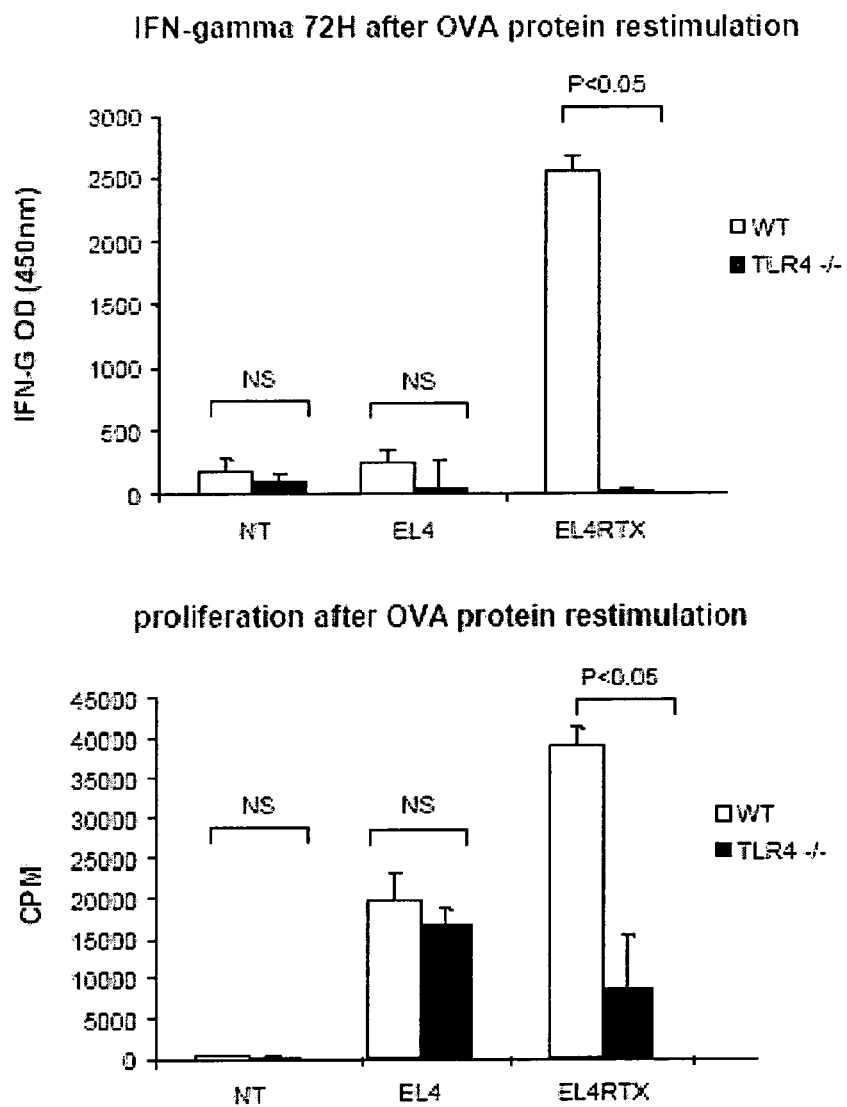
Figure 10A:
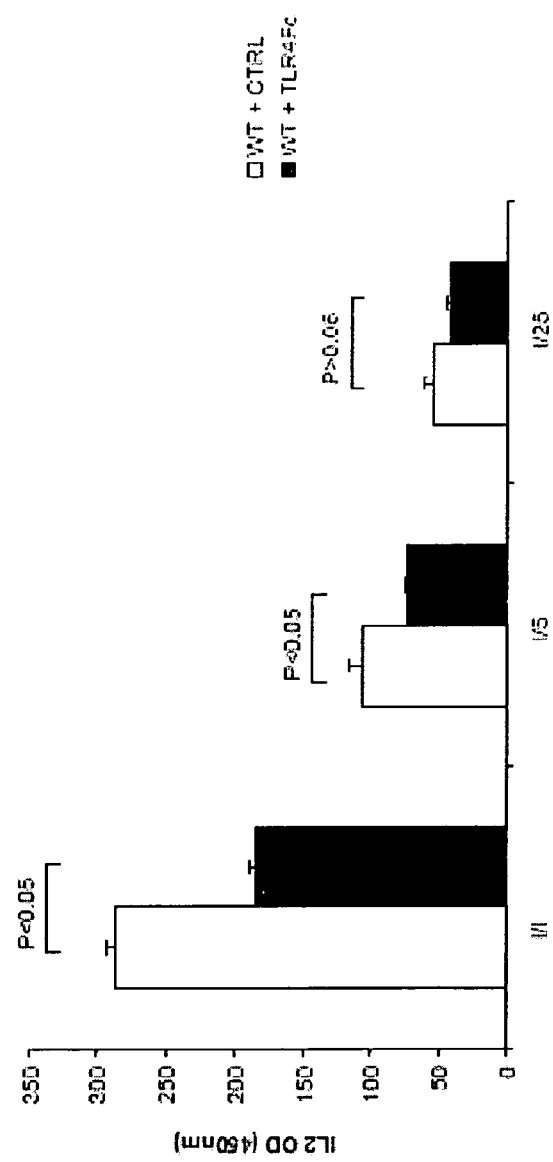
Figure 10B:
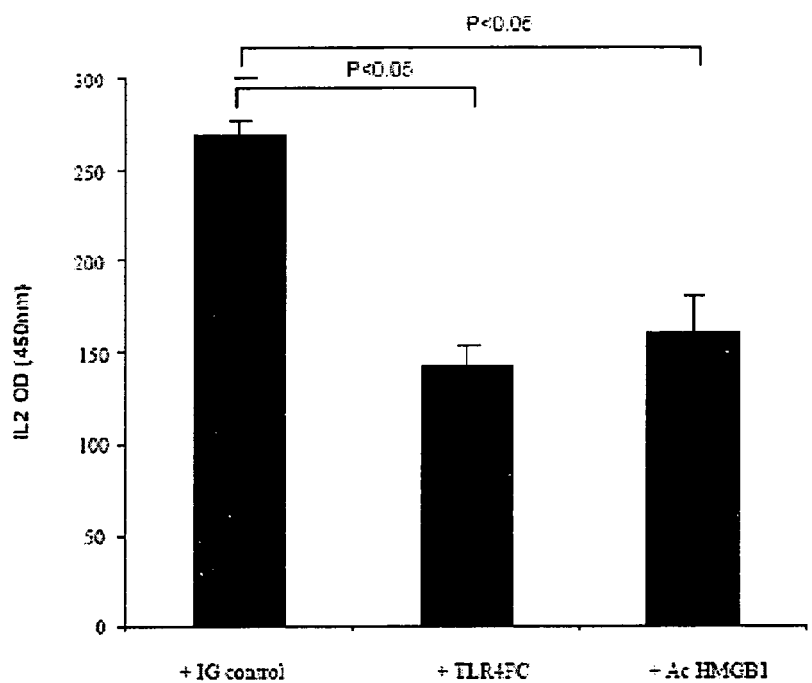

TLR4 is mainly expressed in myeloid cells in vivo (monocytes, DC). TLR4 signaling is critical for triggering secretion of pro-inflammatory cytokines (IL-1b, IL-6, TNFα and IL-12 when MyD88 is involved) and accelerating DC maturation. Both DC differentiation and activation enable priming and polarization of naïve T cells. Inventors assessed the differential capacity of bone marrow derived-DC (or DC freshly isolated from lymph nodes) to uptake and mature following incubation with EL4OVA tumour cells triggered in an apoptotic cell death program with irradiation (after 24 hrs of X-Ray stimulation). Uptake of apoptotic EL4OVA was similar in TLR4−/− and TLR4+/+ mice (FIG. 8A). The upregulation of MHC class II and CD86, stigmates of DC activation, was comparable in both TLR4−/− and TLR4+/+ mice (FIG. 8B, upper and lower panels). Secretion of IL-6 and TNFα when significant, were TLR4-independent (not shown). No secretion of IL-2 nor IL-12 could be detected. Despite outward signs of maturation exhibited by DC, DC-mediated T cell priming in TLR4$^{-/-}$ mice was affected. DC are likely the antigen presenting cells capable of processing irradiated-apoptotic tumour cells in vivo since irradiated EL4OVA apoptotic cells pulsed onto BM-DC generated from TLR4$^{-/-}$ mice cannot prime the B3Z clone (FIG. 9A). Following injection of irradiated EL4OVA into Balb/c mice, cross priming was deficient in TLR4$^{-/-}$ mice (FIG. 9B). Moreover, in vitro assays of cross presentation using mouse BM-DC pulsed with X Ray-induced apoptotic cells and incubated with antigen specific CTL clone revealed that TLR4–/– DC fail to activate specific CTL while TLR4+/+ cells do it unless TLR4Fc or anti-HMGB1 antibodies are added in the coculture (FIGS. 10A and 10B).

9. Analyses of Single Nucleotide Polymorphisms of TLR4 in the Resistance to Chemotherapy or Irradiation (Local Relapse)

Inventors carried out the genotyping of TLR4 Asp299Gly in breast cancer female admitted for diagnosis or therapy at IGR between 1980 and 2000. DNA was obtained from PBL or EBV-transformed B cells or paraffin-embedded tumour tissues. Genotyping was carried out by a single tube polymerase chain reaction based on exonuclease degradation of dual labelled allele-specific oligonucleotides (a method previously compared with conventional restriction fragment length polymorphism analysis and confirmed by direct sequencing [33]). Inventors assessed more than 500 breast cancer patients. About 10% of said patients beard a single mutant allele of TLR4 (a comparable rate as in historical controls of the literature, reviewed in [14]). Then, they examined the progression free survival (PFS) in two cohorts of Caucasian women bearing a familial breast cancer and matched for age, Nottingham prognostic index and adjuvant therapy (based on anthracycline, and X-Rays on tumour and ipsilateral chest): those exhibiting Asp299Gly or Gly299Gly mutations (n=12) and those exhibiting a WT phenotype for TLR4 (Asp299Asp) (n=24). In Log Rank analysis (FIG. 11A), the PFS was significantly superior in WT individuals at 5 years (p<0.05). Progression meant ipsi lateral relapse or metastases.

10. Analyses of Single Nucleotide Polymorphisms of TLR4 in the Susceptibility of Breast Cancer A prospective sampling of peripheral DNA has been performed between 2002 and 2006, in the medical intensive care unit (ICU) of Hôpital COCHIN (Pr Dhainaut) with the aim at determining the morbidity associated with TLR polymorphism on severity and outcome of severe sepsis. More than 600 cancer bearing patients have been admitted to the ICU out of 3000 patients and have been evaluated for Asp299Gly TLR4 SNP using a high throughput screening in automated RT-PCR (Taqman, Applied biosystem 7900).

The frequency of cases has been compared for each type of malignancies (Haematopoietic cancers vs solid tumours, and specifically colon, prostate, breast, leukemia, lymphoma, myeloma, NSCLC, etc.). These "cases" have been matched with "controls", which are patients hospitalized in the ICU and matched for age, sex, and ethnics. TLR4 SNP frequencies have been compared in the different groups and subgroups, analyzed as an independent criteria of occurrence of a septic shock and as a prognostic marker. The inventors' data point to the fact that the mutational status for TLR4 is an independent prognostic factor for the development of a sporadic breast cancer (FIG. 11B).

Figure 17C:
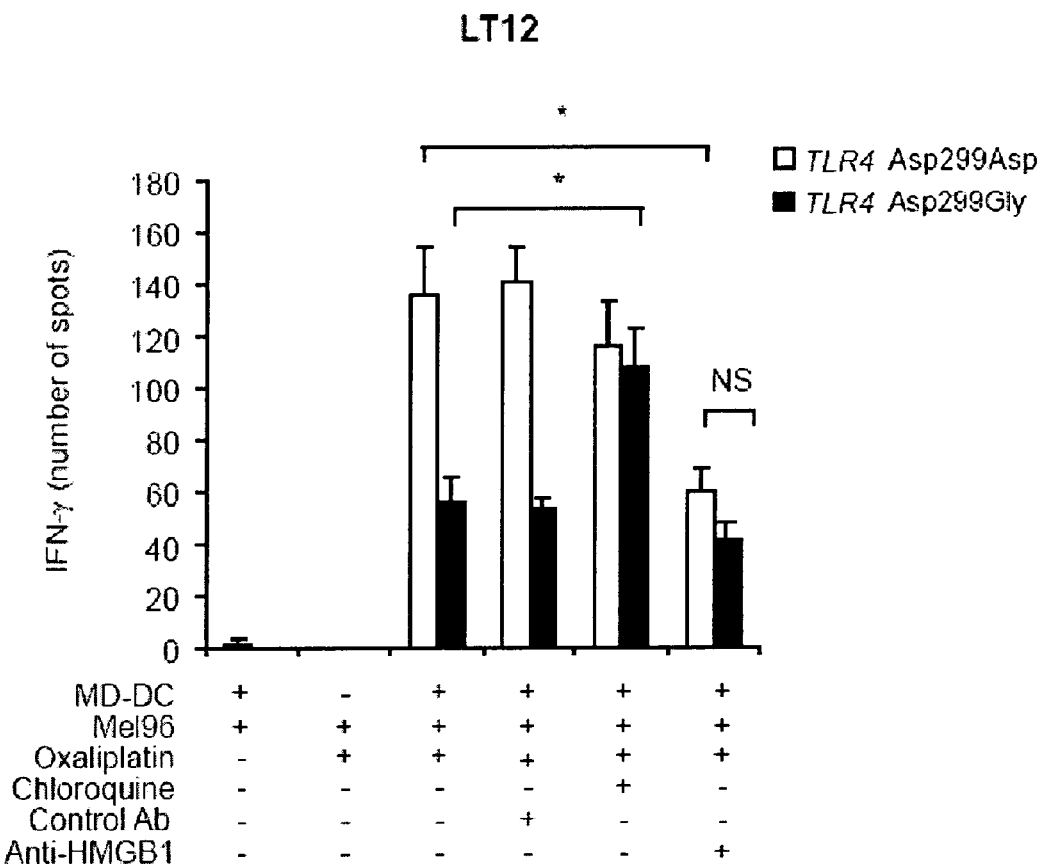

11. Use of Chloroquine or Quinine (Alcalinizing Lysosomotropic Drugs) or any Compounds Interfering with Vacuolar-ATPase (Promoting the Alcalinization of Lysosomes) to Compensate for TLR4 Deficiencies and to Restore Antigen Presentation and Response to Cytotoxic Agents in Prophylaxis and Therapy of Cancer Inventors have shown that a TLR4 mutant that reduces HMGB1 binding affects the prognosis of breast cancer patients treated by anthracyclines. A sequence polymorphism in TLR4 (896A/G, Asp299Gly, rs4986790) affecting the extracellular domain of TLR4 is associated with reduced endotoxin responses and with a reduced susceptibility to cardiovascular disease in humans [13, 18]. Although it is a matter of debate whether the TLR4 Asp299Gly mutation results in deficient LPS signaling [13, 23, 35], inventors addressed the possibility that the TLR4 Asp299Gly polymorphism could affect the response to HMGB1. Transfection of Hela cells (which contain WT TLR4) with either WT or mutant alleles of TLR4 demonstrated that the expression of mutant TLR4 receptor blunted the NF-κB activation in response to HMGB1 (not shown). Immunoprecipitation experiments were performed after adding HMGB1 to HeLa cells that were transfected with normal and mutated human TLR4. The binding of HMGB1 to the mutant (Asp299Gly) TLR4 was reduced, as compared to the normal (Asp299Asp) TLR4 (FIG. 17a), although both transfectants harbored similar amounts of TLR4 molecules. This defective binding of HMGB1 to the mutated TLR4 might account for the severely impaired capacity of monocyte derived-DC (MD-DC) to cross-present melanoma antigens to CTLs. MD-DC from individuals with normal (Asp299Asp) and mutant (Asp299Gly) TLR4 were undistinguishable in their capacity to stimulate alloreactive T cells in a reaction that could be stimulated by LPS (but only when the DC harboured the normal TLR4 allele) and not by HMGB1 (supplemental FIG. 17b). MD-DC from normal (Asp299Asp) individuals cross-presented MART1 derived from dying melanoma cells to CTL clones in an HMGB1-dependent manner FIG. 17c. In contrast, MD-DC from individuals bearing an Asp299Gly TLR4 allele were defective cross-presenters (FIG. 17c). Inventors herein demonstrate that this defect is restored by addition of chloroquine (FIG. 17c). Therefore, chloroquine can compensate for the defective ability of patients' dendritic cells to present tumour antigens to their T cells.

Figure 13A:
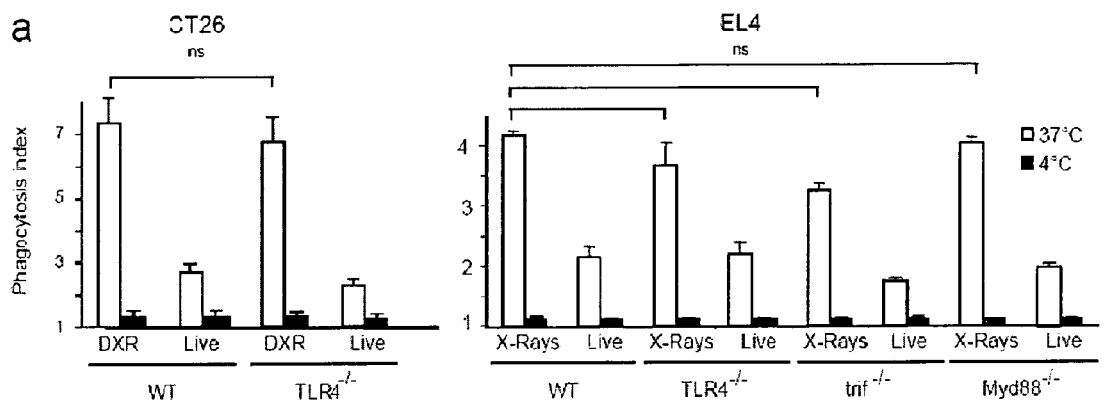
Figure 13B:
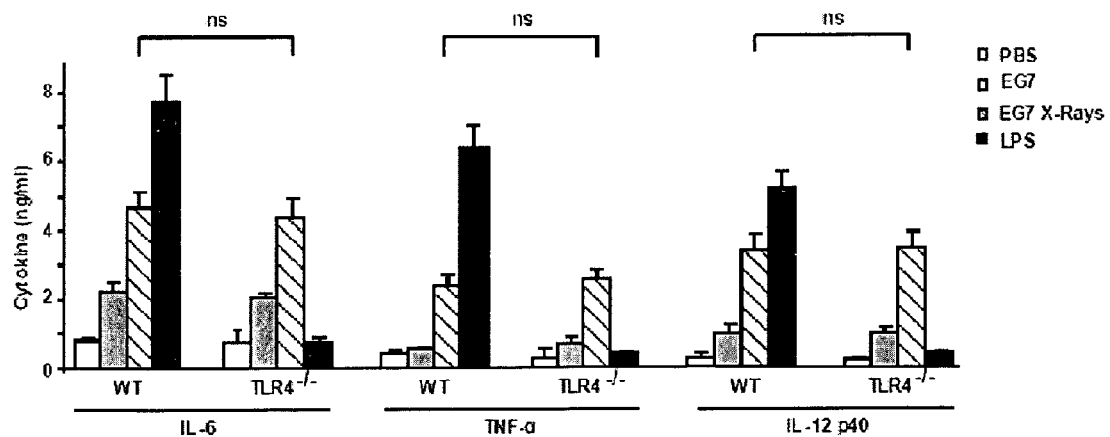
Figure 14A:
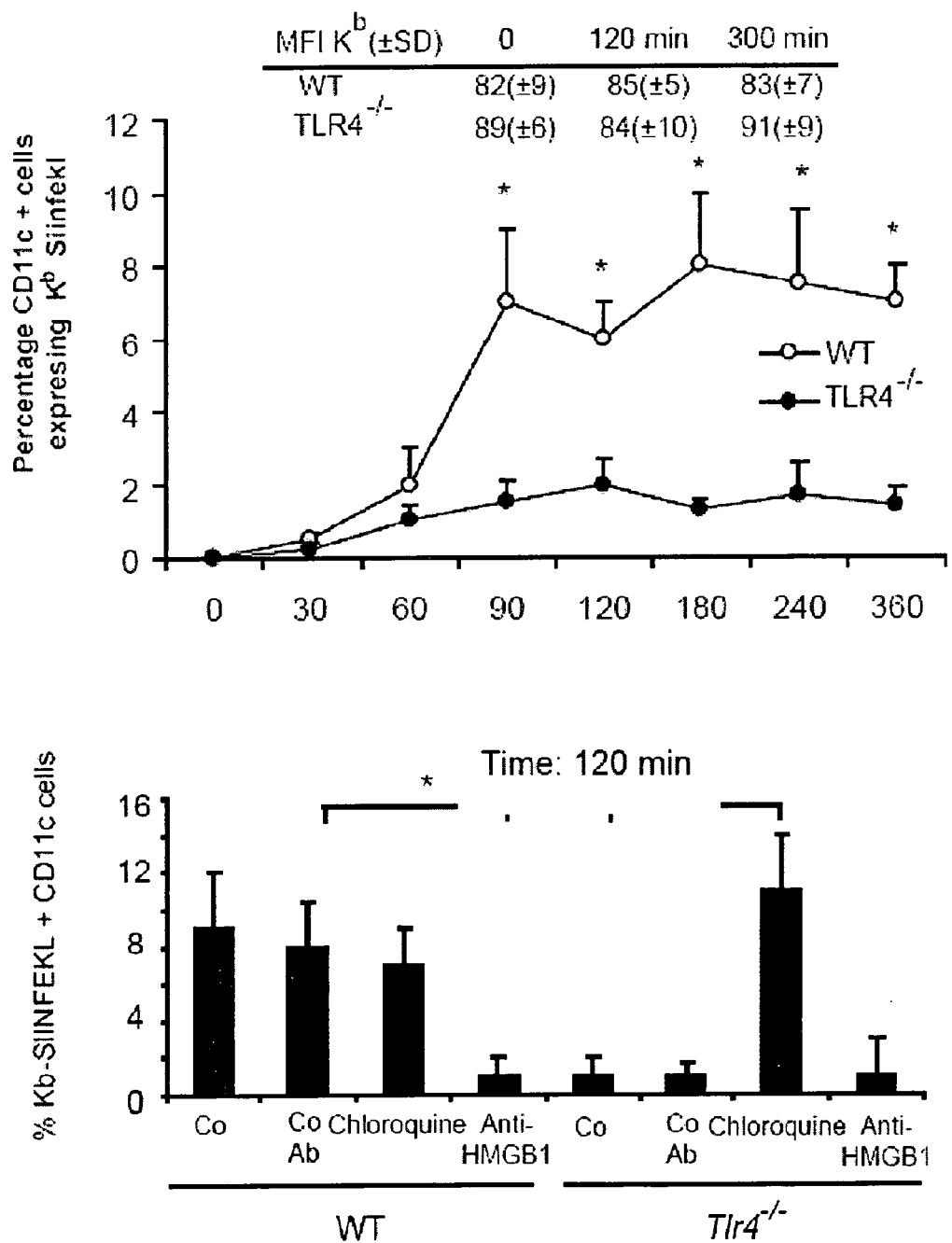

This result corroborates other data obtained in vitro with mouse dendritic cells. TLR4 controls the processing/presentation of antigen from dying tumour cells. TLR4 deficiency could compromise the anti-tumour immune response at the level of DC by affecting the uptake, processing/presentation of antigen and/or the provision of costimulatory signals. WT and TLR4$^{-/-}$ DC were equally efficient in engulfing irradiated EG7 thymoma or doxorubicin-treated CT26 colon carcinoma cells (FIG. 13a). The acquisition of maturation markers (including MHC class 11 and the costimulatory molecules CD40, CD80, CD86), and the production of inflammatory cytokines (IL-6, IL-12p40, TNF-α) by TLR4$^{-/-}$ DC, were deficient in response to bacterial lipopolysaccharide (LPS, a known TLR4 ligand), yet intact in response to dying tumour cells (not shown and FIG. 13b). However, TLR4 influenced the kinetics at which DC express K$^b$/SIINFEKL MHC class I/peptide complexes at the plasma membrane surface after loading them with dying OVA-transfected TS/A (H-2$^d$) cells. WT and TLR4$^{-/-}$ DC expressed comparable levels of K$^b$ molecules at baseline and acquired K$^b$/SIINFEKL complexes after pulsing with saturable amounts of free SIINFEKL peptides with similar kinetics (not shown). However, a markedly reduced exposure of K$^b$/SIINFEKL complexes was detected on TLR4$^{-/-}$ DC, as compared with WT controls, after loading with dying OVA-expressing TS/A cells (FIG. 14a).

Inventors herein demonstrate, based on these findings, that TLR4 is likely to affect the processing/presentation of antigen.

Figure 14B:
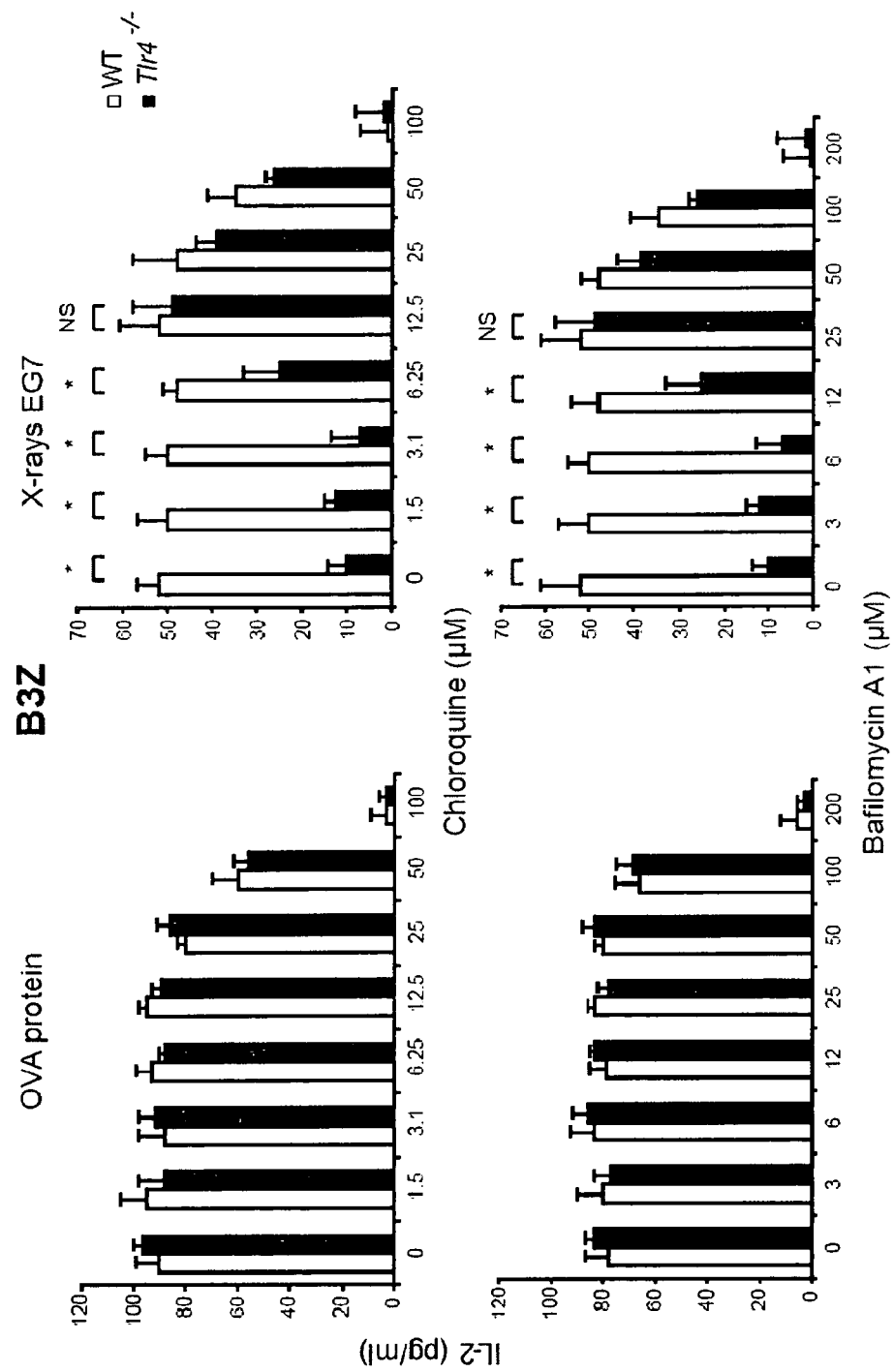

TLR4 has been reported to inhibit the lysosome-dependent degradation of phagosomes [36]. TLR4$^{-/-}$ DC would degrade dying cells in the lysosomal compartment instead of presenting their antigens [37]. In the present invention, inventors sought to restore antigen presentation by TLR4$^{-/-}$ DC by inhibiting the activity of lysosomes, either with chloroquine (a lysosomotropic alkaline product) or with bafilomycin A1 (a specific inhibitor of the vacuolar ATPase responsible for lysosomal acidification). Indeed, the alkalinization of lysosomes by either agent, preferably used at subtoxic concentrations (subtoxic concentrations in the mouse of chloroquine: 10-20 μM, bafilomycin A1: 20-30 μM), enhanced the capacity of TLR4$^{-/-}$ DC to present antigen from dying cells, yet did not ameliorate antigen presentation by WT DC (FIG. 14b). Accordingly, treatment of TLR4$^{-/-}$ DC with chloroquine restored the ability of DC to present K$^b$/SIINKEKL complexes to normal levels (FIG. 14a, lower panel). Next, inventors directly determined the kinetics of fusion between phagosomes and lysosomes in WT versus TLR4$^{-/-}$ DC loaded with dying tumour cells. A significant acceleration of the colocalization of the phagocytic cargo with lysosomes was observed in TLR4$^{-/-}$ DC compared with WT DC (FIG. 14c).

These data confirm that TLR4 regulates the processing/presentation of tumour cell antigens by DC, presumably by inhibiting the lysosomal destruction of antigens.

12. Chloroquine and Quinine Restores the Responsiveness to Chemotherapy in Animals Lacking TLR4 Molecules.

Figure 15A:
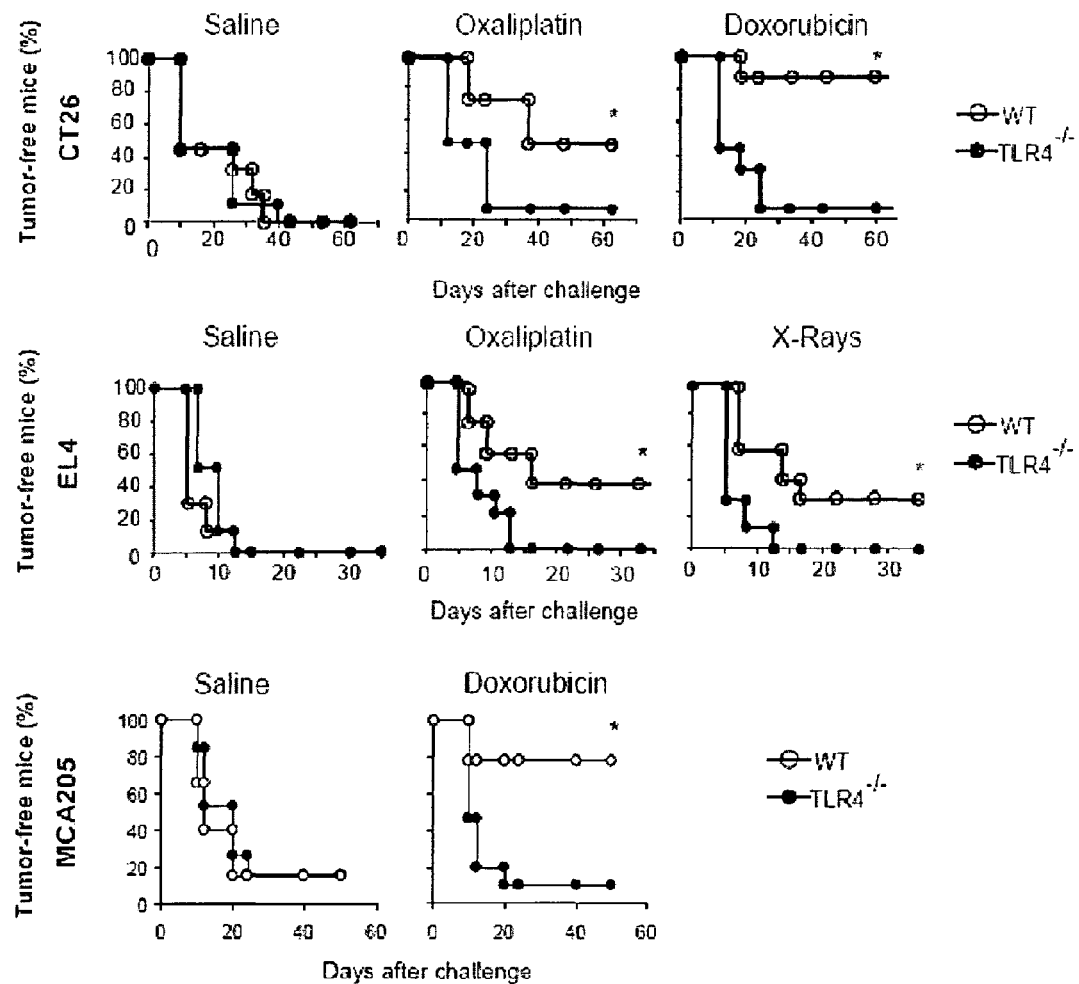
Figure 15B:
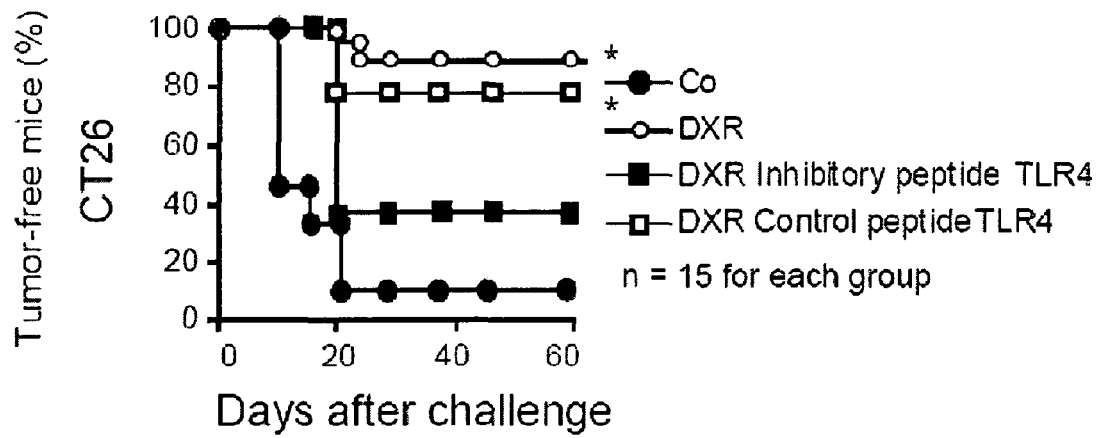
Figure 15C:
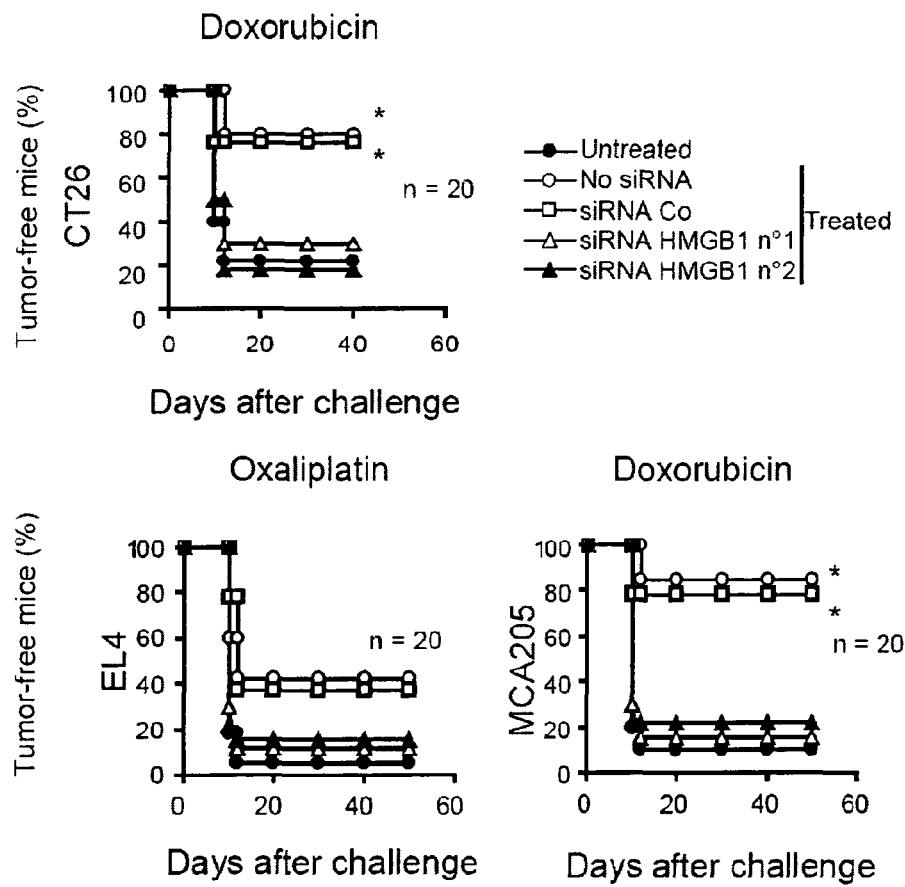

Injection of doxorubicin-treated CT26 colon cancer cells is highly efficient in inducing an immune response that prevents the growth of live CT26 cells inoculated one week later [30]. Similar results were obtained with doxorubicin-treated MCA205 sarcoma cells protecting against MCA205. While this applied to WT mice, no tumour vaccination could be achieved with anthracycline or oxaliplatin-treated cells in TLR4$^{-/-}$ mice (FIG. 15a). These data could be confirmed for oxaliplatin or irradiated EL4 thymoma cells, which failed to protect TLR4$^{-/-}$ hosts against tumour challenge (FIG. 15a). The pharmacological inhibition of TLR4 with a cell-permeable blocking peptide [38] that was coinjected with dying tumour cells also prevented anti-tumour immunity (FIG. 15b). Moreover, the depletion of the TLR4 ligand HMGB1 from anthracycline or oxaliplatin-treated CT26 cells using neutralizing antibodies (FIG. 15b) or HMGB1-specific siRNAs (FIG. 15c) compromised the efficacy of anti-tumour vaccination.

In a clinically more relevant setting, namely the treatment of established tumours with systemic chemotherapy or local radiotherapy, inventors found that the presence of TLR4 dictated the therapeutic outcome. CT26 colon cancers (FIG. 16a), TS/A breast carcinomas (FIG. 16b), heterotransplanted GOS osteosarcomas (FIG. 16c), and EL4 thymomas (FIG. 16d), progressed at a similar kinetics in immunocompetent WT, TLR4$^{-/-}$, and nu/nu athymic mice. Chemotherapy with appropriate cytotoxic agents or local radiotherapy reduced tumour growth and prolonged the survival of tumour-bearing mice in immunocompetent WT mice, yet was less effective in TLR4$^{-/-}$ (FIG. 16a-d) and nu/nu mice (FIG. 16b and not shown). In accordance with the in vitro data (FIG. 12), Trif$^{-/-}$ mice mounted a similar chemotherapeutic response as WT mice while MyD88$^{-/-}$ animals behaved like immunodeficient mice (FIG. 16c). Similarly, the inhibition of TLR7 and 9 with a synthetic oligonucleotide using a regimen that suppresses IFNα production from plasmacytoid DC in response to TLR7 and 9 ligands [34] in vivo failed to influence the efficacy of radiotherapy (not shown). Moreover, systemic administration of chloroquine enhanced the efficacy of chemotherapy in TLR4$^{-/-}$ mice but not in WT mice (FIG. 16d) in accordance with data presented in FIG. 14. These results point to a hitherto unrecognized contribution of TLR4/MyD88-dependent immunity to chemotherapeutic regimens that have been thought to act exclusively via tumour cell-intrinsic cytotoxic effects. It is important to note that such an immune effect on chemotherapeutic outcome was only detected for a limited set of drugs such as anthracyclines and oxaliplatin, while paclitaxel, camptothecin and alkylating agents were equally efficient in immunocompetent and immunodeficient mice (not shown).

Case Report

A breast cancer patient carrying the Asp299Gly TLR4 mutation and presenting with a unique lung metastasis was progressing with a therapy combining Navelbine and Xeloda for 3 months. The pulmonary nodule grew from a size of 10 mm to 22 mm within 3 months. After 3 months of the same chemotherapy regimen combined with oral chloroquine 200 mg/day for 14 days (and one week of, restart idem for 3 cycles), the nodule remained stable (RECIST criteria).

Protocol Using Chloroquine

Therapy of established tumours (adjuvant therapy):

Chloroquine (100 to 300 mg/day) has been administered for a duration corresponding to the administration of the cytotoxic compounds (chemotherapy) plus 5 days after.

Protocol Using Quinine

In TLR4 mutated patients, quinine can be administered Intravenously at 8 mg/kg every 8 hours (×3/day) for 3 days, starting preferably the next day post chemotherapy or radiotherapy.

REFERENCES

1. Medzhitov, R. and C. A. Janeway, Jr., *Innate immunity: the virtues of a nonclonal system of recognition.* Cell, 1997. 91(3): p. 295-8.
2. Medzhitov, R., *Toll-like receptors and innate immunity.* Nat Rev Immunol, 2001. 1(2): p. 135-45.
3. Takeda, K. and S. Akira, *Toll-like receptors in innate immunity.* Int Immunol, 2005. 17(1): p. 1-14.
4. Beutler, B., X. Du, and A. Poltorak, *Identification of Toll-like receptor 4 (Tlr4) as the sole conduit for LPS signal transduction: genetic and evolutionary studies.* J Endotoxin Res, 2001. 7(4): p. 277-80.
5. Hoshino, K., et al., *Cutting edge: Toll-like receptor 4 (TLR4)-deficient mice are hyporesponsive to lipopolysaccharide: evidence for TLR4 as the Lps gene product.* J Immunol, 1999. 162(7): p. 3749-52.
6. Kobe, B. and J. Deisenhofer, *A structural basis of the interactions between leucine-rich repeats and protein ligands.* Nature, 1995. 374(6518): p. 183-6.
7. Kawai, T., et al., *Unresponsiveness of MyD88-deficient mice to endotoxin.* Immunity, 1999. 11(1): p. 115-22.
8. Hoebe, K., E. Janssen, and B. Beutler, *The interface between innate and adaptive immunity.* Nat Immunol, 2004. 5(10): p. 971-4.
9. Shimazu, R., et al., *MD-2, a molecule that confers lipopolysaccharide responsiveness on Toll-like receptor 4.* J Exp Med, 1999. 189(11): p. 1777-82.
10. Yamamoto, M., et al., *Role of adaptor TRIF in the MyD88-independent toll-like receptor signaling pathway.* Science, 2003. 301(5633): p. 640-3.
11. Fitzgerald, K. A., et al., *LPS-TLR4 signaling to IRF-3/7 and NF-kappaB involves the toll adapters TRAM and TRIF.* J Exp Med, 2003. 198(7): p. 1043-55.

12. Schroder, N. W., et al., *Lipoteichoic acid (LTA) of Streptococcus pneumoniae and Staphylococcus aureus activates immune cells via Toll-like receptor (TLR)-2, lipopolysaccharide-binding protein (LBP), and CD14, whereas TLR-4 and MD-2 are not involved.* J Biol Chem, 2003. 278(18): p. 15587-94.

13. Arbour, N. C., et al., *TLR4 mutations are associated with endotoxin hyporesponsiveness in humans.* Nat Genet, 2000. 25(2): p. 187-91.

14. Schroder, N. W. and R. R. Schumann, *Single nucleotide polymorphisms of Toll-like receptors and susceptibility to infectious disease.* Lancet Infect Dis, 2005. 5(3): p. 156-64.

15. Lorenz, E., et al., *Relevance of mutations in the TLR4 receptor in patients with gram-negative septic shock.* Arch Intern Med, 2002. 162(9): p. 1028-32.

16. Genc, M. R., et al., *Relationship between a toll-like receptor-4 gene polymorphism, bacterial vaginosis-related flora and vaginal cytokine responses in pregnant women.* Eur J Obstet Gynecol Reprod Biol, 2004. 116(2): p. 152-6.

17. Tal, G., et al., *Association between common Toll-like receptor 4 mutations and severe respiratory syncytial virus disease.* J Infect Dis, 2004. 189(11): p. 2057-63.

18. Kiechl, S., et al., *Toll-like receptor 4 polymorphisms and atherogenesis.* N Engl J Med, 2002. 347(3): p. 185-92.

19. Ameziane, N., et al., *Association of the Toll-like receptor 4 gene Asp299Gly polymorphism with acute coronary events.* Arterioscler Thromb Vasc Biol, 2003. 23(12): p. e61-4.

20. Balistreri, C. R., et al., *Role of Toll-like receptor 4 in acute myocardial infarction and longevity.* Jama, 2004. 292(19): p. 2339-40.

21. Smirnova, I., et al., *Excess of rare amino acid polymorphisms in the Toll-like receptor 4 in humans.* Genetics, 2001. 158(4): p. 1657-64.

22. Smirnova, I., et al., *Assay of locus-specific genetic load implicates rare Toll-like receptor 4 mutations in meningococcal susceptibility.* Proc Natl Acad Sci USA, 2003. 100 (10): p. 6075-80.

23. Erridge, C., J. Stewart, and I. R. Poxton, *Monocytes heterozygous for the Asp299Gly and Thr399Ile mutations in the Toll-like receptor 4 gene show no deficit in lipopolysaccharide signaling.* J Exp Med, 2003. 197(12): p. 1787-91.

24. von Aulock, S., et al., *Heterozygous toll-like receptor 4 polymorphism does not influence lipopolysaccharide-induced cytokine release in human whole blood.* J Infect Dis, 2003. 188(6): p. 938-43.

25. Michel, O., et al., *Systemic responsiveness to lipopolysaccharide and polymorphisms in the toll-like receptor 4 gene in human beings.* J Allergy Clin Immunol, 2003. 112(5): p. 923-9.

26. Zheng, S. L., et al., *Sequence variants of toll-like receptor 4 are associated with prostate cancer risk: results from the CAncer Prostate in Sweden Study.* Cancer Res, 2004. 64(8): p. 2918-22.

27. Chen, Y. C., et al., *Sequence variants of Toll-like receptor 4 and susceptibility to prostate cancer.* Cancer Res, 2005. 65(24): p. 11771-8.

28. Bauer, A. K., et al., *Toll-like receptor 4 in butylated hydroxytoluene-induced mouse pulmonary inflammation and tumorigenesis.* J Natl Cancer Inst, 2005. 97(23): p. 1778-81.

29. Okamoto, M., et al., *Expression of toll-like receptor 4 on dendritic cells is significant for anticancer effect of dendritic cell-based immunotherapy in combination with an active component of OK-432, a streptococcal preparation.* Cancer Res, 2004. 64(15): p. 5461-70.

30. Casares, N., et al., *Caspase-dependent immunogenicity of doxorubicin-induced tumor cell death.* J Exp Med, 2005. 202(12): p. 1691-701.

31. Granda, T. G., et al., *Circadian optimization of irinotecan and oxaliplatin efficacy in mice with Glasgow osteosarcoma.* Br J Cancer, 2002. 86(6): p. 999-1005.

32. Lutz, M. B., et al., *An advanced culture method for generating large quantities of highly pure dendritic cells from mouse bone marrow.* J Immunol Methods, 1999. 223(1): p. 77-92.

33. Van Rijn, B. B., et al., *Single step high-throughput determination of Toll-like receptor 4 polymorphisms.* J Immunol Methods, 2004. 289(1-2): p. 81-7.

34. Barrat, F. J., et al., *Nucleic acids of mammalian origin can act as endogenous ligands for Toll-like receptors and may promote systemic lupus erythematosus.* J Exp Med, 2005. 202(8): p. 1131-9.

35. van der Graaf, C., et al., *Functional consequences of the Asp299Gly Toll-like receptor-4 polymorphism.* Cytokine, 2005. 30(5): p. 264-8.

36. Shiratsuchi, A., et al., *Inhibitory effect of Toll-like receptor 4 on fusion between phagosomes and endosomes/lysosomes in macrophages.* J Immunol, 2004. 172(4): p. 2039-47.

37. Delamarre, L., et al., *Enhancing immunogenicity by limiting susceptibility to lysosomal proteolysis.* J Exp Med, 2006. 203(9): p. 2049-55.

38. Huang, B., et al., *Toll-like receptors on tumor cells facilitate evasion of immune surveillance.* Cancer Res, 2005. 65(12): p. 5009-14.

---

The invention claimed is:

1. An in vitro method of assessing the sensitivity of a subject having a cancer selected from breast cancer, sarcoma, ovarian cancer, endometrium cancer, bladder cancer, cervical cancer, prostate cancer, lung cancer, ORL cancer, paediatric tumours, neuroblastoma, glioblastoma multiforme, lymphoma, leukaemia, myeloma, seminoma, Hodgkin's lymphoma or malignant hemopathies to a chemotherapeutic treatment of said cancer comprising determining the presence of a mutated Toll Like Receptor 4 (TLR4) nucleic acid in a sample from the subject or determining the absence of TLR4 alleles in a sample from the subject, said mutated TLR4 nucleic acid being a wild-type TLR4 nucleic acid comprising a point mutation or a single nucleotide polymorphism (SNP) leading to the substitution of asparagine by glycine at position 299, wherein the presence of said mutated TLR4 nucleic acid or the absence of TLR4 alleles is indicative of a resistance to said chemotherapeutic treatment.

2. The method of claim 1, wherein the chemotherapeutic treatment includes administration of an anthracycline.

3. The method of claim 1, wherein the chemotherapeutic treatment includes administration of oxali-platinum or cis-platinum.

4. The method of claim 1, wherein the treatment further includes X-rays (XR).

5. The method of claim 1, wherein the presence of a mutated TLR4 nucleic acid is determined by restriction digestion, sequencing, selective hybridisation and/or selective amplification.

6. The method of claim 5, wherein the presence of a mutated TLR4 nucleic acid is determined by selective hybridisation with a nucleic acid probe present on a nucleotide array.

7. The method of claim 1, comprising (a) isolating from the subject a test sample of DNA, (b) contacting the test sample with at least one nucleic acid probe, wherein said nucleic acid is complementary to and specifically hybridises with a mutated TLR4 sequence comprising a point mutation or a single nucleotide polymorphism (SNP) leading to the substitution of asparagine by glycine at position 299 to form a hybridization sample, (c) maintaining the hybridization sample under conditions sufficient for the specific hybridization of the TLR4 sequence with the nucleic acid probe to occur, and (d) detecting whether there is specific hybridization of the mutated TLR4 sequence with the nucleic acid probe.

8. The method of claim 1, wherein the subject will undergo an allogeneic bone marrow transplantation using the bone marrow of a donor subject having a normal TLR4 protein expression or activity.

9. The method of claim 1, wherein said cancer is breast cancer.

10. The method of claim 1, wherein said cancer is a sarcoma.

11. The method of claim 1, wherein said cancer is ovarian cancer.

12. The method of claim 1, wherein said cancer is cancer of the endometrium.

13. The method of claim 1, wherein said cancer is bladder cancer.

14. The method of claim 1, wherein said cancer is cervical cancer.

15. The method of claim 1, wherein said cancer is prostate cancer.

16. The method of claim 1, wherein said cancer is lung cancer.

17. The method of claim 1, wherein said cancer is ORL cancer.

18. The method of claim 1, wherein said cancer is a paediatric tumour.

19. The method of claim 1, wherein said cancer is neuroblastoma.

20. The method of claim 1, wherein said cancer is glioblastoma multiforme.

21. The method of claim 1, wherein said cancer is lymphoma.

22. The method of claim 1, wherein said cancer is leukaemia.

23. The method of claim 1, wherein said cancer is myeloma.

24. The method of claim 1, wherein said cancer is seminoma.

25. The method of claim 1, wherein said cancer is Hodgkin's lymphoma.

26. The method of claim 1, wherein said cancer is a malignant hemopathy.

27. The method of claim 1, wherein said method determines the absence of said TLR4 alleles and comprises (a) isolating from the subject a test sample of DNA, (b) contacting the test sample with at least one nucleic acid probe, wherein said nucleic acid is complementary to and specifically hybridises with a TLR4 sequence to form a hybridization sample, (c) maintaining the hybridization sample under conditions sufficient to allow specific hybridization of the TLR4 sequence with the nucleic acid probe to occur, and (d) determining the presence or absence of TLR4 alleles by detecting specific hybridization of the nucleic acid probe.

28. The method according to claim 1, wherein said method further comprises treating a subject having a cancer selected from breast cancer, sarcoma, ovarian cancer, endometrium cancer, bladder cancer, cervical cancer, prostate cancer, lung cancer, ORL cancer, paediatric tumours, neuroblastoma, glioblastoma multiforme, lymphoma, leukaemia, myeloma, seminoma, Hodgkin's lymphoma or malignant hemopathies and whose cells contain unmutated TLR4 alleles with a chemotherapeutic treatment.

29. An in vitro method of assessing the sensitivity of a subject having a cancer selected from breast cancer, stomach cancer, sarcoma, ovarian cancer, endometrium cancer, bladder cancer, cervical cancer, prostate cancer, lung cancer, ORL cancer, paediatric tumours, neuroblastoma, glioblastoma multiforme, lymphoma, leukaemia, myeloma, seminoma, Hodgkin's lymphoma or malignant hemopathies to a chemotherapeutic treatment of said cancer comprising determining the presence of a mutated Toll Like Receptor 4 (TLR4) nucleic acid in a sample from the subject or determining the absence of TLR4 alleles in a sample from the subject, said mutated TLR4 nucleic acid being a wild-type TLR4 nucleic acid comprising a point mutation or a single nucleotide polymorphism (SNP) leading to the substitution of asparagine by glycine at position 299, wherein the presence of said mutated. TLR4nucleic acid or the absence of TLR4 alleles is indicative of a resistance to said chemotherapeutic treatment and treating a subject having a cancer selected from breast cancer, stomach cancer, sarcoma, ovarian cancer, endometrium cancer, bladder cancer, cervical cancer, prostate cancer, rectal cancer, lung cancer, ORL cancer, paediatric tumours, neuroblastoma, glioblastoma multiforme, lymphoma, leukaemia, myeloma, seminoma, Hodgkin's lymphoma or malignant hemopathies and whose cells lack TLR4 alleles or contain mutated TLR4 alleles with a composition comprising an alcalinizing lysosomotropic compound.

30. An in vitro method of assessing the sensitivity of a subject having a cancer selected from breast cancer, sarcoma, ovarian cancer, endometrium cancer, bladder cancer, cervical cancer, prostate cancer, lung cancer, ORL cancer, paediatric tumours, neuroblastoma, glioblastoma multiforme, lymphoma, leukaemia, myeloma, seminoma, Hodgkin's lymphoma or malignant hemopathies to a chemotherapeutic treatment of said cancer comprising determining the presence of a mutated Toll Like Receptor 4 (TLR4) nucleic acid in a sample from the subject or determining the absence of TLR4 alleles in a sample from the subject, said mutated TLR4nucleic acid being a wild-type TLR4 nucleic acid comprising a point mutation or a single nucleotide polymorphism (SNP) leading to the substitution of asparagine by glycine at position 299, wherein the presence of said mutated TLR4 nucleic acid or the absence of TLR4 alleles is indicative of a resistance to said chemotherapeutic treatment and treating a subject having a cancer selected from breast cancer, stomach cancer, sarcoma, ovarian cancer, endometrium cancer, bladder cancer, cervical cancer, prostate cancer, rectal cancer, lung cancer, ORL cancer, paediatric tumours, neuroblastoma, glioblastoma multiforme, lymphoma, leukaemia, myeloma, seminoma, Hodgkin's lymphoma or malignant hemopathies and whose cells contain unmutated TLR4 alleles with a chemotherapeutic treatment.

* * * * *

UNITED STATES PATENT AND TRADEMARK OFFICE
CERTIFICATE OF CORRECTION

PATENT NO. : 8,557,517 B2
APPLICATION NO. : 12/373789
DATED : October 15, 2013
INVENTOR(S) : Lionel Apetoh, Guido Kroemer and Laurence Zitvogel Page 1 of 1

It is certified that error appears in the above-identified patent and that said Letters Patent is hereby corrected as shown below:

In the Specifications

Column 9,
Lines 60-61, "cancer", SIINFEKL "susceptible" should read --cancer", "susceptible--.

Column 11,
Line 30, "(.g, organ" should read --(e.g., organ--.

Column 30,
Lines 47-50, "5'-[VIC™]-CCTCGATGATATTATT-[MGB][NFQ]-3' (SEQ ID NO: 23) and
            5'-[6-FAM]-CTCGATGGTATTATTG-[MGB] [NFQ]-3' (SEQ ID NO: 24)"
            should read
            --5'-[VIC™]-CCTCGATG*A*TATTATT-[MGB][NFQ]-3' (SEQ ID NO: 23) and
            5'-[6-FAM]-CTCGATG*G*TATTATTG-[MGB][NFQ]-3' (SEQ ID NO: 24)--.

Signed and Sealed this
Eleventh Day of March, 2014

Michelle K. Lee
*Deputy Director of the United States Patent and Trademark Office*

SEQUENCE LISTING

```
<160> NUMBER OF SEQ ID NOS: 24

<210> SEQ ID NO 1
<211> LENGTH: 5503
<212> TYPE: DNA
<213> ORGANISM: Homo sapiens
<220> FEATURE:
<221> NAME/KEY: CDS
<222> LOCATION: (142)..(2661)

<400> SEQUENCE: 1
tttgaataca ccaattgctg tggggcggct cgaggaagag aagacaccag tgcctcagaa      60
actgctcggt cagacggtga tagcgagcca cgcattcaca gggccactgc tgctcacaga     120
```

```
agcagtgagg atgatgccag g atg atg tct gcc tcg cgc ctg gct ggg act        171
                        Met Met Ser Ala Ser Arg Leu Ala Gly Thr
                          1               5                  10 ctg atc cca gcc atg gcc ttc ctc tcc tgc gtg aga cca gaa agc tgg        219
Leu Ile Pro Ala Met Ala Phe Leu Ser Cys Val Arg Pro Glu Ser Trp
             15                  20                  25 gag ccc tgc gtg gag gtg gtt cct aat att act tat caa tgc atg gag        267
Glu Pro Cys Val Glu Val Val Pro Asn Ile Thr Tyr Gln Cys Met Glu
             30                  35                  40 ctg aat ttc tac aaa atc ccc gac aac ctc ccc ttc tca acc aag aac        315
Leu Asn Phe Tyr Lys Ile Pro Asp Asn Leu Pro Phe Ser Thr Lys Asn
         45                  50                  55 ctg gac ctg agc ttt aat ccc ctg agg cat tta ggc agc tat agc ttc        363
Leu Asp Leu Ser Phe Asn Pro Leu Arg His Leu Gly Ser Tyr Ser Phe
     60                  65                  70 ttc agt ttc cca gaa ctg cag gtg ctg gat tta tcc agg tgt gaa atc        411
Phe Ser Phe Pro Glu Leu Gln Val Leu Asp Leu Ser Arg Cys Glu Ile
 75                  80                  85                  90 cag aca att gaa gat ggg gca tat cag agc cta agc cac ctc tct acc        459
Gln Thr Ile Glu Asp Gly Ala Tyr Gln Ser Leu Ser His Leu Ser Thr
                 95                 100                 105 tta ata ttg aca gga aac ccc atc cag agt tta gcc ctg gga gcc ttt        507
Leu Ile Leu Thr Gly Asn Pro Ile Gln Ser Leu Ala Leu Gly Ala Phe
             110                 115                 120 tct gga cta tca agt tta cag aag ctg gtg gct gtg gag aca aat cta        555
Ser Gly Leu Ser Ser Leu Gln Lys Leu Val Ala Val Glu Thr Asn Leu
             125                 130                 135 gca tct cta gag aac ttc ccc att gga cat ctc aaa act ttg aaa gaa        603
Ala Ser Leu Glu Asn Phe Pro Ile Gly His Leu Lys Thr Leu Lys Glu
         140                 145                 150 ctt aat gtg gct cac aat ctt atc caa tct ttc aaa tta cct gag tat        651
Leu Asn Val Ala His Asn Leu Ile Gln Ser Phe Lys Leu Pro Glu Tyr
 155                 160                 165                 170 ttt tct aat ctg acc aat cta gag cac ttg gac ctt tcc agc aac aag        699
Phe Ser Asn Leu Thr Asn Leu Glu His Leu Asp Leu Ser Ser Asn Lys
                 175                 180                 185 att caa agt att tat tgc aca gac ttg cgg gtt cta cat caa atg ccc        747
Ile Gln Ser Ile Tyr Cys Thr Asp Leu Arg Val Leu His Gln Met Pro
             190                 195                 200 cta ctc aat ctc tct tta gac ctg tcc ctg aac cct atg aac ttt atc        795
Leu Leu Asn Leu Ser Leu Asp Leu Ser Leu Asn Pro Met Asn Phe Ile
         205                 210                 215 caa cca ggt gca ttt aaa gaa att agg ctt cat aag ctg act tta aga        843
Gln Pro Gly Ala Phe Lys Glu Ile Arg Leu His Lys Leu Thr Leu Arg
 220                 225                 230 aat aat ttt gat agt tta aat gta atg aaa act tgt att caa ggt ctg        891
Asn Asn Phe Asp Ser Leu Asn Val Met Lys Thr Cys Ile Gln Gly Leu
 235                 240                 245                 250 gct ggt tta gaa gtc cat cgt ttg gtt ctg gga gaa ttt aga aat gaa        939
Ala Gly Leu Glu Val His Arg Leu Val Leu Gly Glu Phe Arg Asn Glu
                 255                 260                 265 gga aac ttg gaa aag ttt gac aaa tct gct cta gag ggc ctg tgc aat        987
Gly Asn Leu Glu Lys Phe Asp Lys Ser Ala Leu Glu Gly Leu Cys Asn
             270                 275                 280 ttg acc att gaa gaa ttc cga tta gca tac tta gac tac tac ctc gat       1035
Leu Thr Ile Glu Glu Phe Arg Leu Ala Tyr Leu Asp Tyr Tyr Leu Asp
             285                 290                 295 gat att att gac tta ttt aat tgt ttg aca aat gtt tct tca ttt tcc       1083
Asp Ile Ile Asp Leu Phe Asn Cys Leu Thr Asn Val Ser Ser Phe Ser
 300                 305                 310
```

| | | |
|---|---|---|
| ctg gtg agt gtg act att gaa agg gta aaa gac ttt tct tat aat ttc<br>Leu Val Ser Val Thr Ile Glu Arg Val Lys Asp Phe Ser Tyr Asn Phe<br>315                    320                    325               330 | 1131 | |
| gga tgg caa cat tta gaa tta gtt aac tgt aaa ttt gga cag ttt ccc<br>Gly Trp Gln His Leu Glu Leu Val Asn Cys Lys Phe Gly Gln Phe Pro<br>               335                   340                   345 | 1179 | |
| aca ttg aaa ctc aaa tct ctc aaa agg ctt act ttc act tcc aac aaa<br>Thr Leu Lys Leu Lys Ser Leu Lys Arg Leu Thr Phe Thr Ser Asn Lys<br>350                    355                    360 | 1227 | |
| ggt ggg aat gct ttt tca gaa gtt gat cta cca agc ctt gag ttt cta<br>Gly Gly Asn Ala Phe Ser Glu Val Asp Leu Pro Ser Leu Glu Phe Leu<br>               365                   370                   375 | 1275 | |
| gat ctc agt aga aat ggc ttg agt ttc aaa ggt tgc tgt tct caa agt<br>Asp Leu Ser Arg Asn Gly Leu Ser Phe Lys Gly Cys Cys Ser Gln Ser<br>380                    385                    390 | 1323 | |
| gat ttt ggg aca acc agc cta aag tat tta gat ctg agc ttc aat ggt<br>Asp Phe Gly Thr Thr Ser Leu Lys Tyr Leu Asp Leu Ser Phe Asn Gly<br>395                    400                    405               410 | 1371 | |
| gtt att acc atg agt tca aac ttc ttg ggc tta gaa caa cta gaa cat<br>Val Ile Thr Met Ser Ser Asn Phe Leu Gly Leu Glu Gln Leu Glu His<br>                         415                   420                   425 | 1419 | |
| ctg gat ttc cag cat tcc aat ttg aaa caa atg agt gag ttt tca gta<br>Leu Asp Phe Gln His Ser Asn Leu Lys Gln Met Ser Glu Phe Ser Val<br>430                    435                    440 | 1467 | |
| ttc cta tca ctc aga aac ctc att tac ctt gac att tct cat act cac<br>Phe Leu Ser Leu Arg Asn Leu Ile Tyr Leu Asp Ile Ser His Thr His<br>               445                   450                   455 | 1515 | |
| acc aga gtt gct ttc aat ggc atc ttc aat ggc ttg tcc agt ctc gaa<br>Thr Arg Val Ala Phe Asn Gly Ile Phe Asn Gly Leu Ser Ser Leu Glu<br>460                    465                    470 | 1563 | |
| gtc ttg aaa atg gct ggc aat tct ttc cag gaa aac ttc ctt cca gat<br>Val Leu Lys Met Ala Gly Asn Ser Phe Gln Glu Asn Phe Leu Pro Asp<br>475                    480                    485               490 | 1611 | |
| atc ttc aca gag ctg aga aac ttg acc ttc ctg gac ctc tct cag tgt<br>Ile Phe Thr Glu Leu Arg Asn Leu Thr Phe Leu Asp Leu Ser Gln Cys<br>                         495                   500                   505 | 1659 | |
| caa ctg gag cag ttg tct cca aca gca ttt aac tca ctc tcc agt ctt<br>Gln Leu Glu Gln Leu Ser Pro Thr Ala Phe Asn Ser Leu Ser Ser Leu<br>510                    515                    520 | 1707 | |
| cag gta cta aat atg agc cac aac aac ttc ttt tca ttg gat acg ttt<br>Gln Val Leu Asn Met Ser His Asn Asn Phe Phe Ser Leu Asp Thr Phe<br>               525                   530                   535 | 1755 | |
| cct tat aag tgt ctg aac tcc ctc cag gtt ctt gat tac agt ctc aat<br>Pro Tyr Lys Cys Leu Asn Ser Leu Gln Val Leu Asp Tyr Ser Leu Asn<br>540                    545                    550 | 1803 | |
| cac ata atg act tcc aaa aaa cag gaa cta cag cat ttt cca agt agt<br>His Ile Met Thr Ser Lys Lys Gln Glu Leu Gln His Phe Pro Ser Ser<br>555                    560                    565               570 | 1851 | |
| cta gct ttc tta aat ctt act cag aat gac ttt gct tgt act tgt gaa<br>Leu Ala Phe Leu Asn Leu Thr Gln Asn Asp Phe Ala Cys Thr Cys Glu<br>               575                   580                   585 | 1899 | |
| cac cag agt ttc ctg caa tgg atc aag gac cag agg cag ctc ttg gtg<br>His Gln Ser Phe Leu Gln Trp Ile Lys Asp Gln Arg Gln Leu Leu Val<br>                         590                   595                   600 | 1947 | |
| gaa gtt gaa cga atg gaa tgt gca aca cct tca gat aag cag ggc atg<br>Glu Val Glu Arg Met Glu Cys Ala Thr Pro Ser Asp Lys Gln Gly Met<br>               605                   610                   615 | 1995 | |
| cct gtg ctg agt ttg aat atc acc tgt cag atg aat aag acc atc att<br>Pro Val Leu Ser Leu Asn Ile Thr Cys Gln Met Asn Lys Thr Ile Ile<br>620                    625                    630 | 2043 | |

| | | |
|---|---|---|
| ggt gtg tcg gtc ctc agt gtg ctt gta gta tct gtt gta gca gtt ctg<br>Gly Val Ser Val Leu Ser Val Leu Val Val Ser Val Val Ala Val Leu<br>635 640 645 650 | | 2091 |
| gtc tat aag ttc tat ttt cac ctg atg ctt ctt gct ggc tgc ata aag<br>Val Tyr Lys Phe Tyr Phe His Leu Met Leu Leu Ala Gly Cys Ile Lys<br>655 660 665 | | 2139 |
| tat ggt aga ggt gaa aac atc tat gat gcc ttt gtt atc tac tca agc<br>Tyr Gly Arg Gly Glu Asn Ile Tyr Asp Ala Phe Val Ile Tyr Ser Ser<br>670 675 680 | | 2187 |
| cag gat gag gac tgg gta agg aat gag cta gta aag aat tta gaa gaa<br>Gln Asp Glu Asp Trp Val Arg Asn Glu Leu Val Lys Asn Leu Glu Glu<br>685 690 695 | | 2235 |
| ggg gtg cct cca ttt cag ctc tgc ctt cac tac aga gac ttt att ccc<br>Gly Val Pro Pro Phe Gln Leu Cys Leu His Tyr Arg Asp Phe Ile Pro<br>700 705 710 | | 2283 |
| ggt gtg gcc att gct gcc aac atc atc cat gaa ggt ttc cat aaa agc<br>Gly Val Ala Ile Ala Ala Asn Ile Ile His Glu Gly Phe His Lys Ser<br>715 720 725 730 | | 2331 |
| cga aag gtg att gtt gtg gtg tcc cag cac ttc atc cag agc cgc tgg<br>Arg Lys Val Ile Val Val Val Ser Gln His Phe Ile Gln Ser Arg Trp<br>735 740 745 | | 2379 |
| tgt atc ttt gaa tat gag att gct cag acc tgg cag ttt ctg agc agt<br>Cys Ile Phe Glu Tyr Glu Ile Ala Gln Thr Trp Gln Phe Leu Ser Ser<br>750 755 760 | | 2427 |
| cgt gct ggt atc atc ttc att gtc ctg cag aag gtg gag aag acc ctg<br>Arg Ala Gly Ile Ile Phe Ile Val Leu Gln Lys Val Glu Lys Thr Leu<br>765 770 775 | | 2475 |
| ctc agg cag cag gtg gag ctg tac cgc ctt ctc agc agg aac act tac<br>Leu Arg Gln Gln Val Glu Leu Tyr Arg Leu Leu Ser Arg Asn Thr Tyr<br>780 785 790 | | 2523 |
| ctg gag tgg gag gac agt gtc ctg ggg cgg cac atc ttc tgg aga cga<br>Leu Glu Trp Glu Asp Ser Val Leu Gly Arg His Ile Phe Trp Arg Arg<br>795 800 805 810 | | 2571 |
| ctc aga aaa gcc ctg ctg gat ggt aaa tca tgg aat cca gaa gga aca<br>Leu Arg Lys Ala Leu Leu Asp Gly Lys Ser Trp Asn Pro Glu Gly Thr<br>815 820 825 | | 2619 |
| gtg ggt aca gga tgc aat tgg cag gaa gca aca tct atc tga<br>Val Gly Thr Gly Cys Asn Trp Gln Glu Ala Thr Ser Ile<br>830 835 | | 2661 |
| agaggaaaaa taaaaacctc ctgaggcatt tcttgcccag ctgggtccaa cacttgttca | | 2721 |
| gttaataagt attaaatgct gccacatgtc aggccttatg ctaagggtga gtaattccat | | 2781 |
| ggtgcactag atatgcaggg ctgctaatct caaggagctt ccagtgcaga gggaataaat | | 2841 |
| gctagactaa aatacagagt cttccaggtg ggcatttcaa ccaactcagt caaggaaccc | | 2901 |
| atgacaaaga aagtcatttc aactcttacc tcatcaagtt gaataaagac agagaaaaca | | 2961 |
| gaaagagaca ttgttctttt cctgagtctt ttgaatggaa attgtattat gttatagcca | | 3021 |
| tcataaaacc attttggtag ttttgactga actgggtgtt cactttttcc ttttgattg | | 3081 |
| aatacaattt aaattctact tgatgactgc agtcgtcaag gggctcctga tgcaagatgc | | 3141 |
| cccttccatt ttaagtctgt ctccttacag aggttaaagt ctagtggcta attcctaagg | | 3201 |
| aaacctgatt aacacatgct cacaaccatc ctggtcattc tcgagcatgt tctattttt | | 3261 |
| aactaatcac ccctgatata tttttatttt tatatatcca gttttcattt ttttacgtct | | 3321 |
| tgcctataag ctaatatcat aaataaggtt gtttaagacg tgcttcaaat atccatatta | | 3381 |
| accactattt ttcaaggaag tatggaaaag tacactctgt cactttgtca ctcgatgtca | | 3441 |
| ttccaaagtt attgcctact aagtaatgac tgtcatgaaa gcagcattga aataatttgt | | 3501 |

```
ttaaaggggg cactctttta aacgggaaga aaatttccgc ttcctggtct tatcatggac    3561
aatttgggct agaggcagga aggaagtggg atgacctcag gaggtcacct tttcttgatt    3621
ccagaaacat atgggctgat aaacccgggg tgacctcatg aaatgagttg cagcagaagt    3681
ttatttttt  cagaacaagt gatgtttgat ggacctctga atctctttag ggagacacag    3741
atggctggga tccctcccct gtaccttct  cactgccagg agaactacgt gtgaaggtat    3801
tcaaggcagg gagtatacat tgctgtttcc tgttgggcaa tgctccttga ccacattttg    3861
ggaagagtgg atgttatcat tgagaaaaca atgtgtctgg aattaatggg gttcttataa    3921
agaaggttcc cagaaaagaa tgttcatcca gcctcctcag aaacagaaca ttcaagaaaa    3981
ggacaatcag gatgtcatca gggaaatgaa aataaaaacc acaatgagat atcaccttat    4041
accaggtaga atggctacta taaaaaaatg aagtgtcatc aaggatatag agaaattgga    4101
acccttcttc actgctggag ggaatggaaa atggtgtagc cgttatgaaa aacagtacgg    4161
aggtttctca aaaattaaaa atagaactgc tatatgatcc agcaatctca cttctgtata    4221
tatacccaaa ataattgaaa tcagaatttc aagaaaatat ttacactccc atgttcattg    4281
tggcactctt cacaatcact gtttccaaag ttatggaaac aacccaaatt tccattgaaa    4341
aataaatgga caaagaaaat gtgcatatac gtacaatggg atattattca gcctaaaaaa    4401
aggggaatc ctgttattta tgacaacatg aataaacccg gaggccatta tgctatgtaa    4461
aatgagcaag taacagaaag acaaatactg cctgatttca tttatatgag gttctaaaat    4521
agtcaaactc atagaagcag agaatagaac agtggttcct agggaaaagg aggaagggag    4581
aaatgaggaa atagggagtt gtctaattgg tataaaatta tagtatgcaa gatgaattag    4641
ctctaaagat cagctgtata gcagagttcg tataatgaac aatactgtat tatgcactta    4701
acatttgtt  aagagggtac ctctcatgtt aagtgttctt accatataca tatacacaag    4761
gaagcttttg gaggtgatgg atatatttat taccttgatt gtggtgatgg tttgacaggt    4821
atgtgactat gtctaaactc atcaaattgt atacattaaa tatatgcagt tttataatat    4881
caattatgtc tgaatgaagc tataaaaaag aaaagacaac aaaattcagt tgtcaaaact    4941
ggaaatatga ccacagtcag aagtgtttgt tactgagtgt ttcagagtgt gtttggtttg    5001
agcaggtcta gggtgattga acatccctgg gtgtgtttcc atgtctcatg tactagtgaa    5061
agtagatgtg tgcatttgtg cacatatccc tatgtatccc tatcagggct gtgtgtattt    5121
gaaagtgtgt gtgtccgcat gatcatatct gtatagaaga gagtgtgatt atatttcttg    5181
aagaatacat ccatttgaaa tggatgtcta tggctgtttg agatgagttc tctactcttg    5241
tgcttgtaca gtagtctccc cttatccctt atgcttggtg gatacgttct tagaccccaa    5301
gtggatctct gagaccgcag atggtaccaa acctcatata tgcaatattt tttcctatac    5361
ataaatacct aagataaagt tcatcttctg aattaggcac agtaagagat taacaataac    5421
taacaataaa attgaatagt tataataata tattgtaata aaagttatgt gaatgtgatc    5481
tcttctttc tctctctcaa aa                                              5503
```

<210> SEQ ID NO 2
<211> LENGTH: 839
<212> TYPE: PRT
<213> ORGANISM: Homo sapiens

<400> SEQUENCE: 2

```
Met Met Ser Ala Ser Arg Leu Ala Gly Thr Leu Ile Pro Ala Met Ala
1               5                   10                  15

Phe Leu Ser Cys Val Arg Pro Glu Ser Trp Glu Pro Cys Val Glu Val
```

-continued

```
                    20                  25                  30
Val Pro Asn Ile Thr Tyr Gln Cys Met Glu Leu Asn Phe Tyr Lys Ile
                35                  40                  45
Pro Asp Asn Leu Pro Phe Ser Thr Lys Asn Leu Asp Leu Ser Phe Asn
                50                  55                  60
Pro Leu Arg His Leu Gly Ser Tyr Ser Phe Phe Ser Phe Pro Glu Leu
65                  70                  75                  80
Gln Val Leu Asp Leu Ser Arg Cys Glu Ile Gln Thr Ile Glu Asp Gly
                85                  90                  95
Ala Tyr Gln Ser Leu Ser His Leu Ser Thr Leu Ile Leu Thr Gly Asn
                100                 105                 110
Pro Ile Gln Ser Leu Ala Leu Gly Ala Phe Ser Gly Leu Ser Ser Leu
                115                 120                 125
Gln Lys Leu Val Ala Val Glu Thr Asn Leu Ala Ser Leu Glu Asn Phe
                130                 135                 140
Pro Ile Gly His Leu Lys Thr Leu Lys Glu Leu Asn Val Ala His Asn
145                 150                 155                 160
Leu Ile Gln Ser Phe Lys Leu Pro Glu Tyr Phe Ser Asn Leu Thr Asn
                165                 170                 175
Leu Glu His Leu Asp Leu Ser Ser Asn Lys Ile Gln Ser Ile Tyr Cys
                180                 185                 190
Thr Asp Leu Arg Val Leu His Gln Met Pro Leu Leu Asn Leu Ser Leu
                195                 200                 205
Asp Leu Ser Leu Asn Pro Met Asn Phe Ile Gln Pro Gly Ala Phe Lys
                210                 215                 220
Glu Ile Arg Leu His Lys Leu Thr Leu Arg Asn Asn Phe Asp Ser Leu
225                 230                 235                 240
Asn Val Met Lys Thr Cys Ile Gln Gly Leu Ala Gly Leu Glu Val His
                245                 250                 255
Arg Leu Val Leu Gly Glu Phe Arg Asn Glu Gly Asn Leu Glu Lys Phe
                260                 265                 270
Asp Lys Ser Ala Leu Glu Gly Leu Cys Asn Leu Thr Ile Glu Glu Phe
                275                 280                 285
Arg Leu Ala Tyr Leu Asp Tyr Tyr Leu Asp Asp Ile Ile Asp Leu Phe
                290                 295                 300
Asn Cys Leu Thr Asn Val Ser Ser Phe Ser Leu Val Ser Val Thr Ile
305                 310                 315                 320
Glu Arg Val Lys Asp Phe Ser Tyr Asn Phe Gly Trp Gln His Leu Glu
                325                 330                 335
Leu Val Asn Cys Lys Phe Gly Gln Phe Pro Thr Leu Lys Leu Lys Ser
                340                 345                 350
Leu Lys Arg Leu Thr Phe Thr Ser Asn Lys Gly Gly Asn Ala Phe Ser
                355                 360                 365
Glu Val Asp Leu Pro Ser Leu Glu Phe Leu Asp Leu Ser Arg Asn Gly
                370                 375                 380
Leu Ser Phe Lys Gly Cys Cys Ser Gln Ser Asp Phe Gly Thr Thr Ser
385                 390                 395                 400
Leu Lys Tyr Leu Asp Leu Ser Phe Asn Gly Val Ile Thr Met Ser Ser
                405                 410                 415
Asn Phe Leu Gly Leu Glu Gln Leu Glu His Leu Asp Phe Gln His Ser
                420                 425                 430
Asn Leu Lys Gln Met Ser Glu Phe Ser Val Phe Leu Ser Leu Arg Asn
                435                 440                 445
```

```
Leu Ile Tyr Leu Asp Ile Ser His Thr His Thr Arg Val Ala Phe Asn
        450                 455                 460

Gly Ile Phe Asn Gly Leu Ser Ser Leu Glu Val Leu Lys Met Ala Gly
465                 470                 475                 480

Asn Ser Phe Gln Glu Asn Phe Leu Pro Asp Ile Phe Thr Glu Leu Arg
                    485                 490                 495

Asn Leu Thr Phe Leu Asp Leu Ser Gln Cys Gln Leu Glu Gln Leu Ser
                500                 505                 510

Pro Thr Ala Phe Asn Ser Leu Ser Ser Leu Gln Val Leu Asn Met Ser
            515                 520                 525

His Asn Asn Phe Phe Ser Leu Asp Thr Phe Pro Tyr Lys Cys Leu Asn
530                 535                 540

Ser Leu Gln Val Leu Asp Tyr Ser Leu Asn His Ile Met Thr Ser Lys
545                 550                 555                 560

Lys Gln Glu Leu Gln His Phe Pro Ser Ser Leu Ala Phe Leu Asn Leu
                565                 570                 575

Thr Gln Asn Asp Phe Ala Cys Thr Cys Glu His Gln Ser Phe Leu Gln
                580                 585                 590

Trp Ile Lys Asp Gln Arg Gln Leu Leu Val Glu Val Glu Arg Met Glu
            595                 600                 605

Cys Ala Thr Pro Ser Asp Lys Gln Gly Met Pro Val Leu Ser Leu Asn
610                 615                 620

Ile Thr Cys Gln Met Asn Lys Thr Ile Ile Gly Val Ser Val Leu Ser
625                 630                 635                 640

Val Leu Val Val Ser Val Val Ala Val Leu Val Tyr Lys Phe Tyr Phe
                645                 650                 655

His Leu Met Leu Leu Ala Gly Cys Ile Lys Tyr Gly Arg Gly Glu Asn
                660                 665                 670

Ile Tyr Asp Ala Phe Val Ile Tyr Ser Ser Gln Asp Glu Asp Trp Val
            675                 680                 685

Arg Asn Glu Leu Val Lys Asn Leu Glu Glu Gly Val Pro Pro Phe Gln
            690                 695                 700

Leu Cys Leu His Tyr Arg Asp Phe Ile Pro Gly Val Ala Ile Ala Ala
705                 710                 715                 720

Asn Ile Ile His Glu Gly Phe His Lys Ser Arg Lys Val Ile Val Val
                725                 730                 735

Val Ser Gln His Phe Ile Gln Ser Arg Trp Cys Ile Phe Glu Tyr Glu
                740                 745                 750

Ile Ala Gln Thr Trp Gln Phe Leu Ser Ser Arg Ala Gly Ile Ile Phe
            755                 760                 765

Ile Val Leu Gln Lys Val Glu Lys Thr Leu Leu Arg Gln Gln Val Glu
770                 775                 780

Leu Tyr Arg Leu Leu Ser Arg Asn Thr Tyr Leu Glu Trp Glu Asp Ser
785                 790                 795                 800

Val Leu Gly Arg His Ile Phe Trp Arg Arg Leu Arg Lys Ala Leu Leu
                805                 810                 815

Asp Gly Lys Ser Trp Asn Pro Glu Gly Thr Val Gly Thr Gly Cys Asn
            820                 825                 830

Trp Gln Glu Ala Thr Ser Ile
        835

<210> SEQ ID NO 3
<211> LENGTH: 608
<212> TYPE: PRT
<213> ORGANISM: Homo sapiens
```

<400> SEQUENCE: 3

```
Glu Ser Trp Glu Pro Cys Val Glu Val Val Pro Asn Ile Thr Tyr Gln
1               5                   10                  15

Cys Met Glu Leu Asn Phe Tyr Lys Ile Pro Asp Asn Leu Pro Phe Ser
            20                  25                  30

Thr Lys Asn Leu Asp Leu Ser Phe Asn Pro Leu Arg His Leu Gly Ser
        35                  40                  45

Tyr Ser Phe Phe Ser Phe Pro Glu Leu Gln Val Leu Asp Leu Ser Arg
    50                  55                  60

Cys Glu Ile Gln Thr Ile Glu Asp Gly Ala Tyr Gln Ser Leu Ser His
65                  70                  75                  80

Leu Ser Thr Leu Ile Leu Thr Gly Asn Pro Ile Gln Ser Leu Ala Leu
                85                  90                  95

Gly Ala Phe Ser Gly Leu Ser Ser Leu Gln Lys Leu Val Ala Val Glu
            100                 105                 110

Thr Asn Leu Ala Ser Leu Glu Asn Phe Pro Ile Gly His Leu Lys Thr
        115                 120                 125

Leu Lys Glu Leu Asn Val Ala His Asn Leu Ile Gln Ser Phe Lys Leu
    130                 135                 140

Pro Glu Tyr Phe Ser Asn Leu Thr Asn Leu Glu His Leu Asp Leu Ser
145                 150                 155                 160

Ser Asn Lys Ile Gln Ser Ile Tyr Cys Thr Asp Leu Arg Val Leu His
                165                 170                 175

Gln Met Pro Leu Leu Asn Leu Ser Leu Asp Leu Ser Leu Asn Pro Met
            180                 185                 190

Asn Phe Ile Gln Pro Gly Ala Phe Lys Glu Ile Arg Leu His Lys Leu
        195                 200                 205

Thr Leu Arg Asn Asn Phe Asp Ser Leu Asn Val Met Lys Thr Cys Ile
    210                 215                 220

Gln Gly Leu Ala Gly Leu Glu Val His Arg Leu Val Leu Gly Glu Phe
225                 230                 235                 240

Arg Asn Glu Gly Asn Leu Glu Lys Phe Asp Lys Ser Ala Leu Glu Gly
                245                 250                 255

Leu Cys Asn Leu Thr Ile Glu Glu Phe Arg Leu Ala Tyr Leu Asp Tyr
            260                 265                 270

Tyr Leu Asp Asp Ile Ile Asp Leu Phe Asn Cys Leu Thr Asn Val Ser
        275                 280                 285

Ser Phe Ser Leu Val Ser Val Thr Ile Glu Arg Val Lys Asp Phe Ser
    290                 295                 300

Tyr Asn Phe Gly Trp Gln His Leu Glu Leu Val Asn Cys Lys Phe Gly
305                 310                 315                 320

Gln Phe Pro Thr Leu Lys Leu Lys Ser Leu Lys Arg Leu Thr Phe Thr
                325                 330                 335

Ser Asn Lys Gly Gly Asn Ala Phe Ser Glu Val Asp Leu Pro Ser Leu
            340                 345                 350

Glu Phe Leu Asp Leu Ser Arg Asn Gly Leu Ser Phe Lys Gly Cys Cys
        355                 360                 365

Ser Gln Ser Asp Phe Gly Thr Thr Ser Leu Lys Tyr Leu Asp Leu Ser
    370                 375                 380

Phe Asn Gly Val Ile Thr Met Ser Ser Asn Phe Leu Gly Leu Glu Gln
385                 390                 395                 400

Leu Glu His Leu Asp Phe Gln His Ser Asn Leu Lys Gln Met Ser Glu
                405                 410                 415
```

```
Phe Ser Val Phe Leu Ser Leu Arg Asn Leu Ile Tyr Leu Asp Ile Ser
            420                 425                 430

His Thr His Thr Arg Val Ala Phe Asn Gly Ile Phe Asn Gly Leu Ser
        435                 440                 445

Ser Leu Glu Val Leu Lys Met Ala Gly Asn Ser Phe Gln Glu Asn Phe
    450                 455                 460

Leu Pro Asp Ile Phe Thr Glu Leu Arg Asn Leu Thr Phe Leu Asp Leu
465                 470                 475                 480

Ser Gln Cys Gln Leu Glu Gln Leu Ser Pro Thr Ala Phe Asn Ser Leu
            485                 490                 495

Ser Ser Leu Gln Val Leu Asn Met Ser His Asn Asn Phe Phe Ser Leu
                500                 505                 510

Asp Thr Phe Pro Tyr Lys Cys Leu Asn Ser Leu Gln Val Leu Asp Tyr
            515                 520                 525

Ser Leu Asn His Ile Met Thr Ser Lys Lys Gln Glu Leu Gln His Phe
    530                 535                 540

Pro Ser Ser Leu Ala Phe Leu Asn Leu Thr Gln Asn Asp Phe Ala Cys
545                 550                 555                 560

Thr Cys Glu His Gln Ser Phe Leu Gln Trp Ile Lys Asp Gln Arg Gln
            565                 570                 575

Leu Leu Val Glu Val Glu Arg Met Glu Cys Ala Thr Pro Ser Asp Lys
                580                 585                 590

Gln Gly Met Pro Val Leu Ser Leu Asn Ile Thr Cys Gln Met Asn Lys
            595                 600                 605

<210> SEQ ID NO 4
<211> LENGTH: 30
<212> TYPE: DNA
<213> ORGANISM: Artificial
<220> FEATURE:
<223> OTHER INFORMATION: primer

<400> SEQUENCE: 4
gattagcata cttagactac tacctccatg                                    30

<210> SEQ ID NO 5
<211> LENGTH: 24
<212> TYPE: DNA
<213> ORGANISM: Artificial
<220> FEATURE:
<223> OTHER INFORMATION: primer

<400> SEQUENCE: 5
tgtgggaaac gttccaaatt taca                                          24

<210> SEQ ID NO 6
<211> LENGTH: 24
<212> TYPE: DNA
<213> ORGANISM: Artificial
<220> FEATURE:
<223> OTHER INFORMATION: primer

<400> SEQUENCE: 6
tgagtttcaa aggttgctgt tctc                                          24

<210> SEQ ID NO 7
<211> LENGTH: 28
<212> TYPE: DNA
<213> ORGANISM: Artificial
<220> FEATURE:
<223> OTHER INFORMATION: primer
```

```
<400> SEQUENCE: 7
aggaatactg aaaactcact catttgtt                                          28

<210> SEQ ID NO 8
<211> LENGTH: 15
<212> TYPE: DNA
<213> ORGANISM: Artificial
<220> FEATURE:
<223> OTHER INFORMATION: primer

<400> SEQUENCE: 8
ttaggctggt tgtcc                                                        15

<210> SEQ ID NO 9
<211> LENGTH: 15
<212> TYPE: DNA
<213> ORGANISM: Artificial
<220> FEATURE:
<223> OTHER INFORMATION: primer

<400> SEQUENCE: 9
ttaggctgat tgtcc                                                        15

<210> SEQ ID NO 10
<211> LENGTH: 30
<212> TYPE: DNA
<213> ORGANISM: Artificial
<220> FEATURE:
<223> OTHER INFORMATION: primer

<400> SEQUENCE: 10
gattagcata cttagactac tacctccatg                                        30

<210> SEQ ID NO 11
<211> LENGTH: 24
<212> TYPE: DNA
<213> ORGANISM: Artificial
<220> FEATURE:
<223> OTHER INFORMATION: primer

<400> SEQUENCE: 11
tgtgggaaac gttccaaatt taca                                              24

<210> SEQ ID NO 12
<211> LENGTH: 25
<212> TYPE: DNA
<213> ORGANISM: Artificial
<220> FEATURE:
<223> OTHER INFORMATION: primer

<400> SEQUENCE: 12
ccattgaaga attccgatta gcata                                             25

<210> SEQ ID NO 13
<211> LENGTH: 23
<212> TYPE: DNA
<213> ORGANISM: Artificial
<220> FEATURE:
<223> OTHER INFORMATION: primer

<400> SEQUENCE: 13 cactccaccag ggaaaatgaa gaa                                              23

<210> SEQ ID NO 14
<211> LENGTH: 24
```

```
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(24)

<400> SEQUENCE: 14
tgagtttcaa aggttgctgt tctc                                    24

<210> SEQ ID NO 15
<211> LENGTH: 28
<212> TYPE: DNA
<213> ORGANISM: Artificial
<220> FEATURE:
<223> OTHER INFORMATION: primer

<400> SEQUENCE: 15
aggaatactg aaaactcact catttgtt                                28

<210> SEQ ID NO 16
<211> LENGTH: 20
<212> TYPE: DNA
<213> ORGANISM: Artificial
<220> FEATURE:
<223> OTHER INFORMATION: CpG oligonucleotide

<400> SEQUENCE: 16
tccatgacgt tcctgacgtt                                         20

<210> SEQ ID NO 17
<211> LENGTH: 34
<212> TYPE: PRT
<213> ORGANISM: Artificial
<220> FEATURE:
<223> OTHER INFORMATION: inhibitory peptide

<400> SEQUENCE: 17

Arg Lys Lys Arg Arg Gln Arg Arg Gly Lys Lys Tyr Ser Arg Gly
1               5                   10                  15

Glu Ser Ile Tyr Asp Ala Phe Val Ile Tyr Ser Ser Gln Asn Glu Asp
            20                  25                  30

Trp Val

<210> SEQ ID NO 18
<211> LENGTH: 34
<212> TYPE: PRT
<213> ORGANISM: Artificial
<220> FEATURE:
<223> OTHER INFORMATION: inhibitory mutant peptide

<400> SEQUENCE: 18

Arg Lys Lys Arg Arg Gln Arg Arg Gly Glu Glu Tyr Ser Glu Gly
1               5                   10                  15

Glu Ser Ile Tyr Asp Ala Phe Val Ile Tyr Ser Ser Gln Asn Glu Asp
            20                  25                  30

Trp Val

<210> SEQ ID NO 19
<211> LENGTH: 18
<212> TYPE: DNA
<213> ORGANISM: Artificial
<220> FEATURE:
<223> OTHER INFORMATION: TLR7/9 inhibitory ODN
```

```
<400> SEQUENCE: 19
tgctcctgga ggggttgt                                               18

<210> SEQ ID NO 20
<211> LENGTH: 15
<212> TYPE: DNA
<213> ORGANISM: Artificial
<220> FEATURE:
<223> OTHER INFORMATION: Control ODN

<400> SEQUENCE: 20
tcctgcaggt taagt                                                  15

<210> SEQ ID NO 21
<211> LENGTH: 25
<212> TYPE: DNA
<213> ORGANISM: Artificial
<220> FEATURE:
<223> OTHER INFORMATION: primer

<400> SEQUENCE: 21
ccattgaaga attccgatta gcata                                       25

<210> SEQ ID NO 22
<211> LENGTH: 23
<212> TYPE: DNA
<213> ORGANISM: Artificial
<220> FEATURE:
<223> OTHER INFORMATION: primer

<400> SEQUENCE: 22
cactcaccag ggaaaatgaa gaa                                         23

<210> SEQ ID NO 23
<211> LENGTH: 16
<212> TYPE: DNA
<213> ORGANISM: Artificial
<220> FEATURE:
<223> OTHER INFORMATION: Allele specific oligonucleotide

<400> SEQUENCE: 23
cctcgatgat attatt                                                 16

<210> SEQ ID NO 24
<211> LENGTH: 16
<212> TYPE: DNA
<213> ORGANISM: Artificial
<220> FEATURE:
<223> OTHER INFORMATION: Allele specific oligonucleotide

<400> SEQUENCE: 24
ctcgatggta ttattg                                                 16
```